US012760038B2

(12) United States Patent
Ran et al.

(10) Patent No.: US 12,760,038 B2
(45) Date of Patent: Oct. 13, 2026

(54) ORGANIC COMPOUND AND APPLICATION THEREOF

(71) Applicants: Wuhan Tianma Microelectronics Co., Ltd., Wuhan (CN); Wuhan Tianma Microelectronics Co., Ltd. Shanghai Branch, Shanghai (CN)

(72) Inventors: Quan Ran, Wuhan (CN); Lei Zhang, Wuhan (CN); Wei Gao, Wuhan (CN)

(73) Assignees: Wuhan Tianma Microelectronics Co., Ltd., Wuhan (CN); Wuhan Tianma Microelectronics Co., Ltd. Shanghai Branch, Shanghai (CN)

( * ) Notice: Subject to any disclaimer, the term of this patent is extended or adjusted under 35 U.S.C. 154(b) by 1048 days.

(21) Appl. No.: 17/579,926

(22) Filed: Jan. 20, 2022

(65) Prior Publication Data

US 2022/0144786 A1 May 12, 2022

(30) Foreign Application Priority Data

Aug. 20, 2021 (CN) ......................... 202110960147.5

(51) Int. Cl.
*H10K 50/11* (2023.01)
*C07D 251/24* (2006.01)
(Continued)

(52) U.S. Cl.
CPC ......... *C07D 519/00* (2013.01); *C07D 251/24* (2013.01); *C07D 487/04* (2013.01); *C07D 493/00* (2013.01); *C07D 495/00* (2013.01); *H10K 85/622* (2023.02); *H10K 85/626* (2023.02); *H10K 85/654* (2023.02); *H10K 85/6572* (2023.02); *H10K 85/6574* (2023.02); *H10K 85/6576* (2023.02); *H10K 50/11* (2023.02); *H10K 50/16* (2023.02);
(Continued)

(58) Field of Classification Search
CPC .................................................... H10K 85/572
See application file for complete search history.

(56) References Cited

U.S. PATENT DOCUMENTS

2013/0001522 A1* 1/2013 Lee ...................... C07D 401/10 257/E51.024
2013/0099206 A1* 4/2013 Jung .................... C07D 471/04 257/E51.026
2013/0240866 A1* 9/2013 Dogra .................... H10K 50/16 257/40

FOREIGN PATENT DOCUMENTS

CN 106554319 A 4/2017
CN 110878088 A 3/2020
(Continued)

*Primary Examiner* — Sean M DeGuire
(74) *Attorney, Agent, or Firm* — KDW Firm PLLC

(57) ABSTRACT

Provided are an organic compound and an application thereof. The compound has a relatively deep LUMO energy level and can reduce a potential barrier of electron transport, improve an electron injection ability, and effectively reduce the voltage of an OLED device. Such compounds all have relatively deep HOMO energy levels and can effectively block holes so that more holes and electrons are recombined in a light-emitting region, achieving higher luminescence efficiency. Materials of an electron transport layer and/or a hole blocking layer suitable for the OLED device can reduce the voltage and power consumption, improve the luminescence efficiency, and extend the service life of the device so that the OLED device has better comprehensive performance.

15 Claims, 1 Drawing Sheet

(51) Int. Cl.

| | |
|---|---|
| ***C07D 487/04*** | (2006.01) |
| ***C07D 493/00*** | (2006.01) |
| ***C07D 495/00*** | (2006.01) |
| ***C07D 519/00*** | (2006.01) |
| ***H10K 85/60*** | (2023.01) |
| *H10K 50/16* | (2023.01) |
| *H10K 50/18* | (2023.01) |
| *H10K 101/10* | (2023.01) |
| *H10K 101/30* | (2023.01) |
| *H10K 101/40* | (2023.01) |

(52) U.S. Cl.

CPC ......... *H10K 50/18* (2023.02); *H10K 2101/10* (2023.02); *H10K 2101/30* (2023.02); *H10K 2101/40* (2023.02)

(56) References Cited

FOREIGN PATENT DOCUMENTS

| | | | | |
|---|---|---|---|---|
| CN | 111574434 | A | | 8/2020 |
| CN | 112778225 | A | | 5/2021 |
| WO | 2009008353 | A1 | | 1/2009 |
| WO | WO-2021256871 | A1 | * | 12/2021 |

* cited by examiner

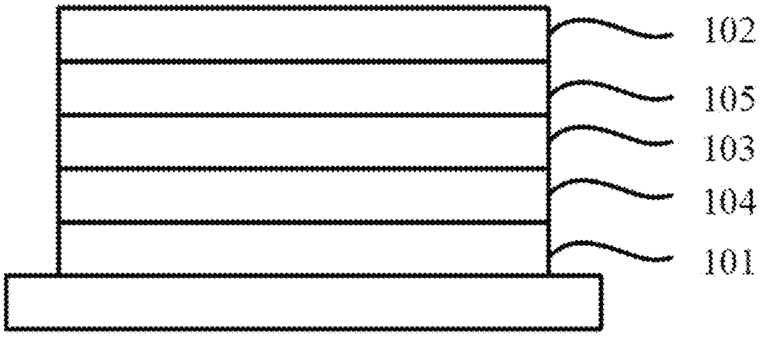
102
105
103
104
101

ORGANIC COMPOUND AND APPLICATION THEREOF

CROSS-REFERENCE TO RELATED APPLICATION(S)

This application claims priority to Chinese Patent Application No. CN202110960147.5 filed Aug. 20, 2021, the disclosure of which is incorporated herein by reference in its entirety.

TECHNICAL FIELD

The present disclosure belongs to the technical field of organic electroluminescent materials and relates to an organic compound and an application thereof.

BACKGROUND

Organic electroluminescence technology is currently one of the most promising new technologies in the field of optoelectronics. Compared with inorganic electroluminescent devices, organic light-emitting diode (OLED) devices have the advantages of self-luminescence, low power consumption, a high contrast, a wide color gamut, flexibility and foldability and have attracted the wide attention of scientific researchers and corporate researchers. They have been successfully applied in business and have been widely used in many industries such as flexible display, flat panel display and solid-state lighting.

Tris(8-hydroxyquinolinato)aluminium (Alq3) is used in traditional electroluminescent devices as an electron transport material. However, Alq3 has a relatively low electron mobility (of about $10^{-6}$ $cm^2/Vs$) so that electron transport and hole transport of the devices are unbalanced. As electroluminescent devices are commercialized and become practical, it is desired to obtain a material of an electron transport layer (ETL), which has higher transport efficiency and better performance. Researchers have explored much in the art.

WO2007/011170A1 and CN101003508A respectively disclose a series of derivatives of naphthoimidazole and pyrene, which are used as electron transport and injection materials in electroluminescent devices to improve the luminescence efficiency of the devices.

US2006/0204784 and US2007/0048545 of Kodak Company disclose an organic electroluminescent device with a hybrid electron transport layer, where the hybrid electron transport material is obtained by doping the following materials: (a) a first compound with the lowest lowest unoccupied molecular orbital (LUMO) energy level in the layer, (b) a second compound with a higher LUMO energy level than the first compound and a low turn-on voltage, and a metal material with a work function of less than 4.2 eV. Devices based on the hybrid electron transport layer have improved efficiency, lifetime and the like. However, the preceding electron transport material has a planar molecular structure and a large intermolecular attractive force and is not conducive to evaporation and application. Moreover, the electron transport material also has the defects of relatively low mobility, poor energy level matching, poor thermal stability, a short service life and doping, which restricts the further development of OLED display devices.

With the progress of OLED display technology, many electron transport materials commercially available at present, such as batho-phenanthroline (BPhen), bathocuproine (BCP) and TmPyPB, can generally satisfy the market demand for organic electroluminescent panels, yet have a relatively low glass transition temperature which is generally less than 85° C. When the devices are operating, generated Joule heat will cause molecular degradation and changes in molecular structure, resulting in low panel efficiency and poor thermal stability. Moreover, the symmetry of the molecular structure is very regular so that the electron transport materials are easy to crystallize after long-term use. Once the electron transport materials crystallize, an intermolecular charge transition mechanism will differ from the mechanism of the normally operated amorphous film, so that electron transport performance decreases, the electron mobility and the hole mobility of the entire device are unbalanced, and excitons are formed with greatly reduced efficiency and concentrated at an interface between an electron transport layer and a light-emitting layer, resulting in a serious decrease in device efficiency and lifetime.

Therefore, in the art, it is of high value in practical applications to design and develop stable and efficient electron transport materials and/or electron injection materials that can simultaneously have high electron mobility and high glass transition temperatures and can be effectively doped with metals, so as to reduce device voltage, improve device efficiency, and extend device lifetimes.

SUMMARY

In view of defects in the related art, an object of the present disclosure is to provide an organic compound and an application thereof.

To achieve this object, the present disclosure adopts technical solutions described below.

A first aspect of the present disclosure is to provide an organic compound, where the organic compound has a structure represented by Formula I:

Formula I

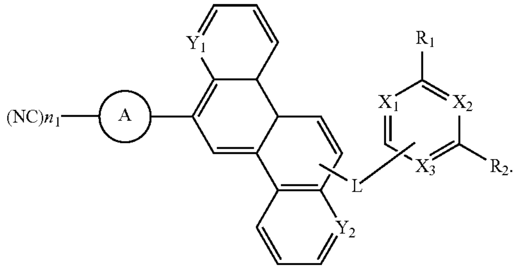

The ring A is selected from a substituted or unsubstituted C6-C20 aromatic ring, or a substituted or unsubstituted C5-C30 aromatic heterocycle.

$Y_1$ and $Y_2$ are independently selected from a C atom or a N atom.

L is selected from substituted or unsubstituted C6-C20 aryl, or substituted or unsubstituted C5-C30 heteroaryl.

$X_1$ to $X_3$ are independently selected from the C atom or the N atom, and at least one of $X_1$ to $X_3$ is N.

$R_1$ and $R_2$ are independently selected from substituted or unsubstituted C6-C30 aryl, or substituted or unsubstituted C5-C30 heteroaryl.

$n_1$ is an integer from 0 to 3.

In the present disclosure, C6-C20 may each independently be C6, C9, C10, C12, C13, C14, C15, C16, C18, C19 or the like.

C5-C30 may each independently be C6, C7, C8, C9, C10, C12, C13, C14, C15, C16, C18, C20, C22, C24, C26, C28, C29 or the like.

C6-C30 may each independently be C7, C8, C9, C10, C12, C13, C14, C15, C16, C18, C20, C22, C24, C26, C28, C29 or the like.

In the organic compound provided by the present disclosure, the cooperation of a skeleton structure with a substituent has the good characteristics of an electron transport (ET) material and a relatively deep LUMO energy level and can reduce a potential barrier of electron transport, improve electron injection ability, and effectively reduce the voltage of an OLED device. Such compounds all have relatively deep highest occupied molecular orbital (HOMO) energy levels and can effectively block holes so that more holes and electrons are recombined in a light-emitting region, achieving higher luminescence efficiency.

A second aspect of the present disclosure is to provide a material of an electron transport layer, wherein the material of the electron transport layer includes the organic compound as described in the first aspect.

A third aspect of the present disclosure is to provide a material of a hole blocking layer, wherein the material of the hole blocking layer includes the organic compound as described in the first aspect.

A fourth aspect of the present disclosure is to provide an OLED device. The OLED device includes an anode, a cathode and an organic thin film layer disposed between the anode and the cathode, wherein a material of the organic thin film layer includes the organic compound as described in the first aspect.

A fifth aspect of the present disclosure is to provide a display panel. The display panel includes the OLED device as described in the fourth aspect.

A sixth aspect of the present disclosure is to provide an electronic apparatus. The electronic apparatus includes the display panel as described in the fifth aspect.

Compared with the related art, the present disclosure has beneficial effects described below.

The compounds of the present disclosure have relatively deep LUMO energy levels and can reduce the potential barrier of electron transport, improve the electron injection ability, and effectively reduce the voltage of the OLED device. Such compounds all have relatively deep HOMO energy levels and can effectively block holes so that more holes and electrons are recombined in the light-emitting region, achieving the higher luminescence efficiency. Materials of the electron transport layer and/or the hole blocking layer suitable for the OLED device can reduce the voltage and power consumption, improve the luminescence efficiency, and extend the service life of the device so that the OLED device has better comprehensive performance.

BRIEF DESCRIPTION OF DRAWINGS

The FIGURE is a structure diagram of an OLED device according to the present disclosure.

REFERENCE LIST

101 anode
102 cathode
103 light-emitting layer
104 first organic thin film layer
105 second organic thin film layer

DETAILED DESCRIPTION

Technical solutions of the present disclosure are further described below through embodiments. It is to be understood by those skilled in the art that the embodiments described herein are used for a better understanding of the present disclosure and are not to be construed as specific limitations to the present disclosure.

A first aspect of the present disclosure is to provide an organic compound, where the organic compound has a structure represented by Formula I:

Formula I

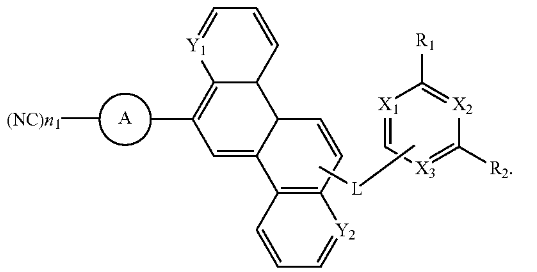

The ring A is selected from a substituted or unsubstituted C6-C20 aromatic ring, or a substituted or unsubstituted C5-C30 aromatic heterocycle.

$Y_1$ and $Y_2$ are independently selected from a C atom or a N atom.

L is selected from substituted or unsubstituted C6-C20 aryl, or substituted or unsubstituted C5-C30 heteroaryl.

$X_1$ to $X_3$ are independently selected from the C atom or the N atom, and at least one of $X_1$ to $X_3$ is N.

$R_1$ and $R_2$ are independently selected from substituted or unsubstituted C6-C30 aryl, or substituted or unsubstituted C5-C30 heteroaryl.

$n_1$ is an integer from 0 to 3.

In the present disclosure, C6-C20 may each independently be C6, C9, C10, C12, C13, C14, C15, C16, C18, C19 or the like.

C5-C30 may each independently be C6, C7, C8, C9, C10, C12, C13, C14, C15, C16, C18, C20, C22, C24, C26, C28, C29 or the like.

C6-C30 may each independently be C7, C8, C9, C10, C12, C13, C14, C15, C16, C18, C20, C22, C24, C26, C28, C29 or the like.

C6-C30 aryl involved in the present disclosure exemplarily includes, but is not limited to, phenyl, biphenyl, terphenyl, naphthyl, anthryl, phenanthryl, pyrenyl, fluorenyl and derivatives thereof (dimethylfluorenyl, diphenylfluorenyl), indenyl, perylenyl, triphenylene or the like.

C5-C30 heteroaryl involved in the present disclosure exemplarily includes, but is not limited to, pyridyl, pyrazinyl, pyridazinyl, pyrimidyl, triazinyl, quinolyl, isoquinolyl, quinoxalinyl, quinazolinyl, pyridopyridyl, an o-phenanthroline group, acridinyl, phenazinyl, benzimidazolyl, benzothiazolyl, benzoxazolyl, indolyl, furyl, thienyl, pyrrolyl, dibenzofuryl, dibenzothienyl, carbazolyl, N-phenylcarbazolyl or the like.

C1-C20 linear or branched alkyl involved in the present disclosure exemplarily includes, but is not limited to, methyl, ethyl, n-propyl, isopropyl, n-butyl, isobutyl, t-butyl, n-pentyl, t-pentyl, isopentyl, neopentyl, n-hexyl, n-heptyl, n-octyl or the like.

In the structure of the organic compound provided by the present disclosure,

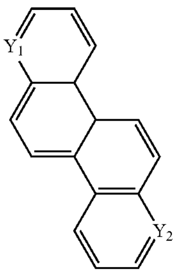

cooperates with the ring A and L cooperates with

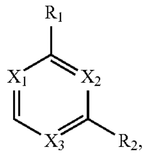

so that the organic compound achieves the purpose of electron transport, has a sufficiently high reduction potential, facilitates electron transport, reduces a potential barrier of electron injection, and further reduces device voltage. The suitable HOMO energy level and LUMO energy level of the organic compound are conducive to energy level matching of adjacent layers. The organic compound has a hole blocking ability due to a relatively deep HOMO energy level so that more holes and electrons are recombined in a light-emitting region, which can achieve higher luminescence efficiency.

An NC group contained in the compound of the present disclosure enhances an electron withdrawing ability of the compound, which means a deeper LUMO energy level, so that the potential barrier of electron injection is reduced, which is conducive to electron injection and reducing device voltage.

The compound of the present disclosure is suitable for use as materials of an electron transport layer and/or a hole blocking layer and can reduce voltage and power consumption, improve the luminescence efficiency, and extend the service life of a device.

In an embodiment, the organic compound has a structure represented by Formula II:

Formula II

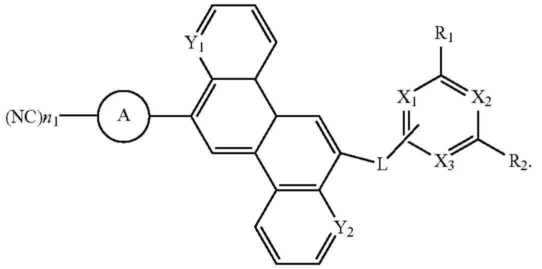

The groups in Formula II are defined within the same ranges as in Formula I.

In an embodiment, when the substituted or unsubstituted C6-C20 aromatic ring, substituted or unsubstituted C5-C30 aromatic heterocycle, substituted or unsubstituted C6-C20 aryl, substituted or unsubstituted C5-C30 heteroaryl, substituted or unsubstituted C6-C30 aryl or substituted or unsubstituted C5-C30 heteroaryl contains a substituent, the substituent is selected from at least one of deuterium, cyano, halogen, unsubstituted or halogenated C1-C10 (for example, C1, C2, C3, C4, C5, C6, C7, C8, C9 or C10) linear or branched alkyl, unsubstituted or halogenated C1-C10 (for example, C1, C2, C3, C4, C5, C6, C7, C8, C9 or C10) alkoxy, C1-C10 (for example, C1, C2, C3, C4, C5, C6, C7, C8, C9 or C10) alkylthio, C6-C20 (for example, C6, C9, C10, C12, C14, C16, C18 or the like) aryl, C5-C20 (for example, C6, C8, C10, C12, C14, C16, C18 or the like) heteroaryl, or C6-C18 (for example, C6, C9, C10, C12, C14, C16, C18 or the like) arylamine.

In an embodiment, the ring A is any one of phenylene, biphenylene, naphthylene, terphenylene, pyridylene and phenylene-naphthylene.

In an embodiment, L is selected from any one of phenylene, biphenylene, naphthylene, terphenylene and pyridylene.

In an embodiment, two of $X_1$ to $X_3$ are N or all of $X_1$ to $X_3$ are N.

In an embodiment, both $Y_1$ and $Y_2$ are selected from the C atom, and $n_1$ is an integer from 1 to 3, for example, 1, 2 or 3.

In an embodiment, at least one of $Y_1$ and $Y_2$ is selected from the N atom, and $n_1$ is an integer from 0 to 3, for example, 0, 1, 2 or 3.

In an embodiment, $R_1$ and $R_2$ are independently selected from any one of the following groups:

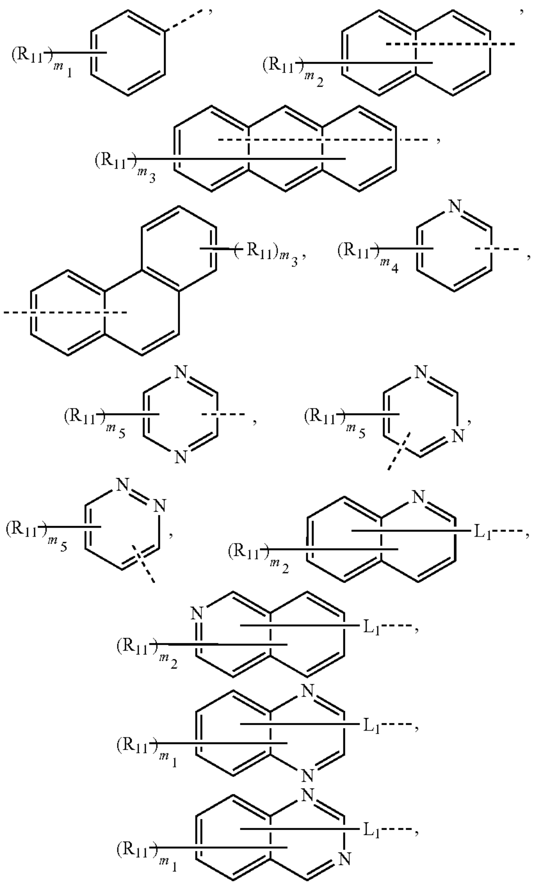

-continued

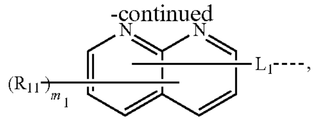,

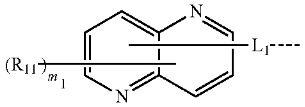,

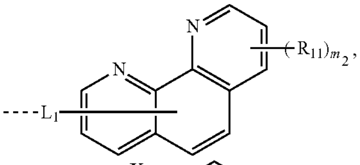,

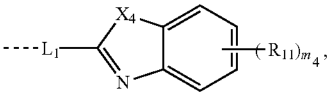,

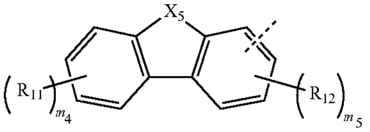, and

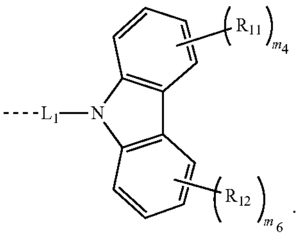.

The dashed line represents a linkage site of the group.

$L_1$ is selected from any one of a single bond or substituted or unsubstituted C6-C20 (for example, C6, C9, C10, C12, C14, C16, C18 or the like) arylene.

$X_4$ is selected from O, S or $NR_{N1}$.

$X_5$ is selected from O, S, $NR_{N2}$ or $CR_{C3}R_{C4}$.

$R_{N1}$, $R_{N2}$, $R_{C3}$ and $R_{C4}$ are each independently selected from any one of hydrogen, substituted or unsubstituted C1-C20 (for example, C2, C3, C4, C5, C6, C8, C10, C12, C14, C16, C18, C19 or the like) linear or branched alkyl, substituted or unsubstituted C6-C20 (for example, C6, C9, C10, C12, C14, C16, C18 or the like) aryl, or substituted or unsubstituted C5-C20 (for example, C6, C8, C10, C12, C14, C16, C18 or the like) heteroaryl.

$R_{11}$ and $R_{12}$ are each independently selected from any one of deuterium, cyano, halogen, unsubstituted or halogenated C1-C10 (for example, C1, C2, C3, C4, C5, C6, C7, C8, C9 or C10) linear or branched alkyl, unsubstituted or halogenated C1-C10 (for example, C1, C2, C3, C4, C5, C6, C7, C8, C9 or C10) alkoxy, C1-C10 (for example, C1, C2, C3, C4, C5, C6, C7, C8, C9 or C10) alkylthio, C6-C20 (for example, C6, C8, C10, C12, C14, C16, C18 or the like) aryl, C5-C20 (for example, C6, C8, C10, C12, C14, C16, C18 or the like) heteroaryl, or C6-C18 arylamine.

$m_1$ is selected from an integer from 0 to 5, for example, may be 0, 1, 2, 3, 4 or 5.

$m_2$ is selected from an integer from 0 to 6, for example, may be 0, 1, 2, 3, 4, 5 or 6.

$m_3$ is selected from an integer from 0 to 9, for example, may be 0, 1, 2, 3, 4, 5, 6, 7, 8 or 9.

$m_4$ and $m_6$ are each independently selected from an integer from 0 to 4, for example, may be 0, 1, 2, 3 or 4.

$m_5$ is selected from an integer from 0 to 3, for example, may be 0, 1, 2 or 3.

In an embodiment, $R_1$ and $R_2$ are independently selected from any one of the following substituted or unsubstituted groups:

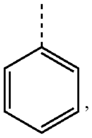, 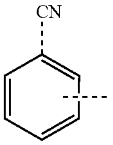, 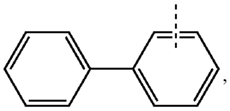,

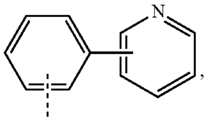, 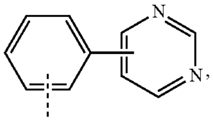,

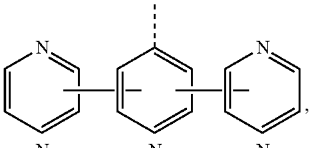,

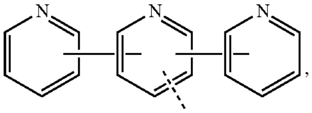,

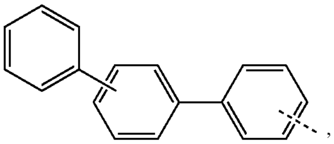,

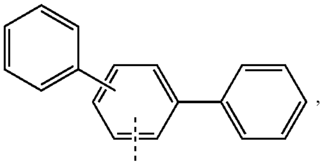, 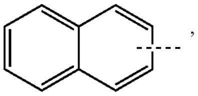,

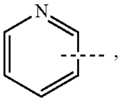, 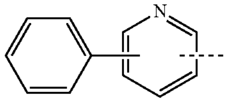,

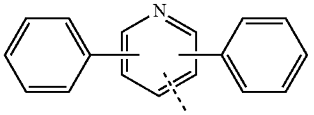, 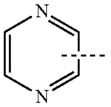,

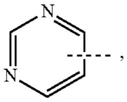, 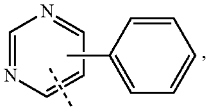,

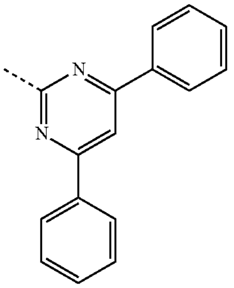, 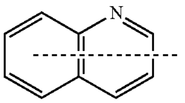,

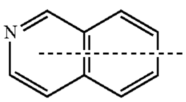, 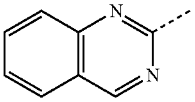,

-continued

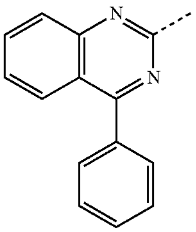,

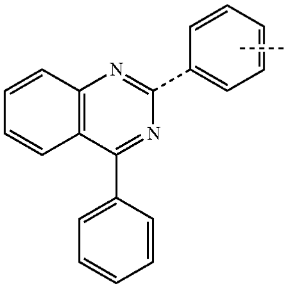,

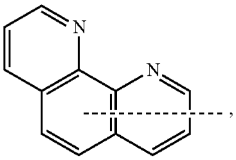,

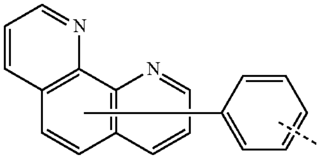,

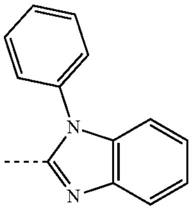,

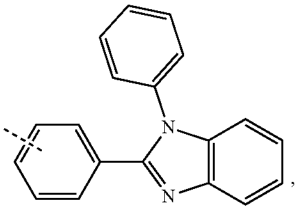,

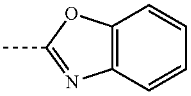,

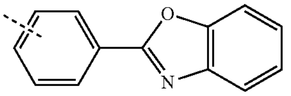,

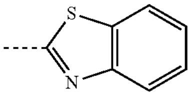,

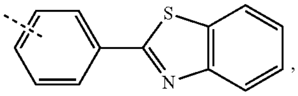,

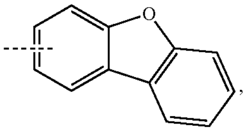,

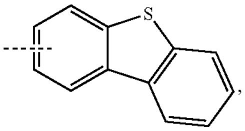,

-continued

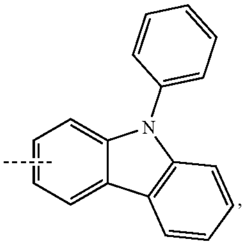,

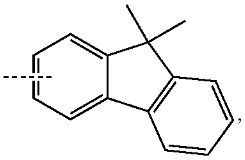,

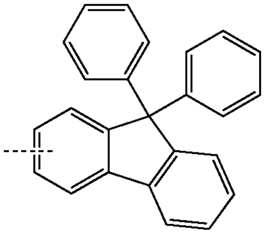,

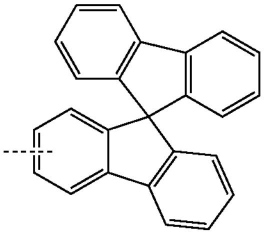, and

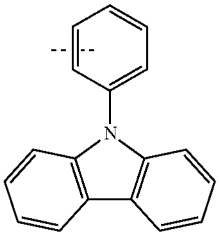.

The dashed line represents a linkage site of the group.

The substituted substituents are each independently selected from at least one of deuterium, cyano, halogen, unsubstituted or halogenated C1-C10 (for example, C1, C2, C3, C4, C5, C6, C7, C8, C9 or C10) linear or branched alkyl, unsubstituted or halogenated C1-C10 (for example, C1, C2, C3, C4, C5, C6, C7, C8, C9 or C10) alkoxy, C1-C10 (for example, C1, C2, C3, C4, C5, C6, C7, C8, C9 or C10) alkylthio, C6-C20 (for example, C6, C9, C10, C12, C14, C16, C18 or the like) aryl, C5-C20 (for example, C6, C9, C10, C12, C14, C16, C18 or the like) heteroaryl, or C6-C18 (for example, C6, C9, C10, C12, C14, C16, C18 or the like) arylamine.

In an embodiment, the organic compound is selected from any one of the following compounds:

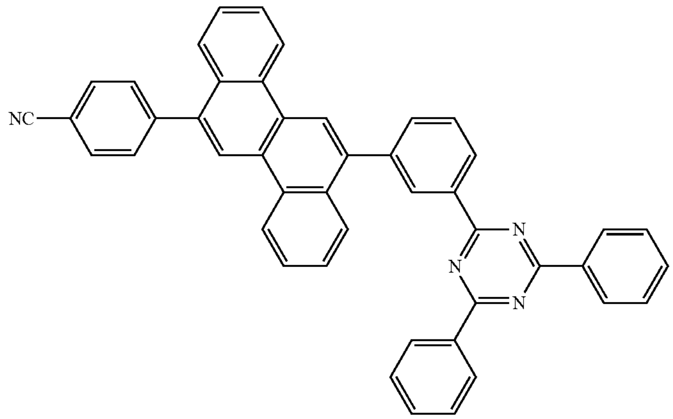
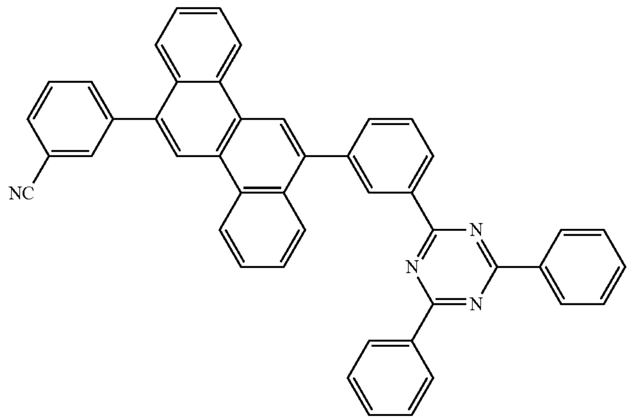
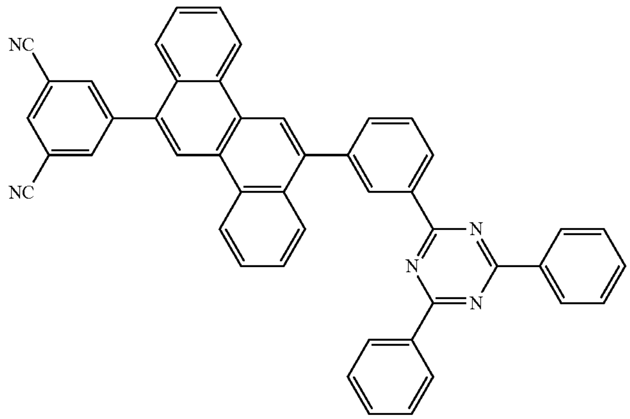
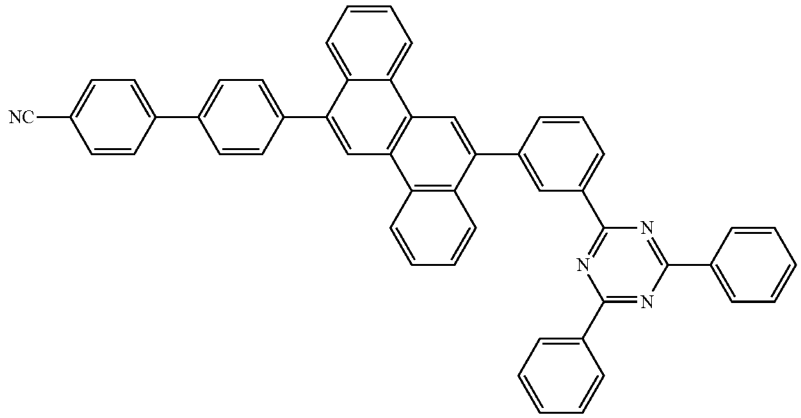

-continued
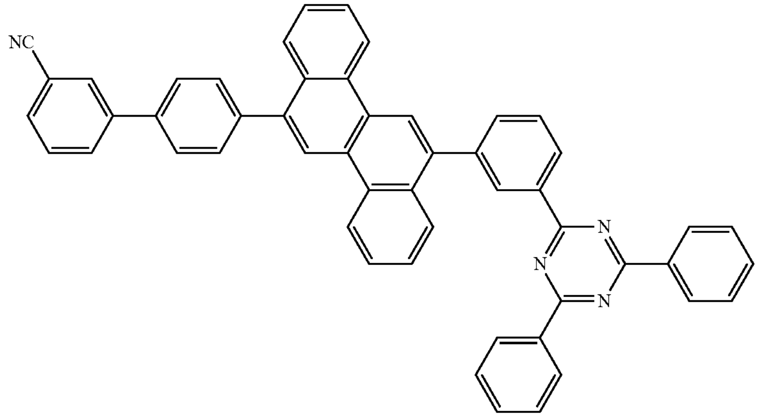
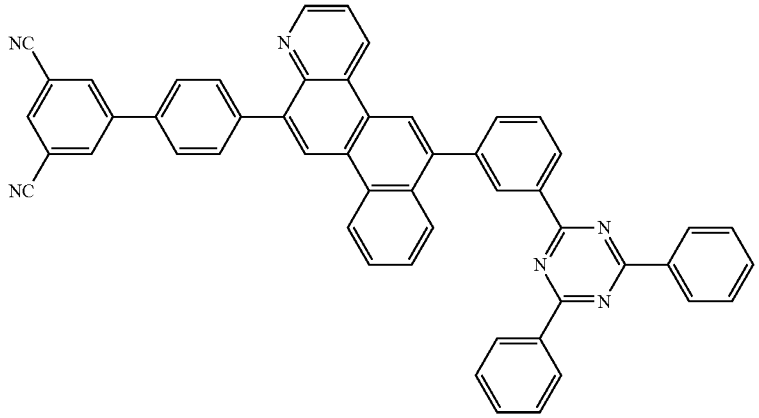
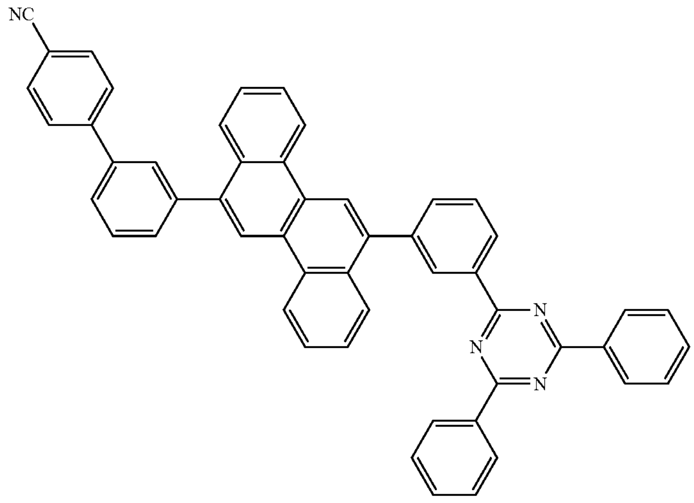

-continued
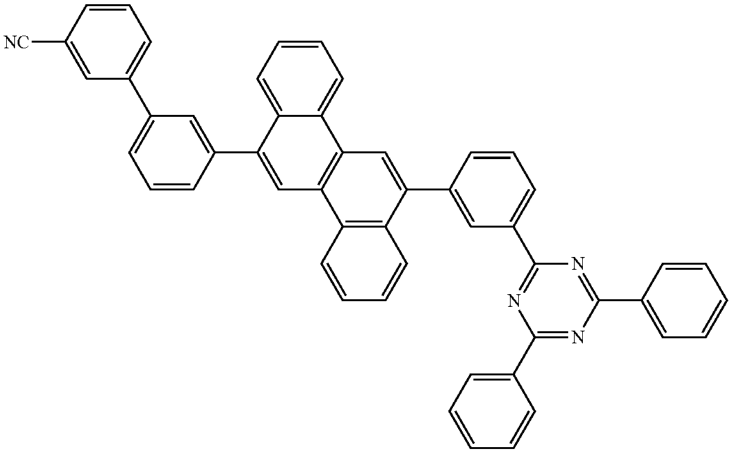
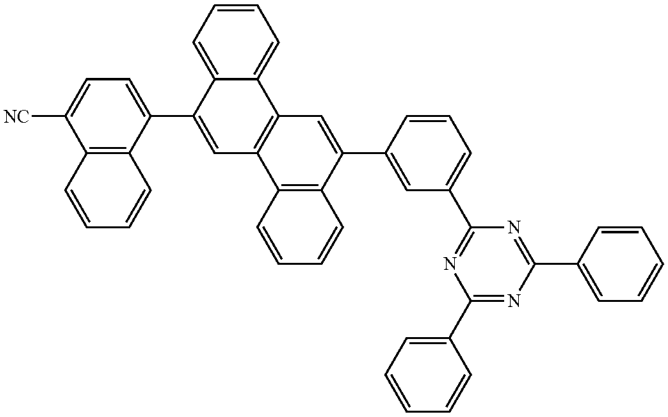
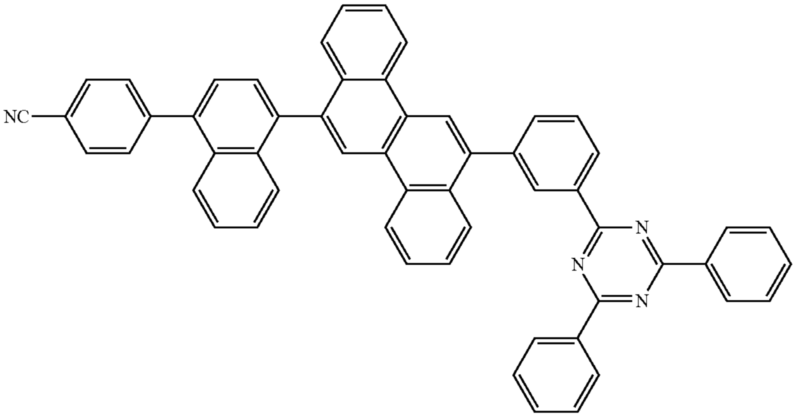
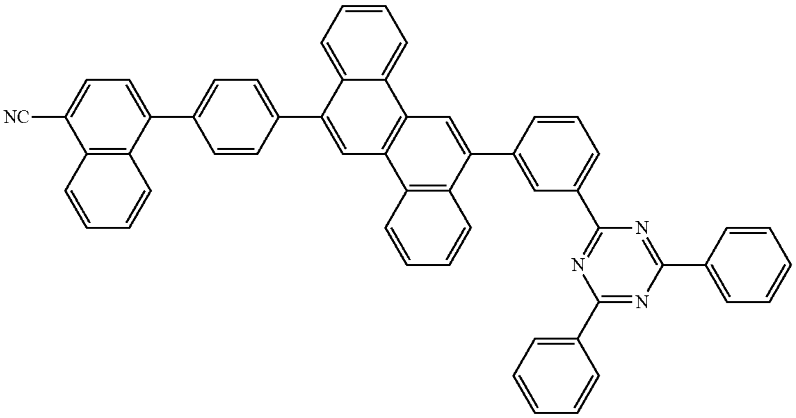

-continued
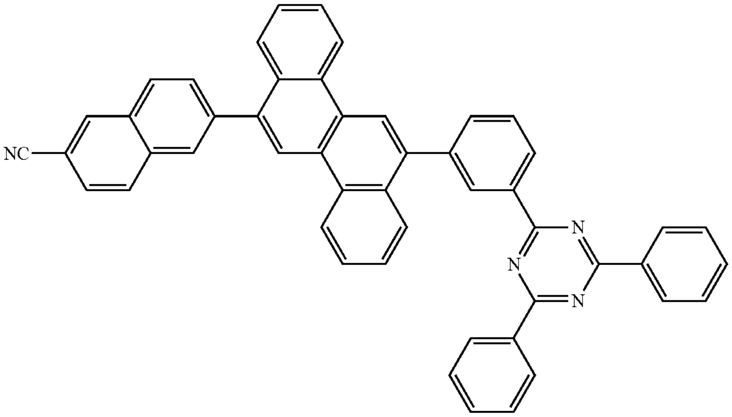
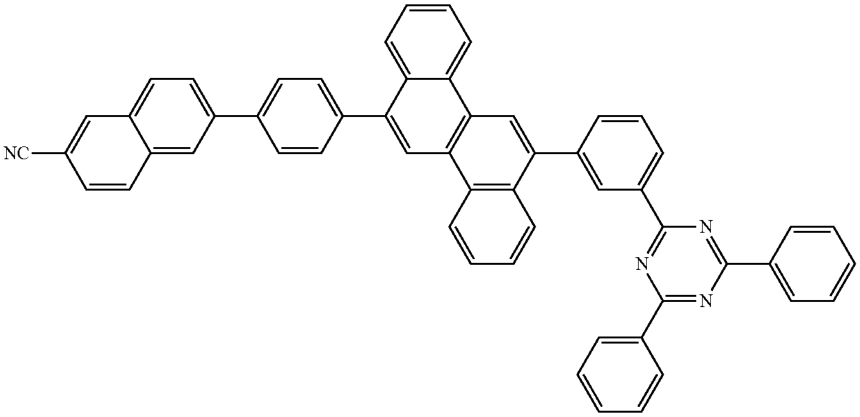
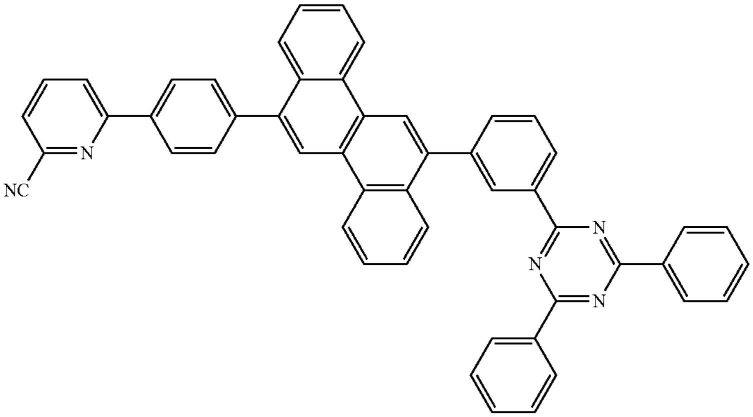

-continued
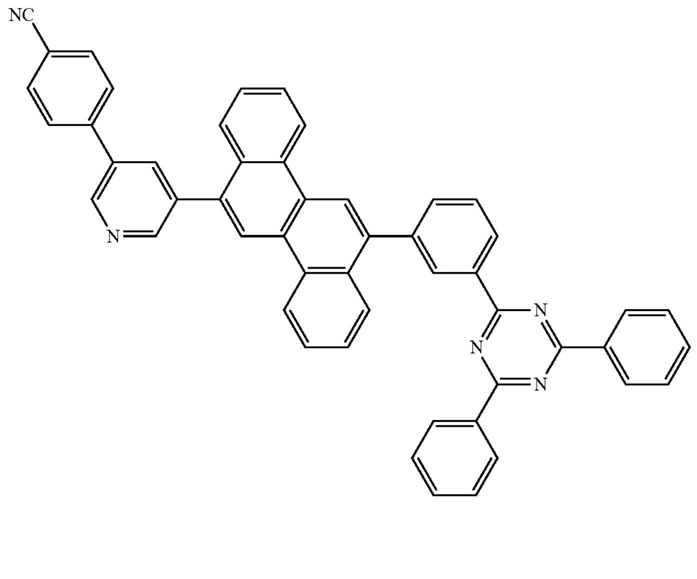
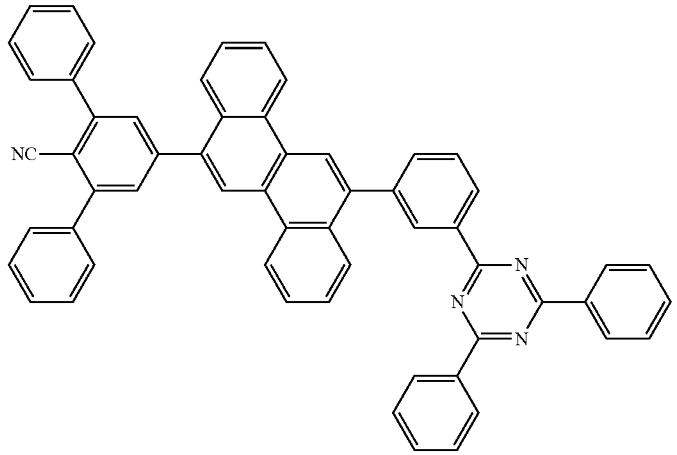
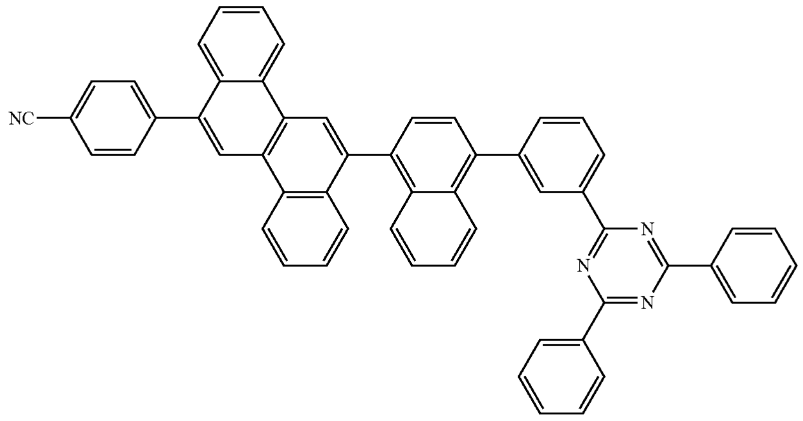

-continued
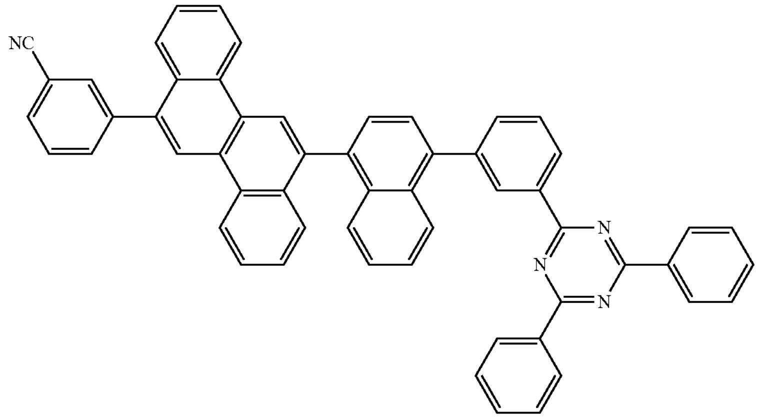
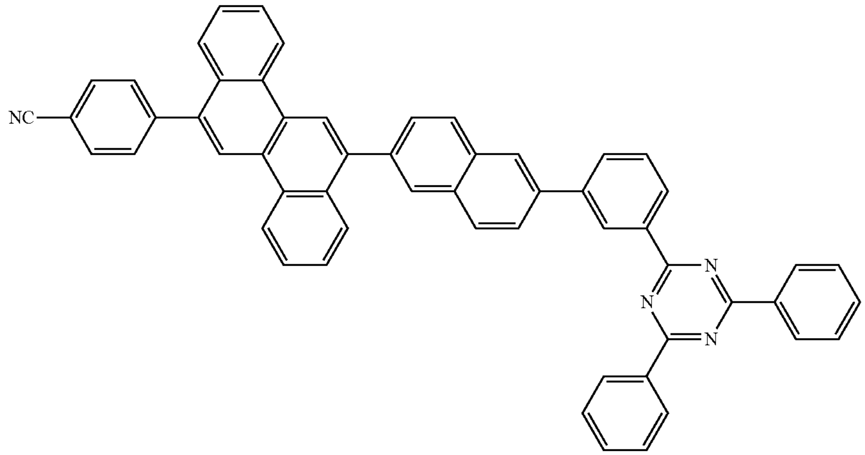
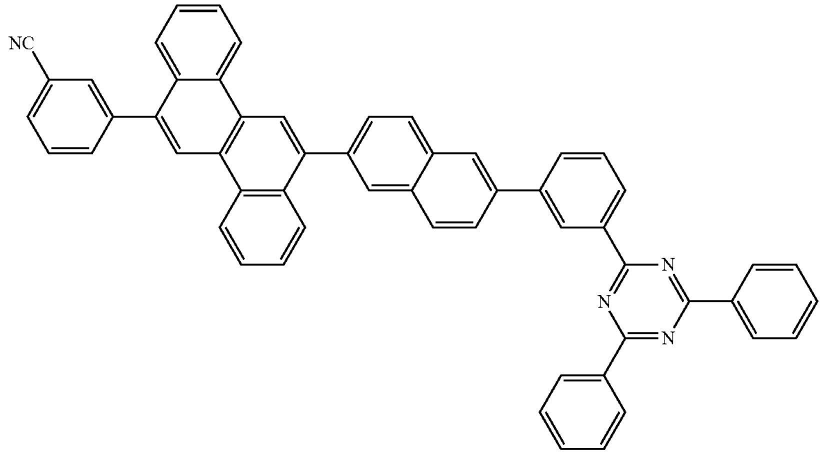
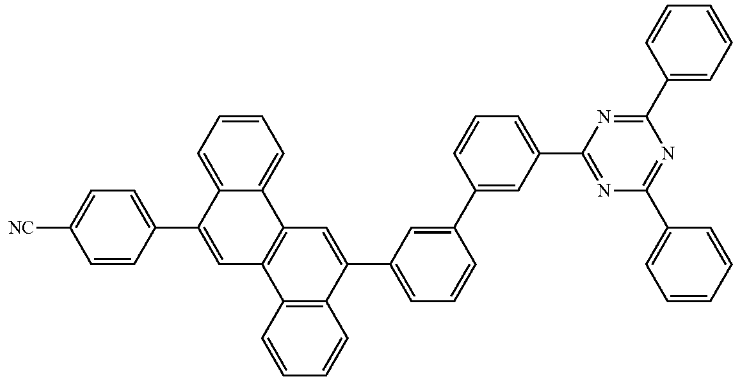

-continued
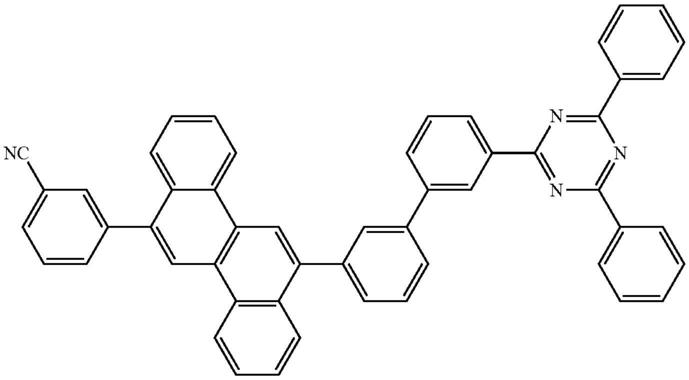
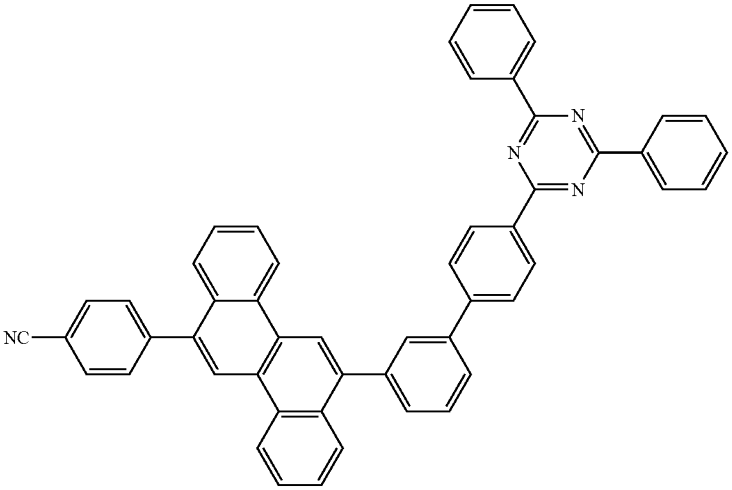
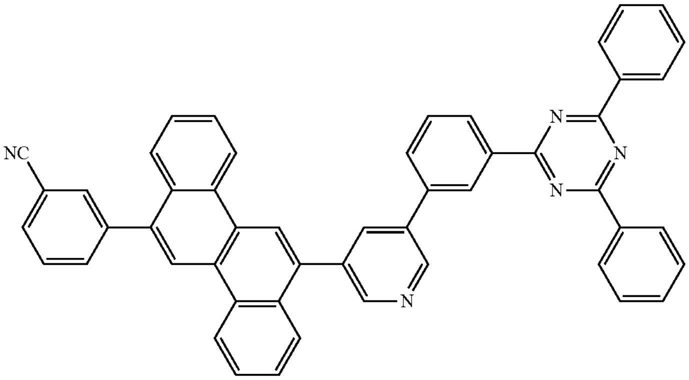
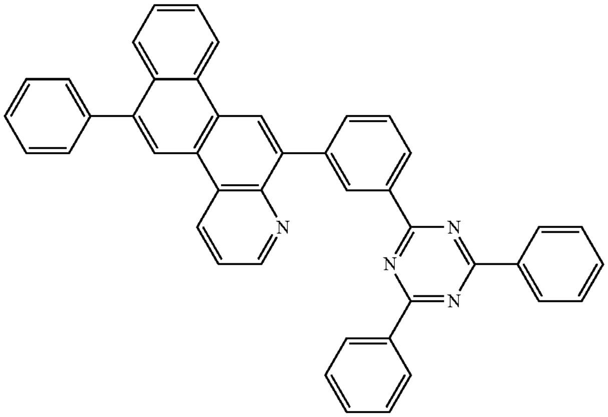

-continued
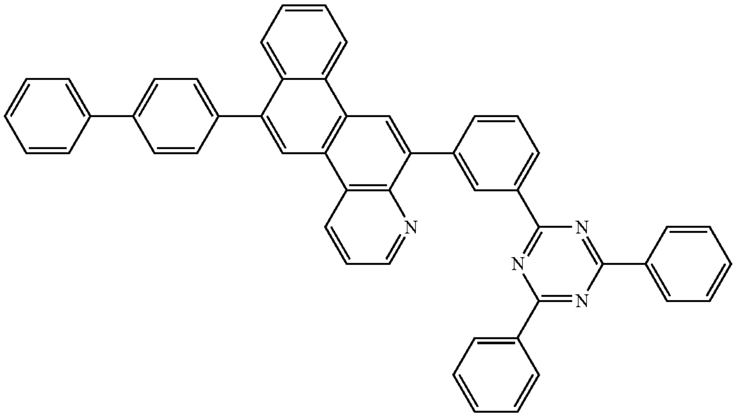
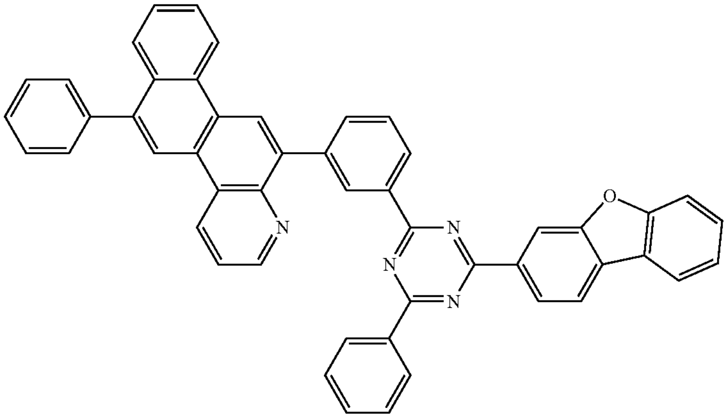
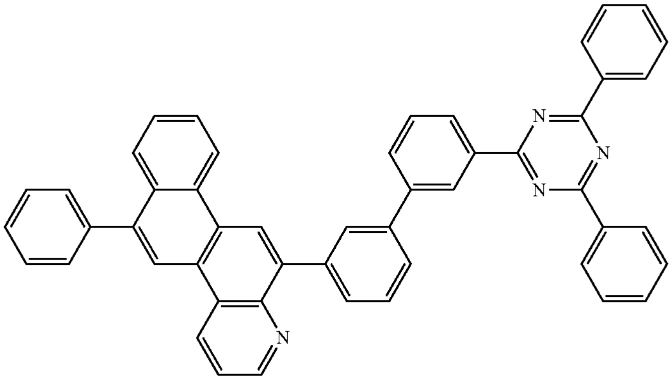
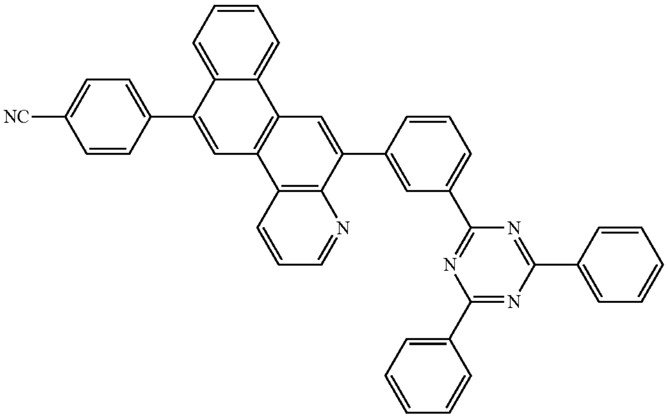

-continued
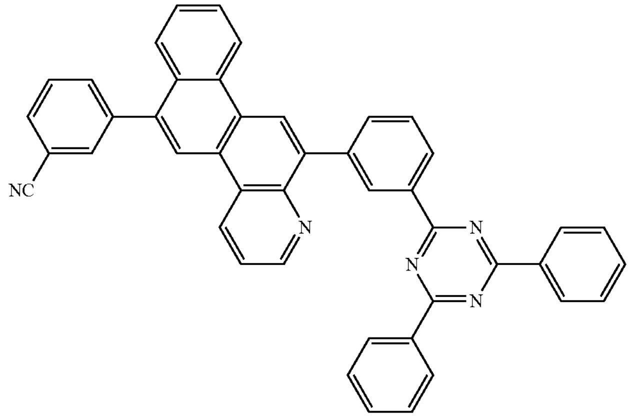
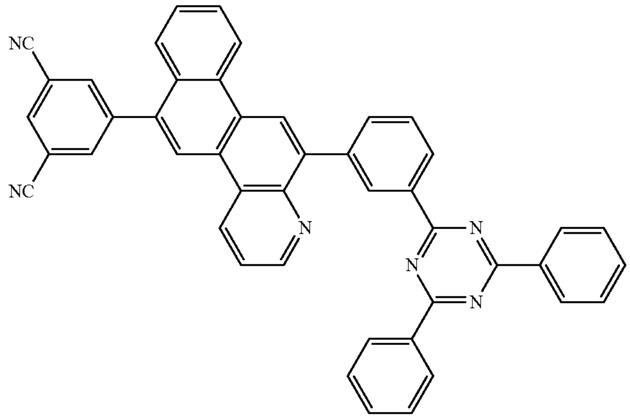
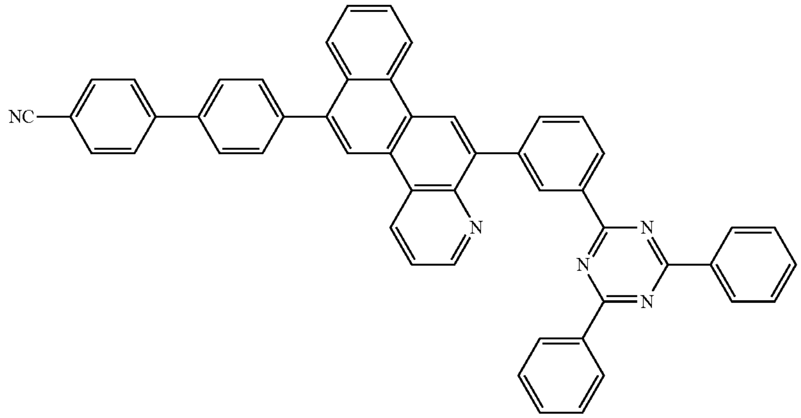
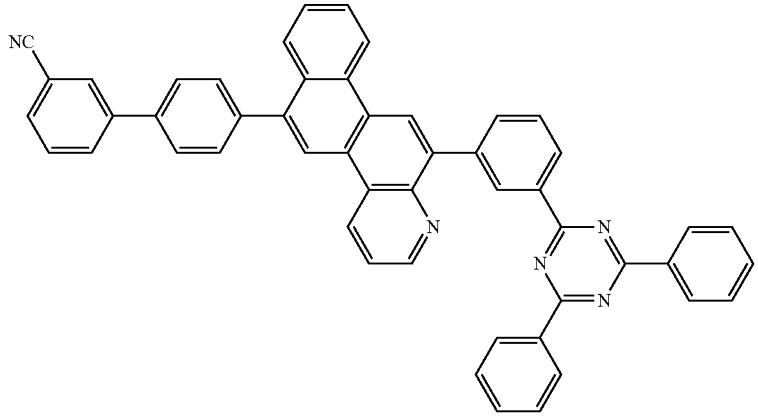

-continued
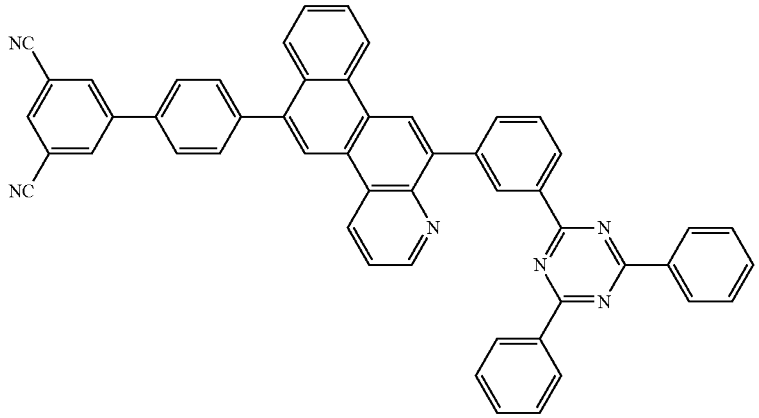
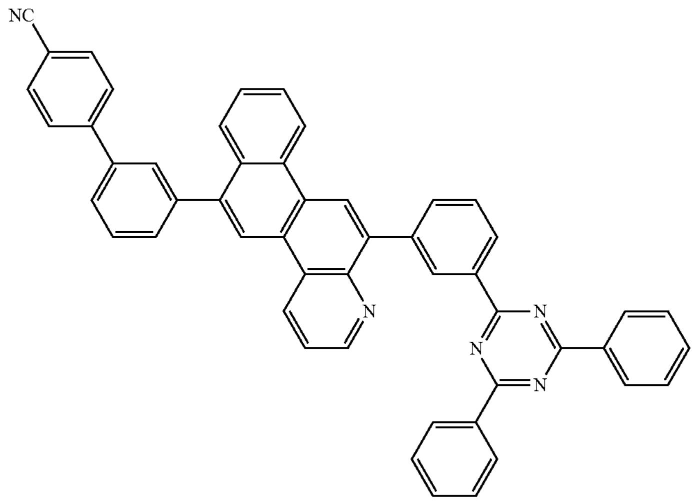
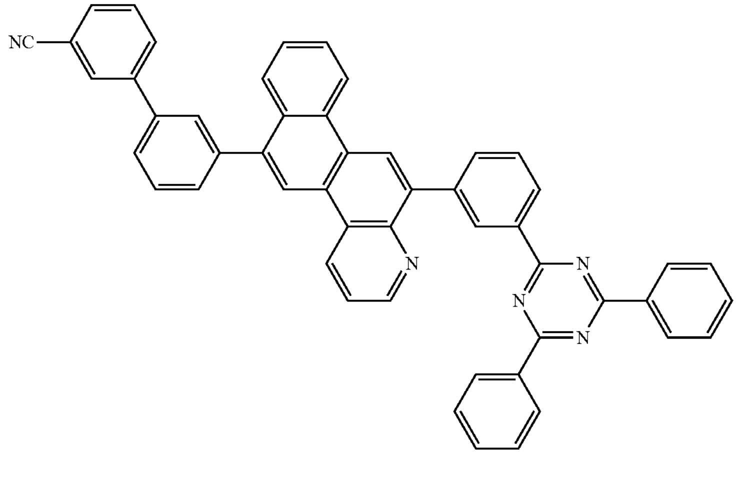

-continued
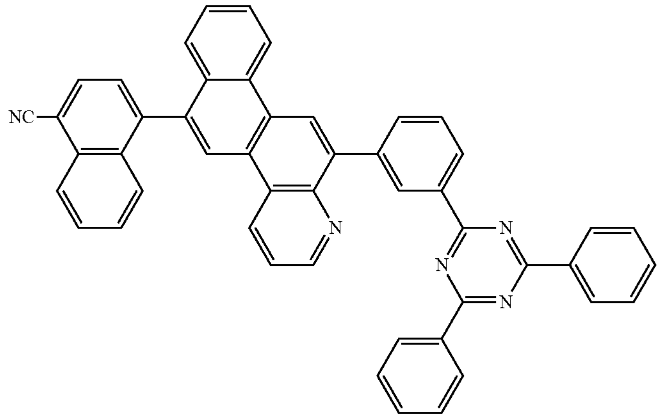
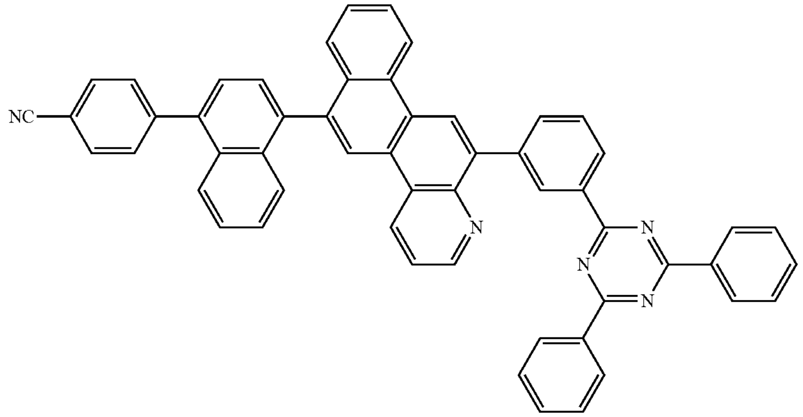
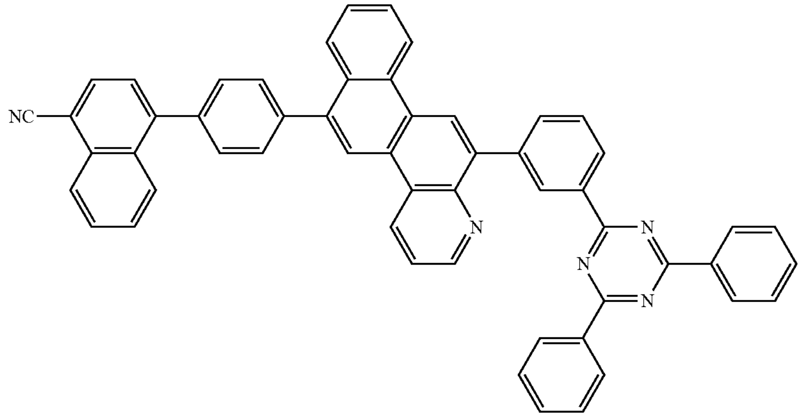
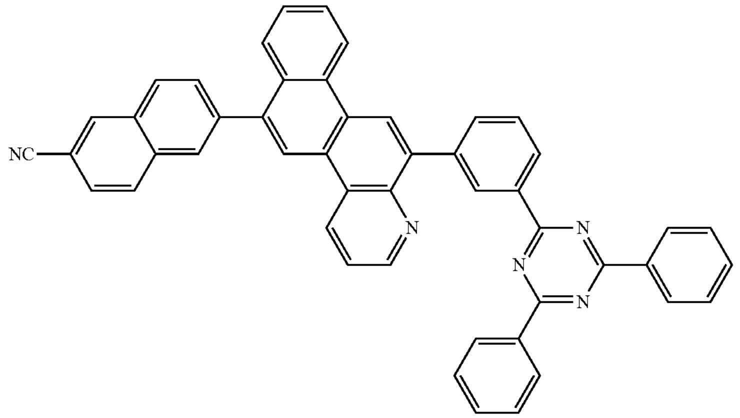

-continued
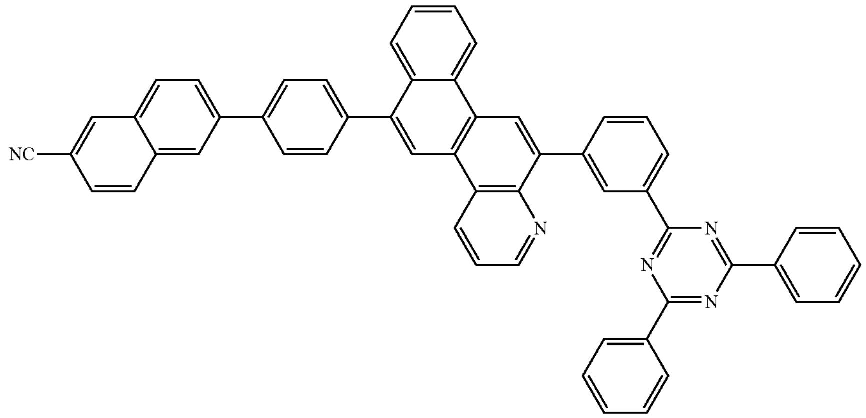
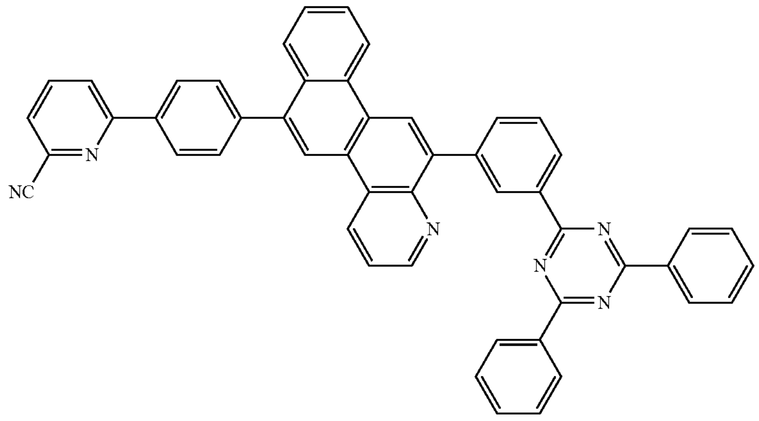
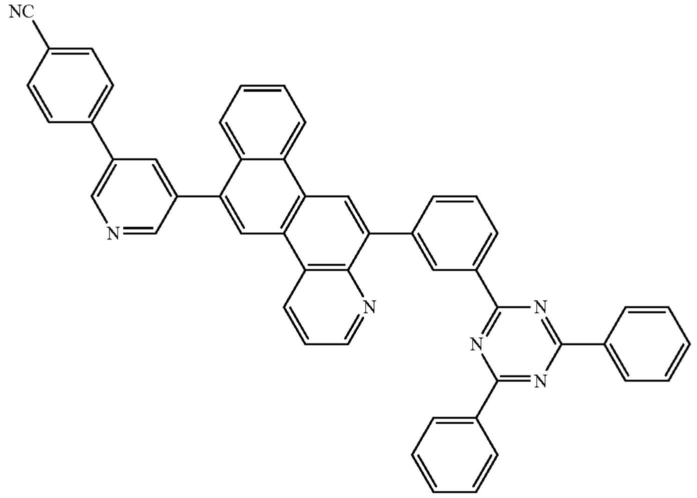

-continued
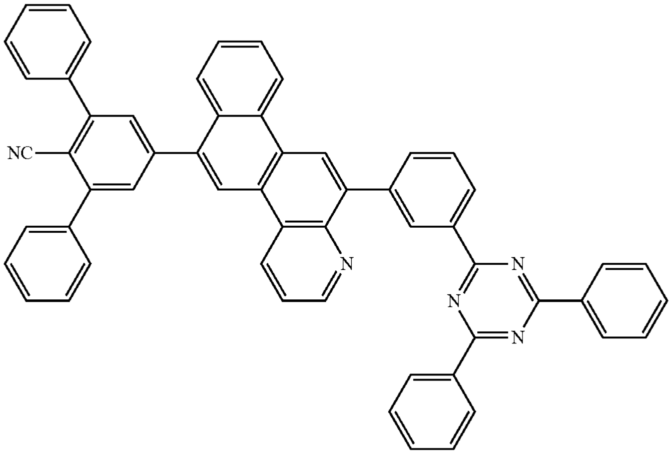
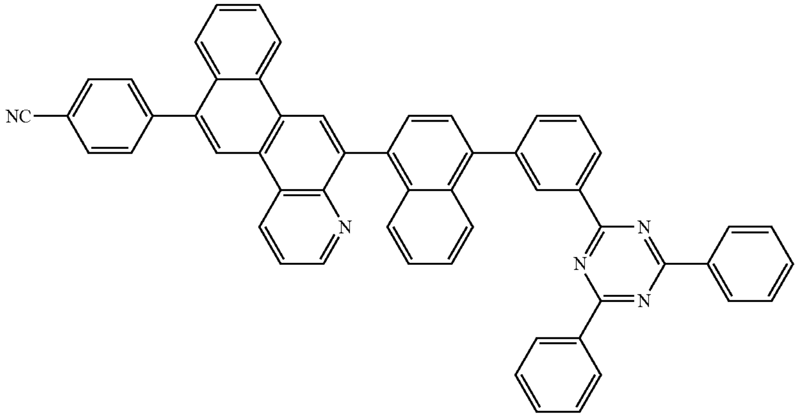
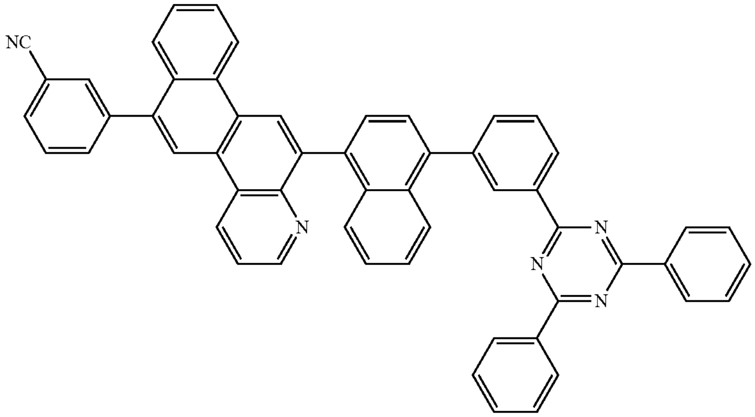

-continued
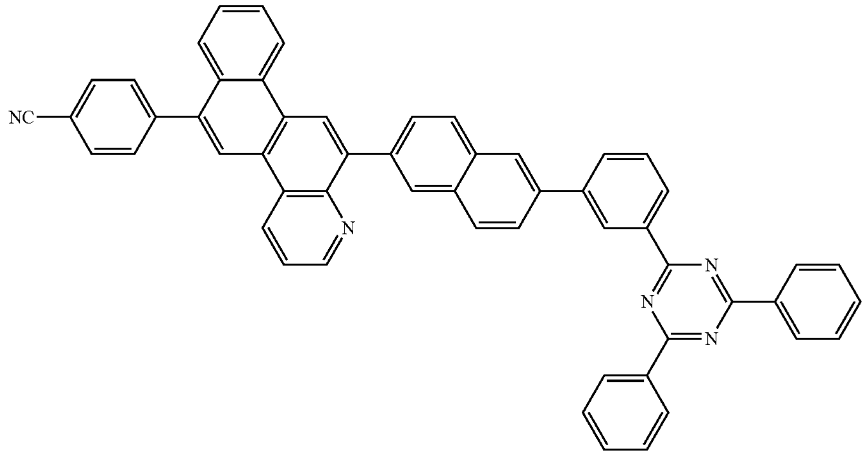
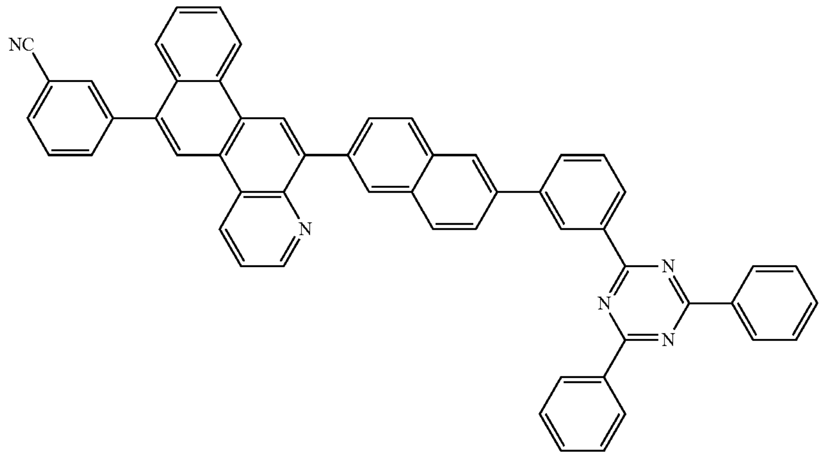
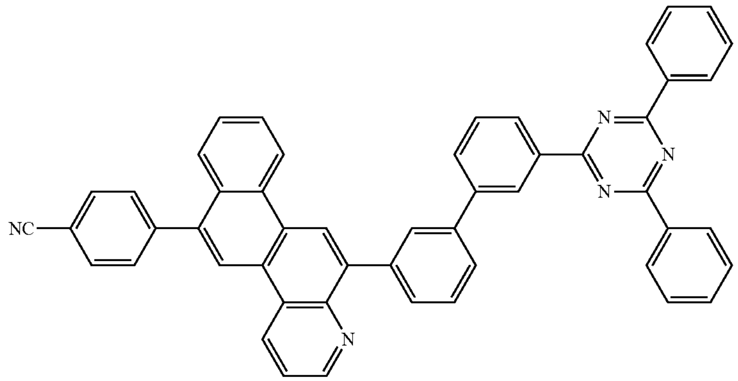
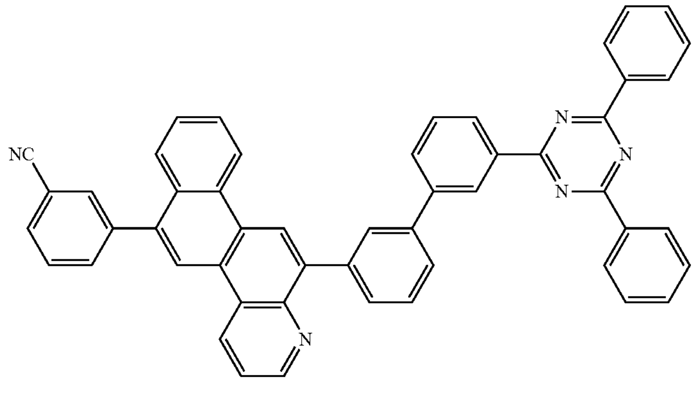

-continued
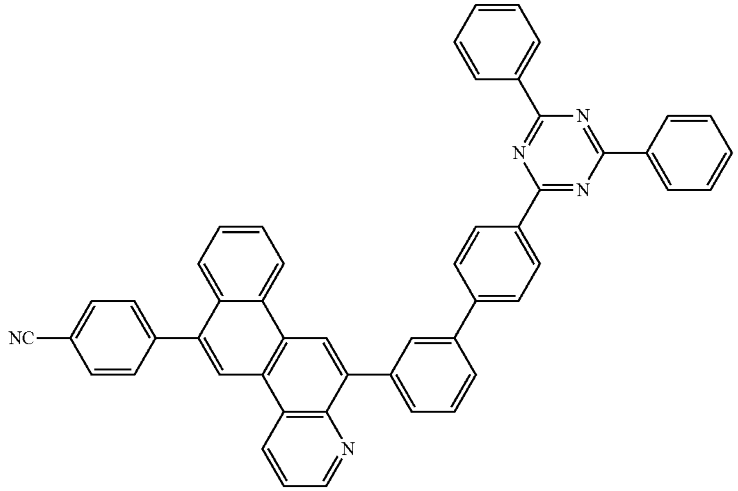
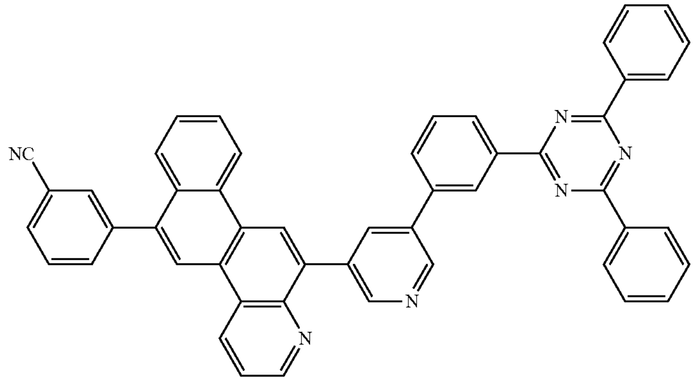
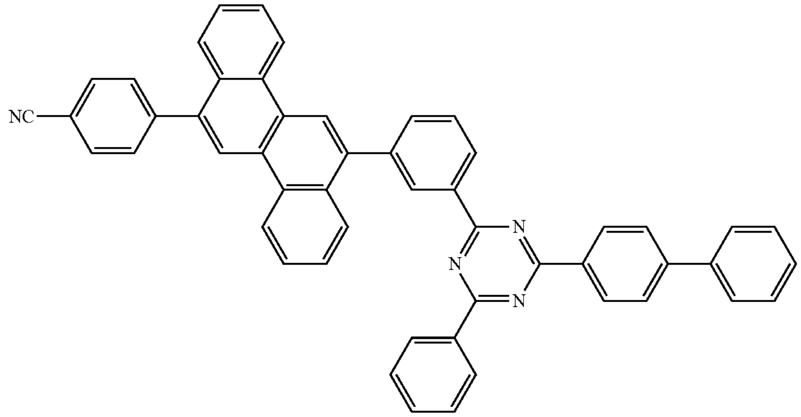
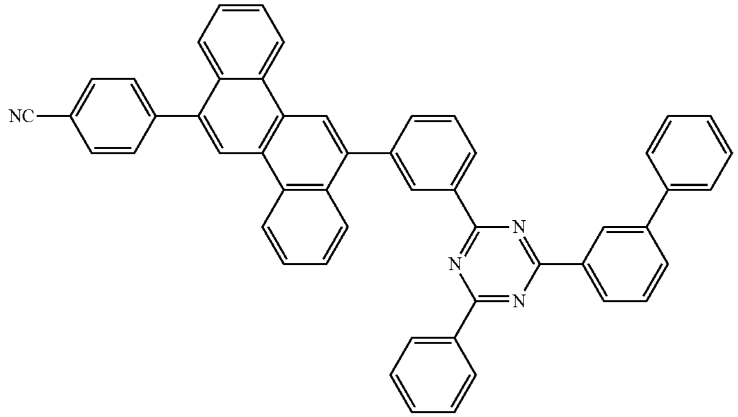

-continued
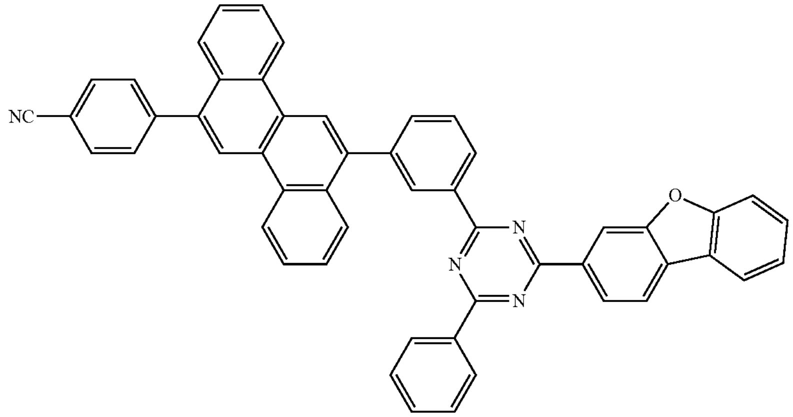
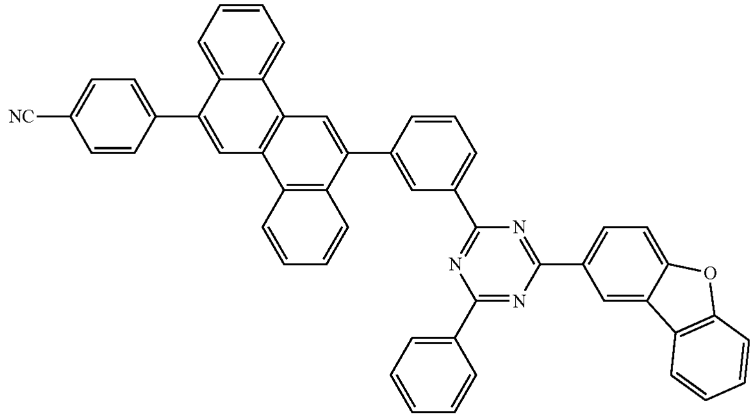
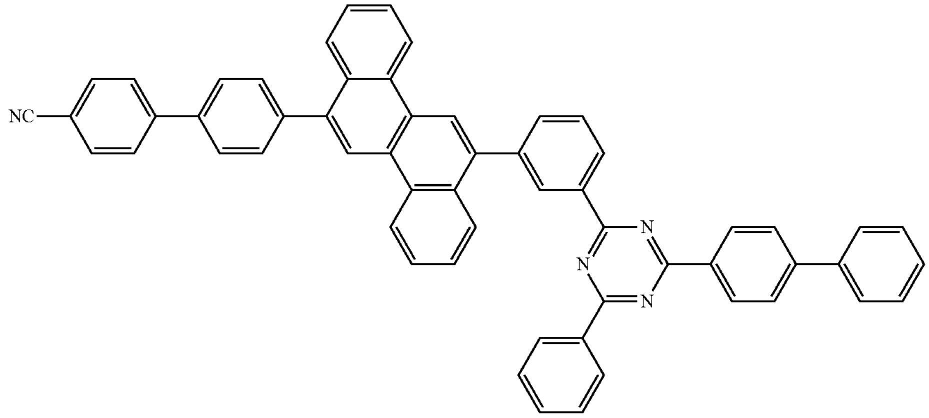
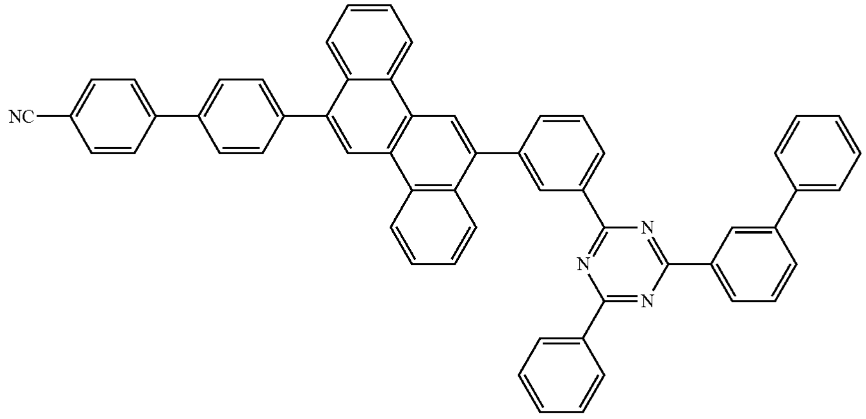

-continued
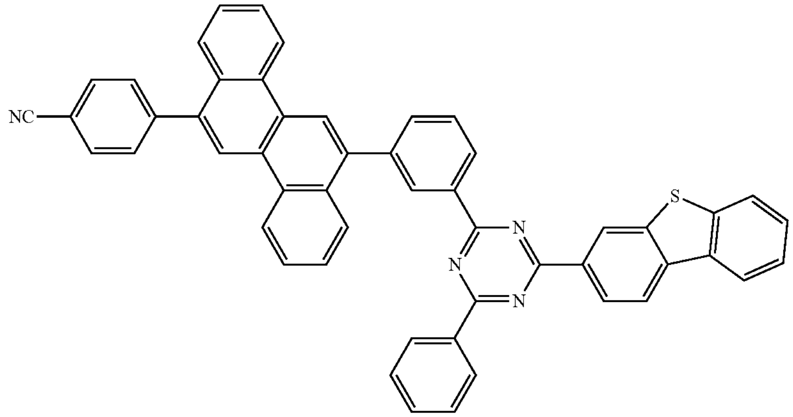
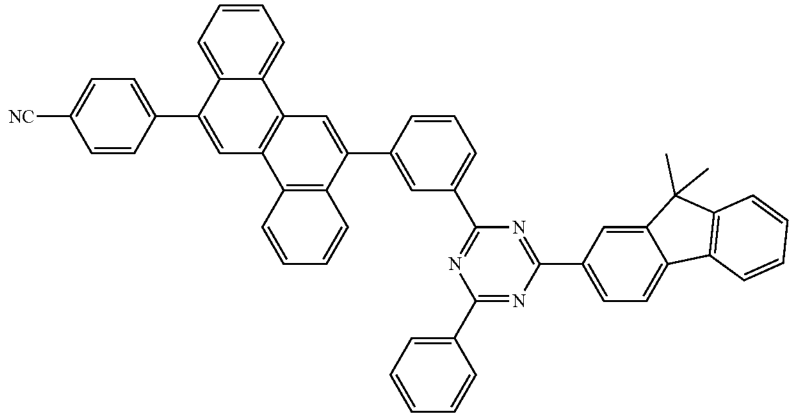
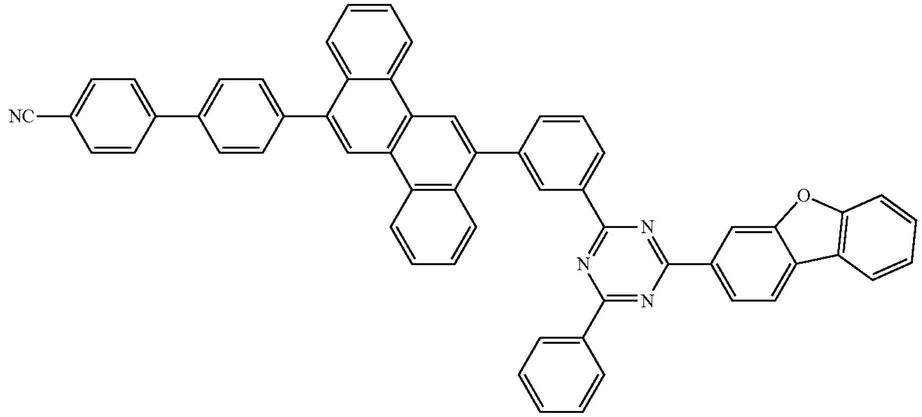
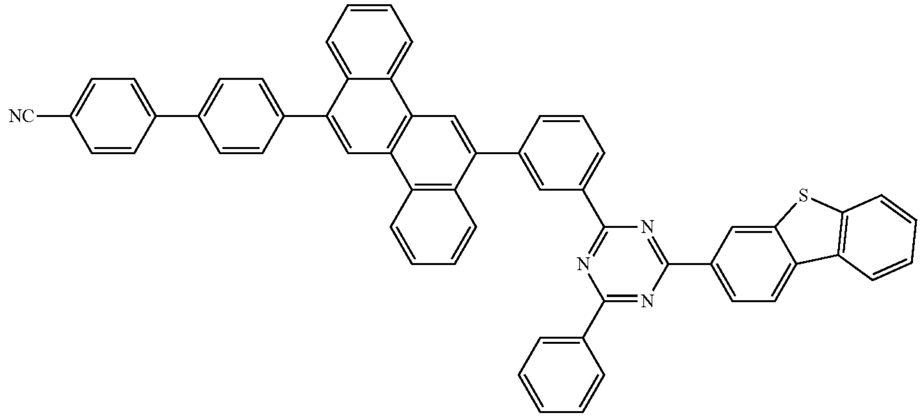

-continued
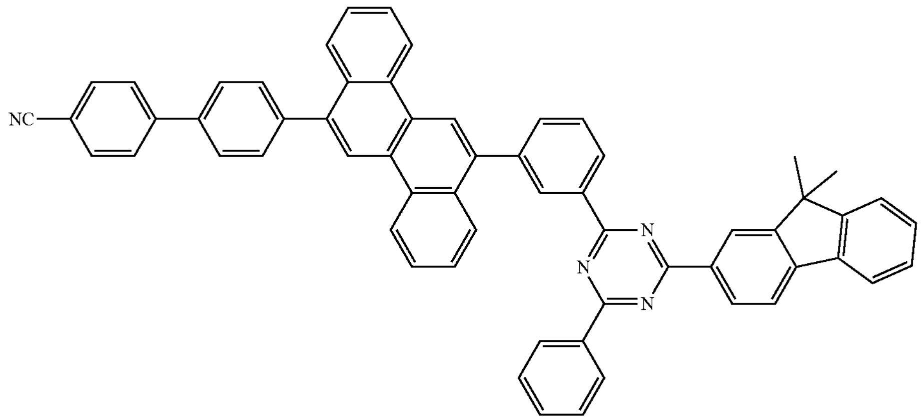
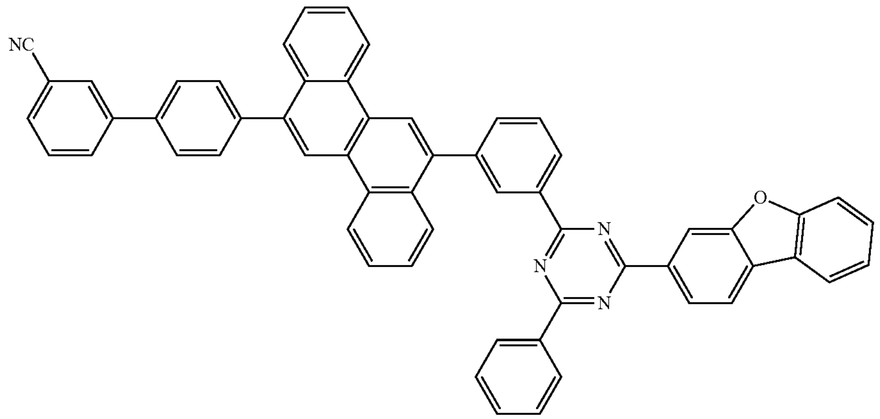
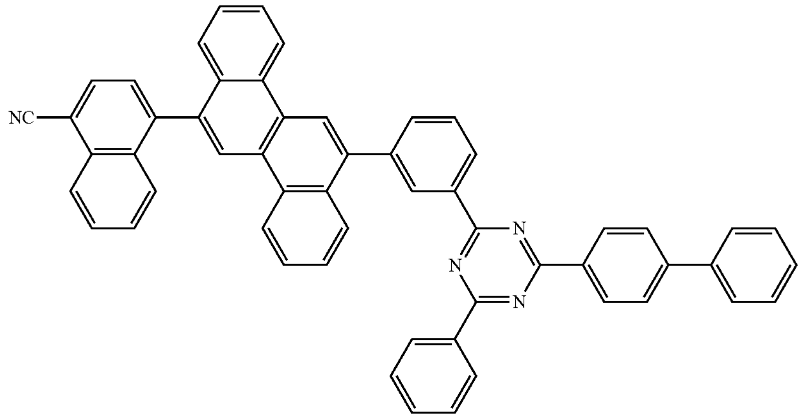
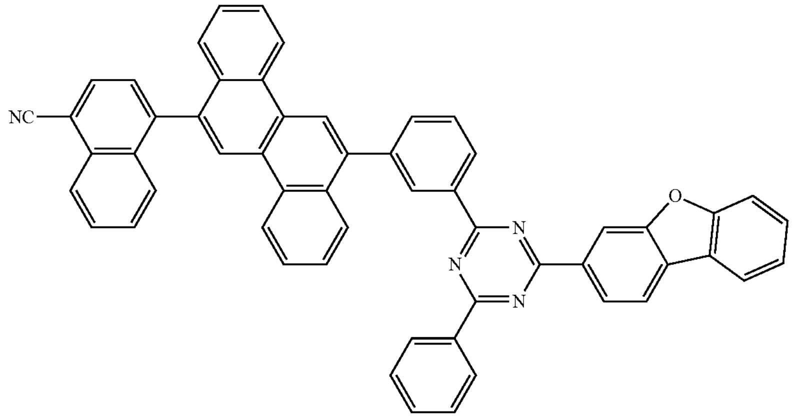

-continued
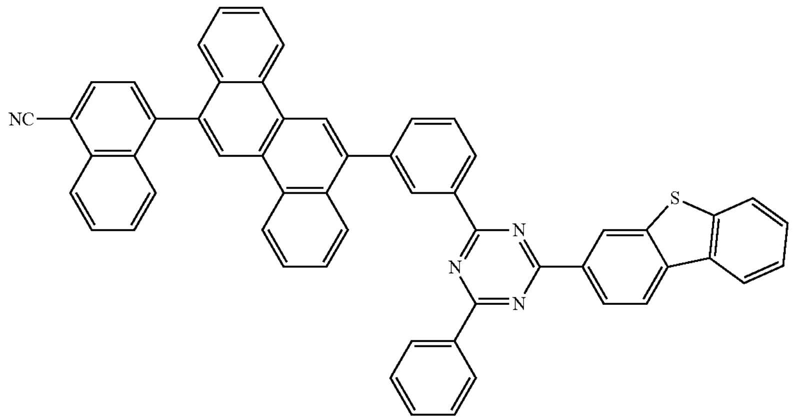
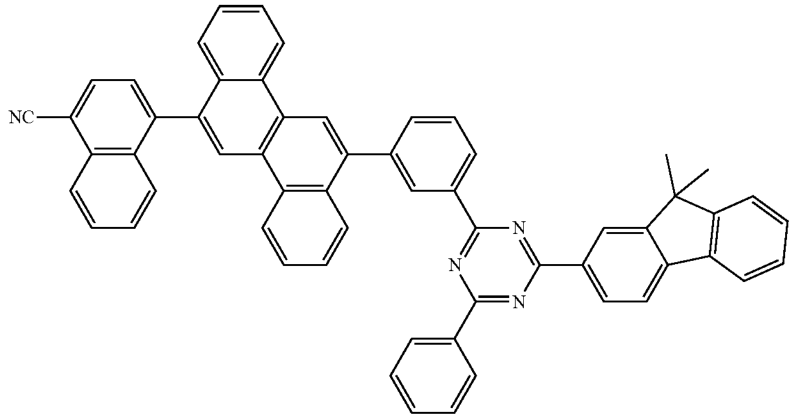
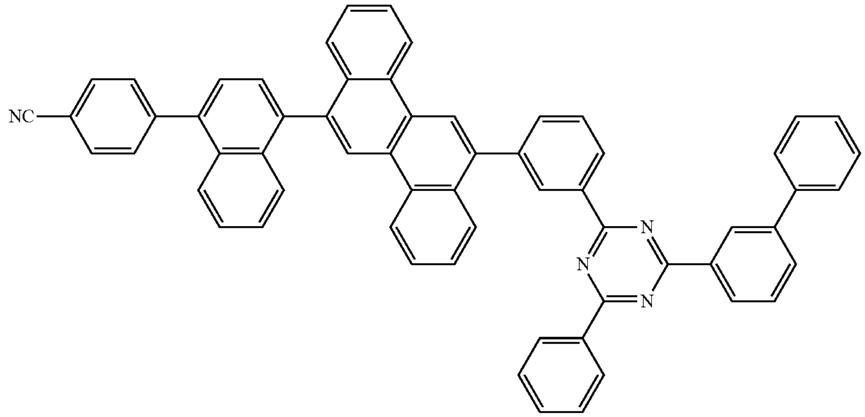
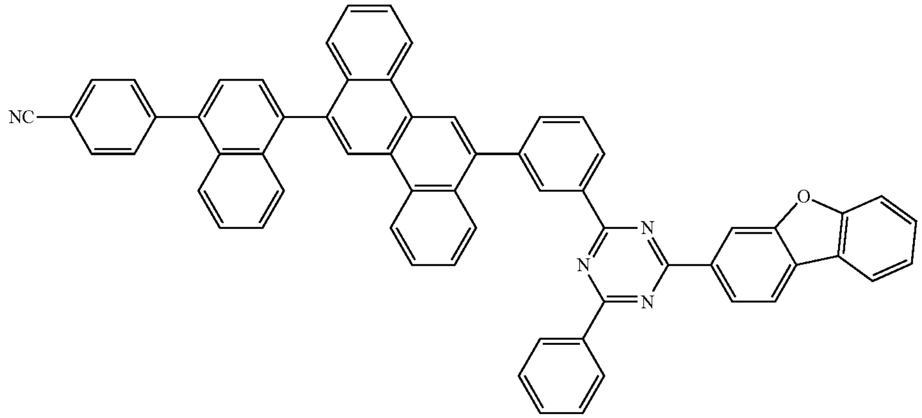

-continued
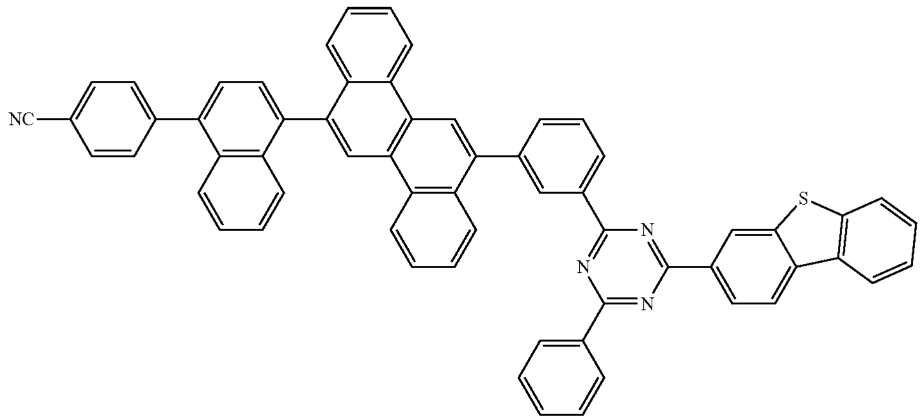
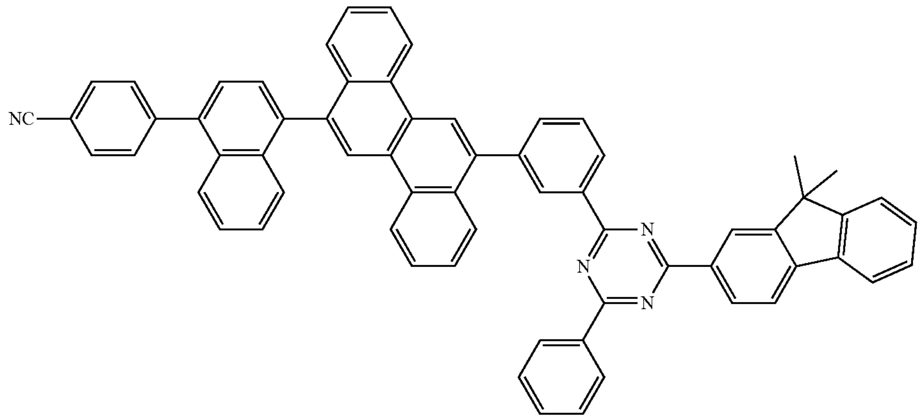
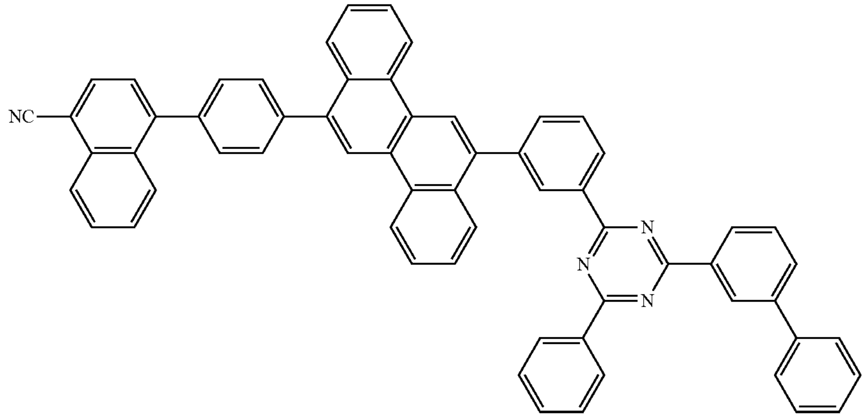
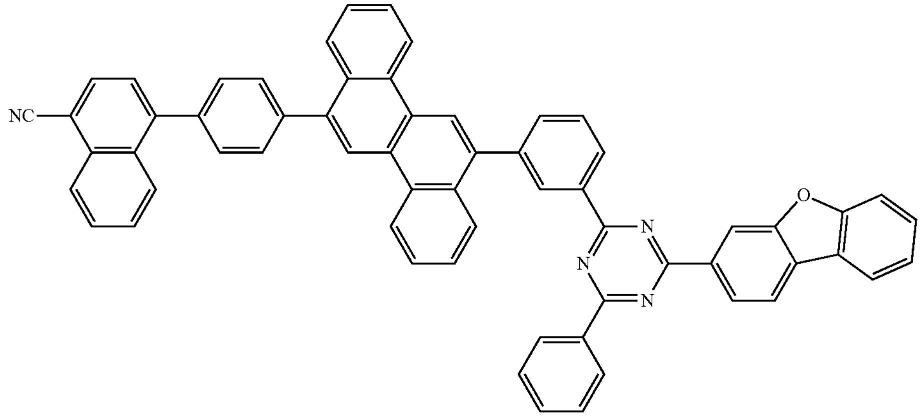

-continued
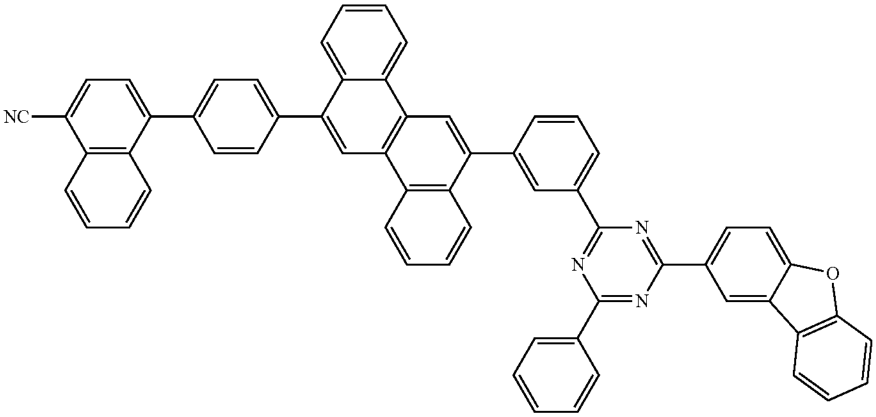
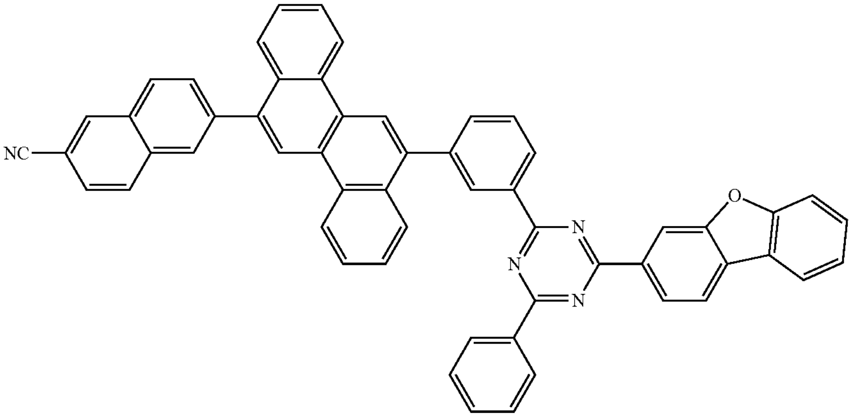
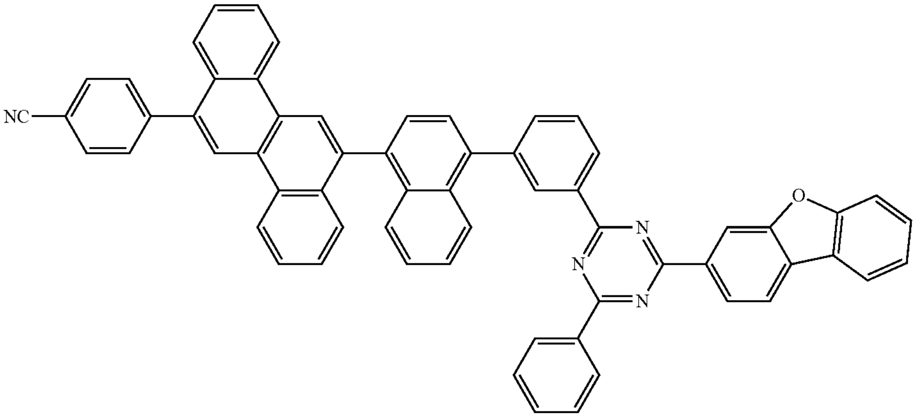
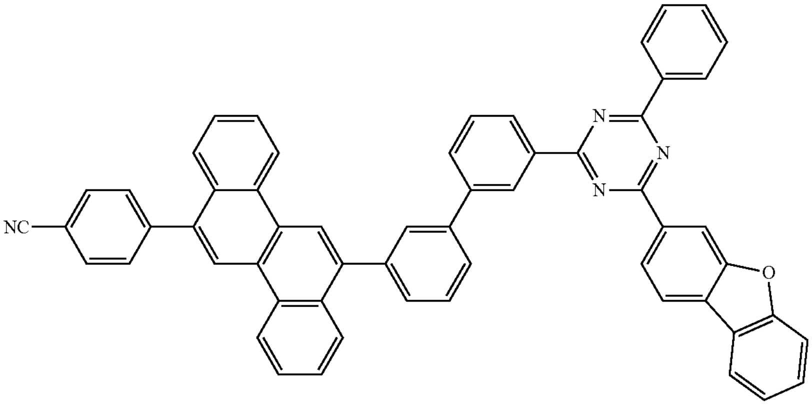

-continued
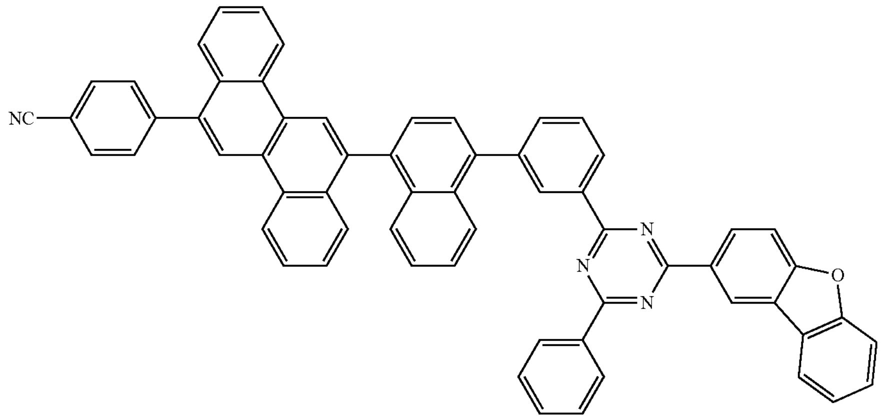
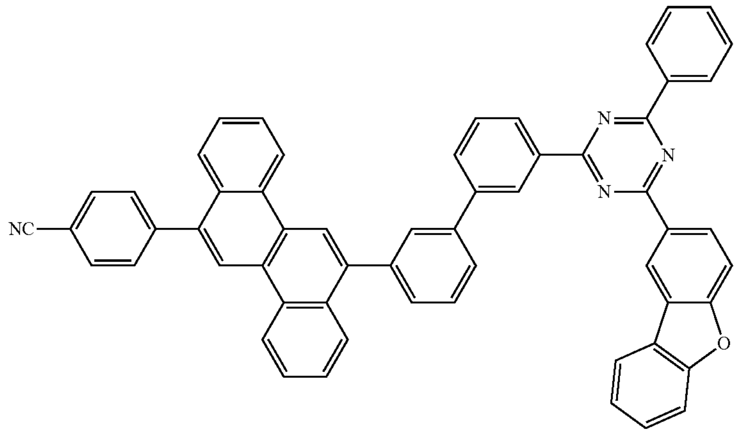
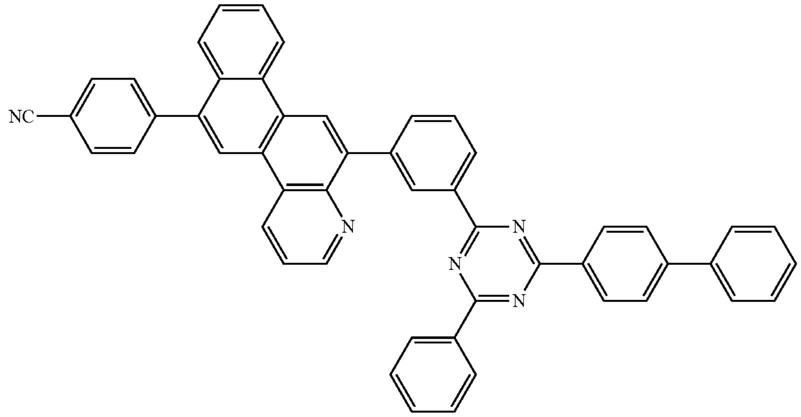
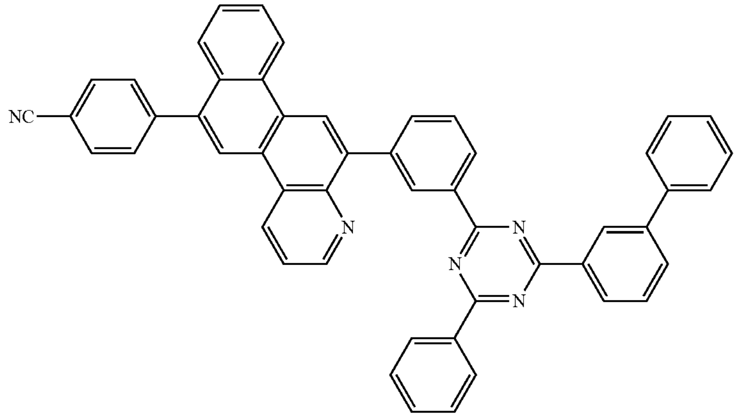

-continued
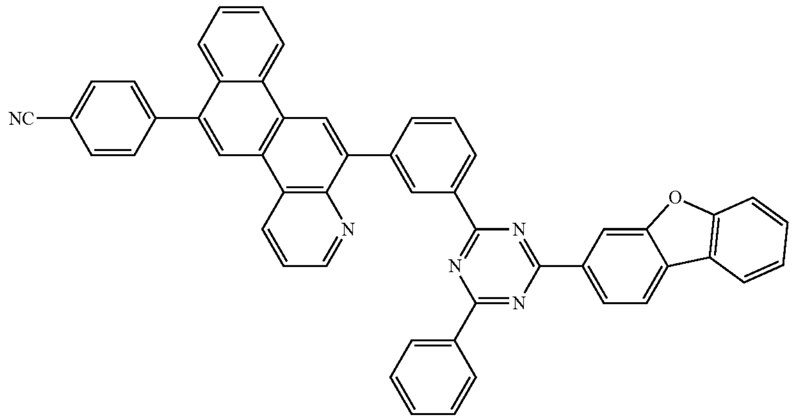
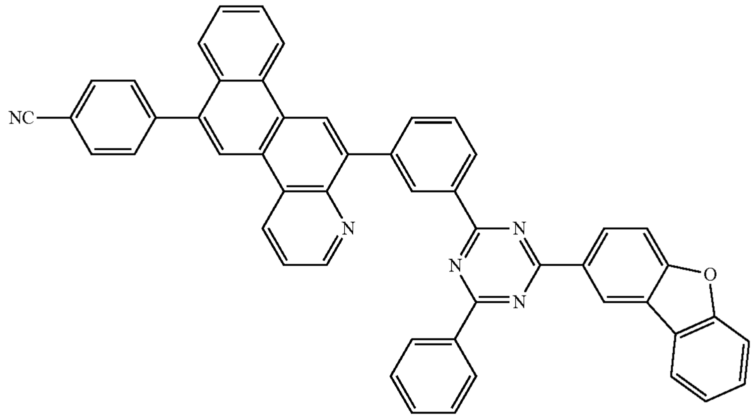
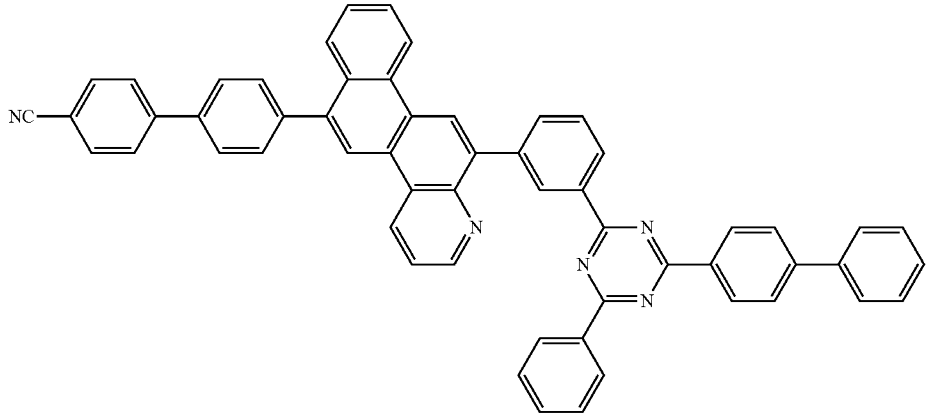
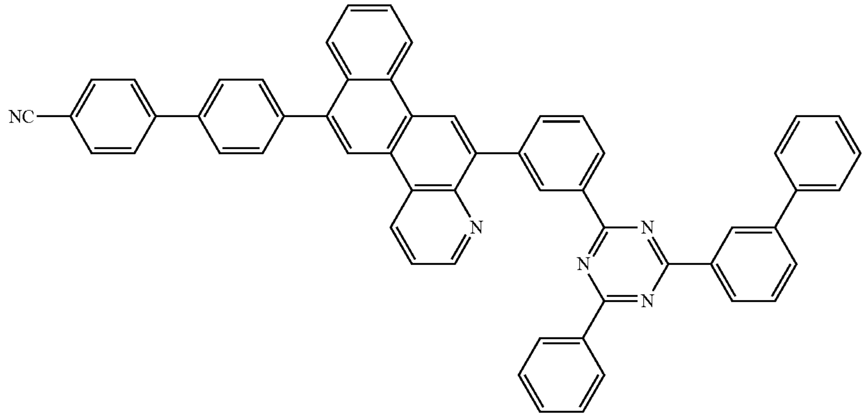

-continued
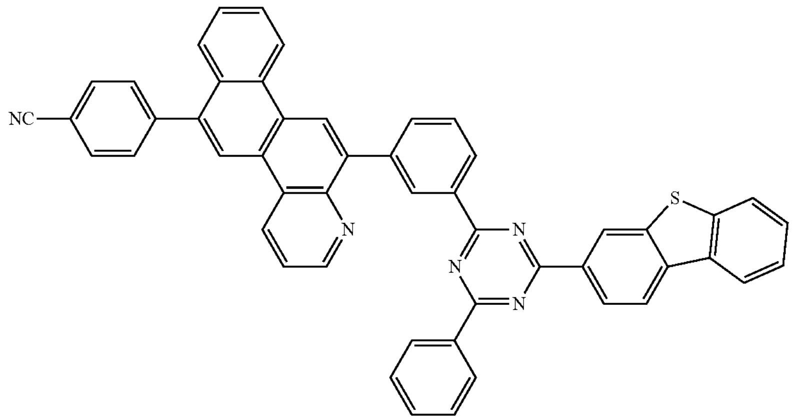
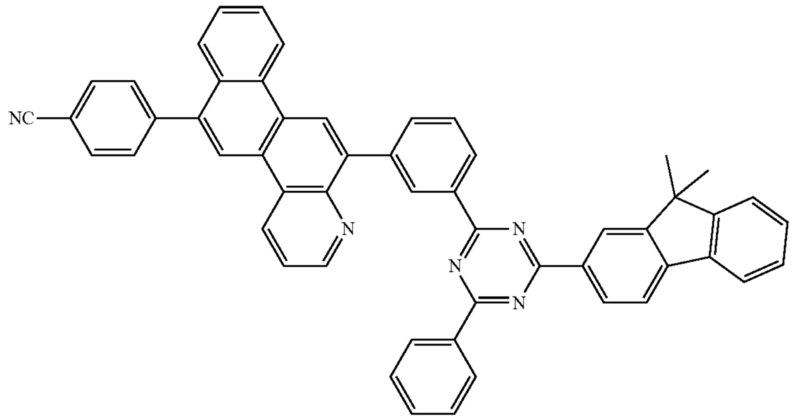
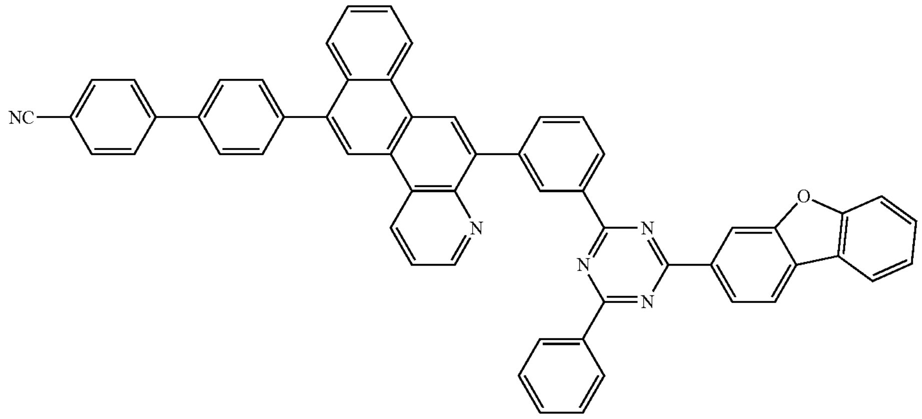
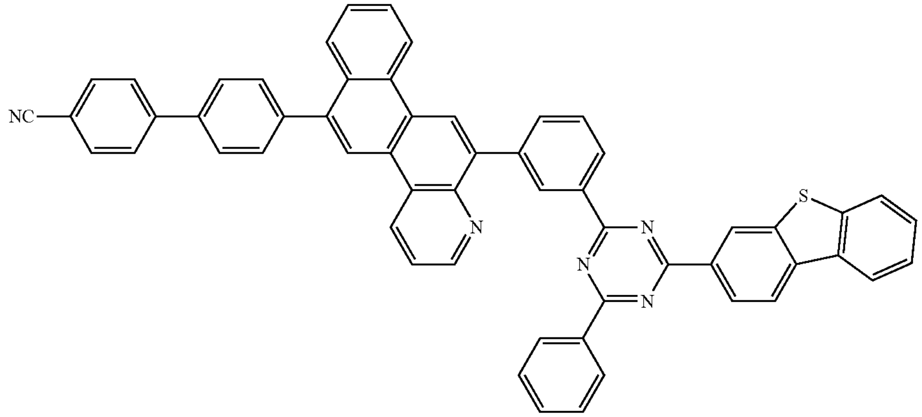

-continued
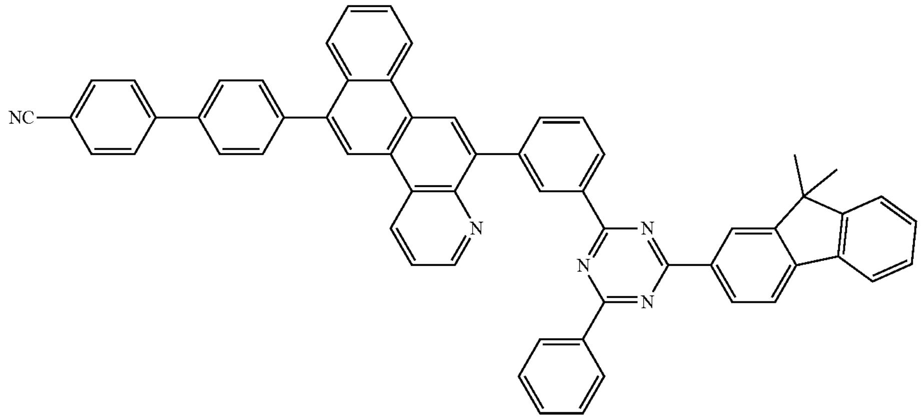
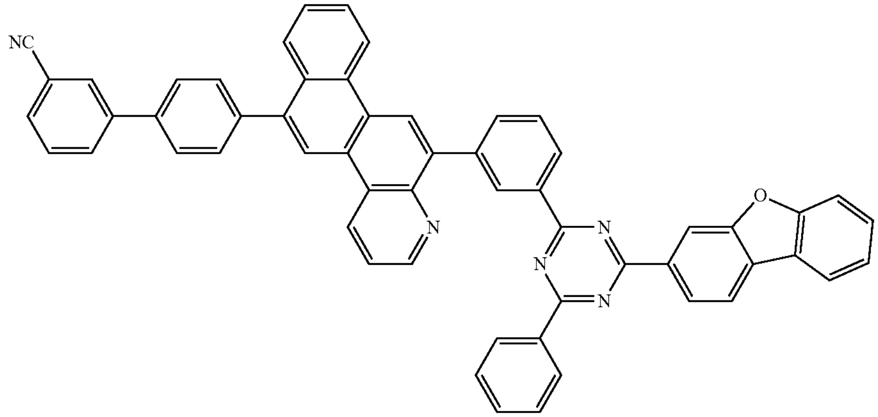
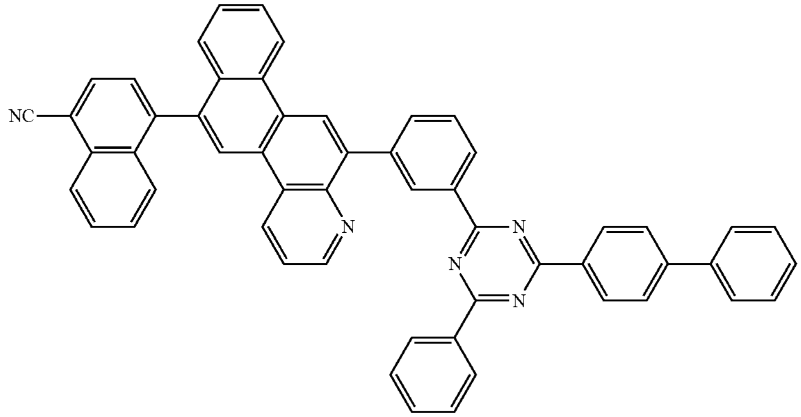
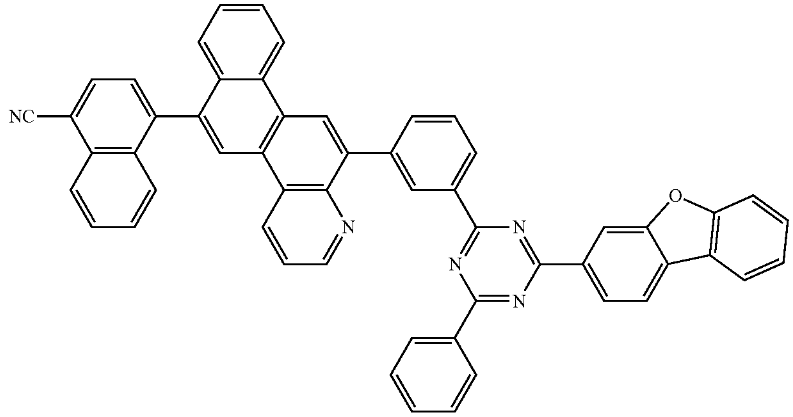

-continued
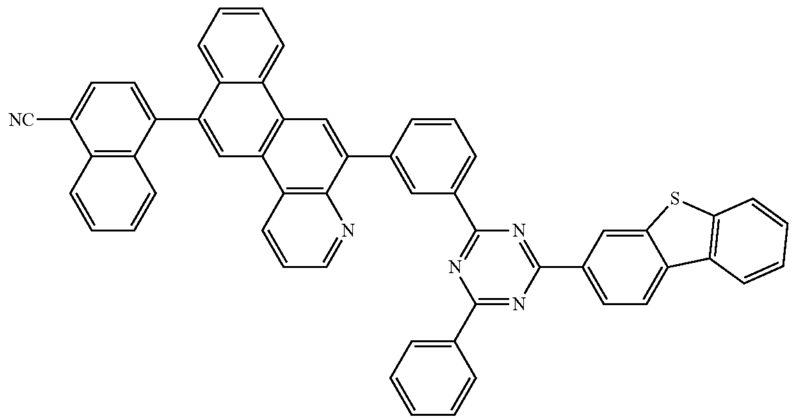
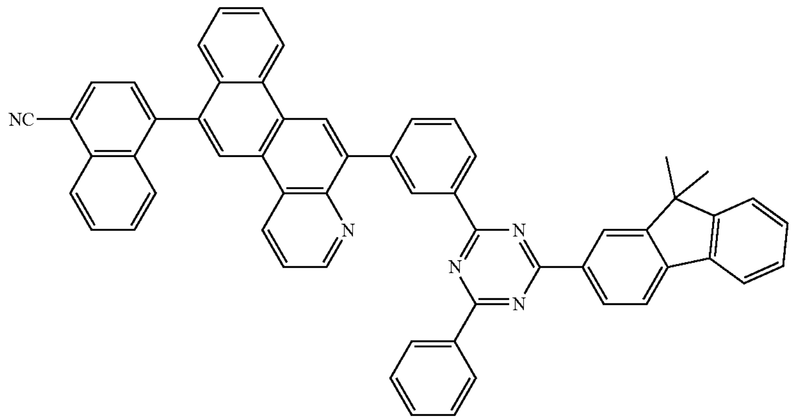
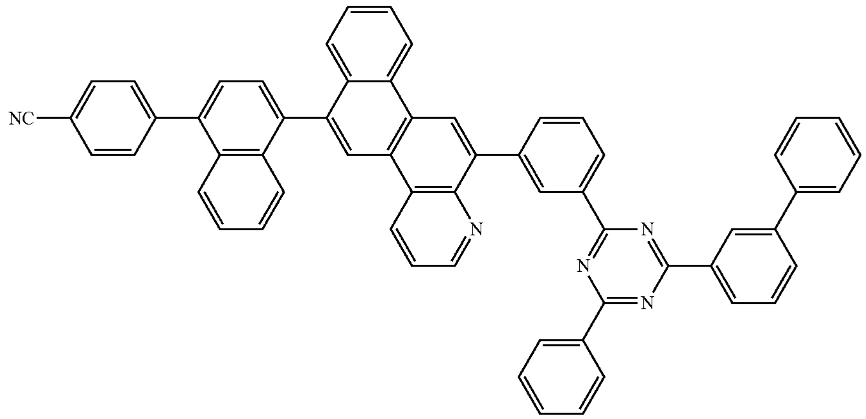
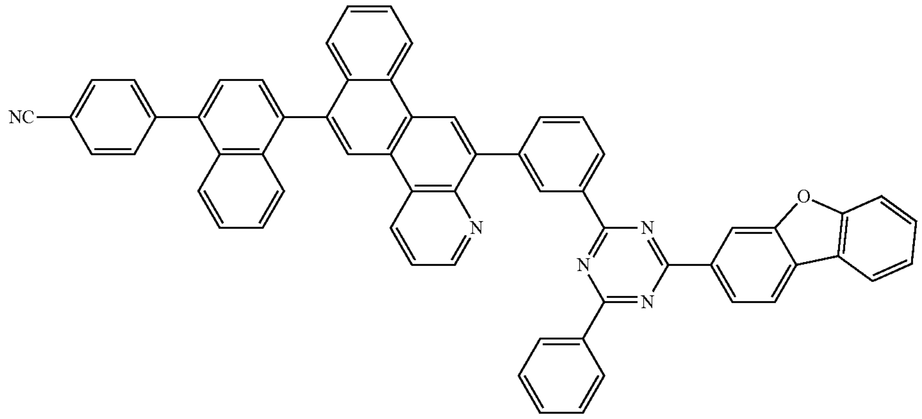

-continued
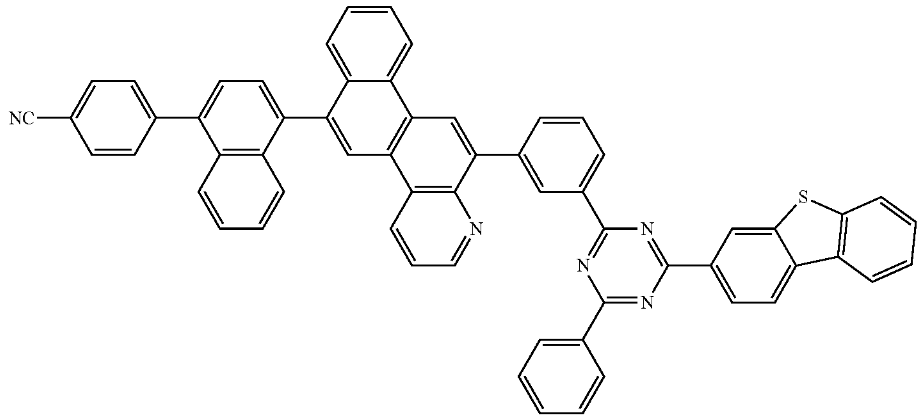
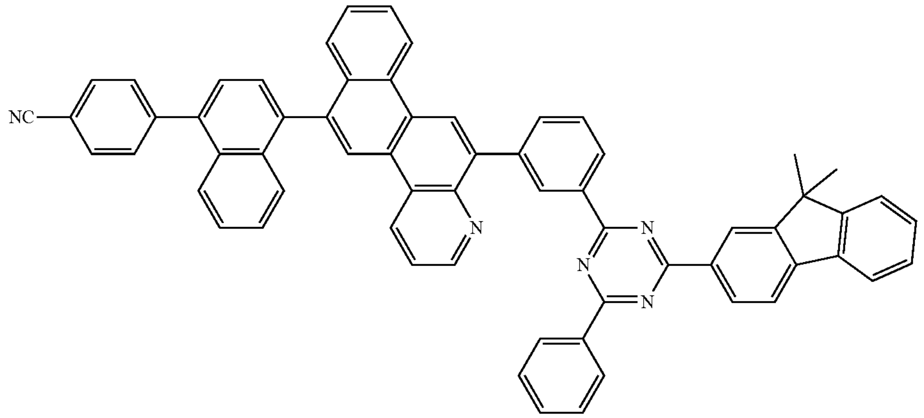
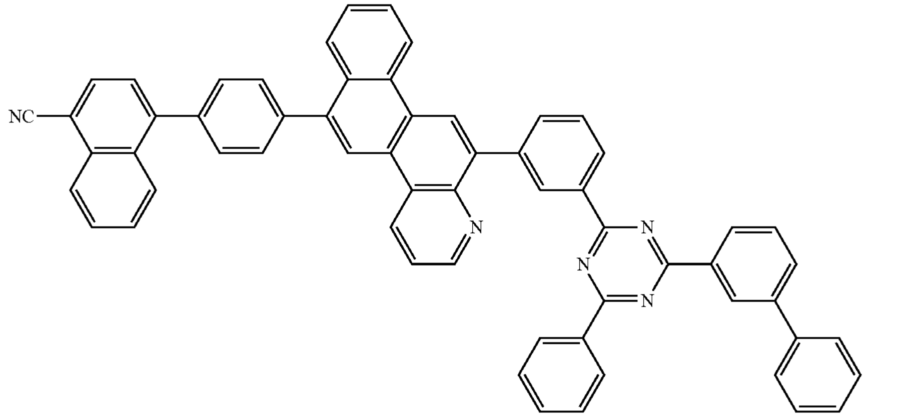
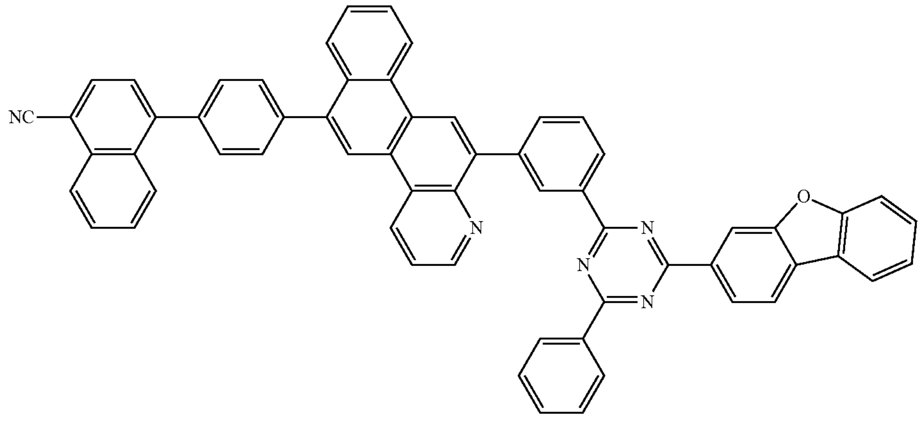

-continued
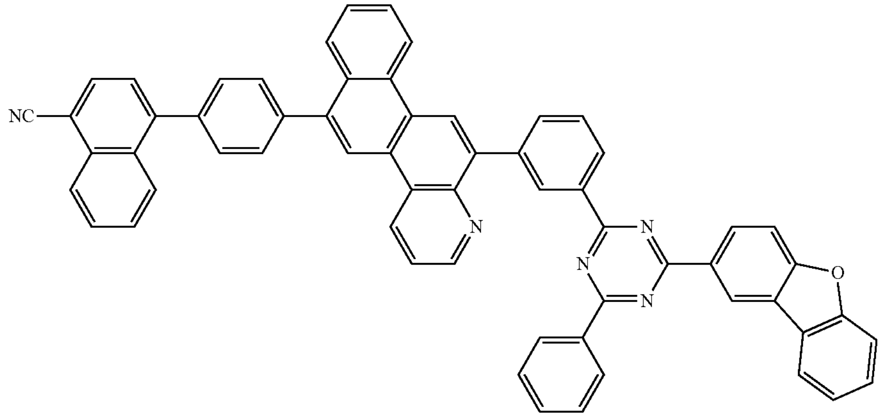
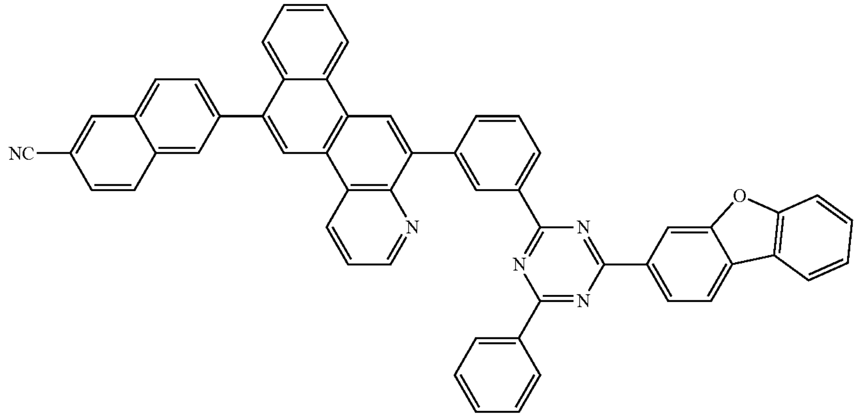
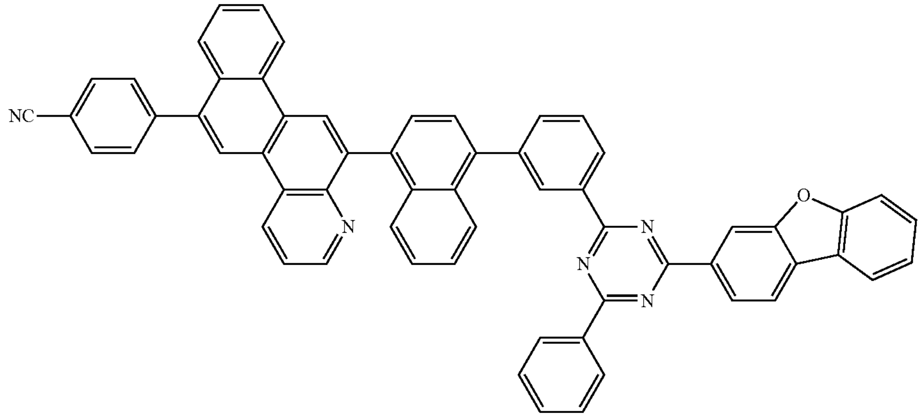
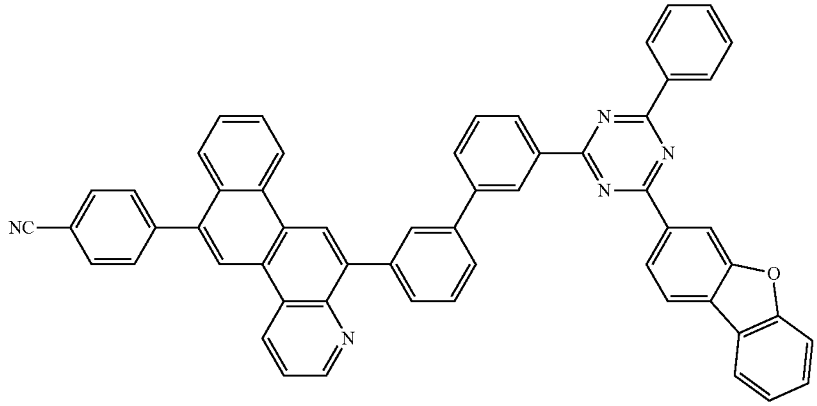

-continued
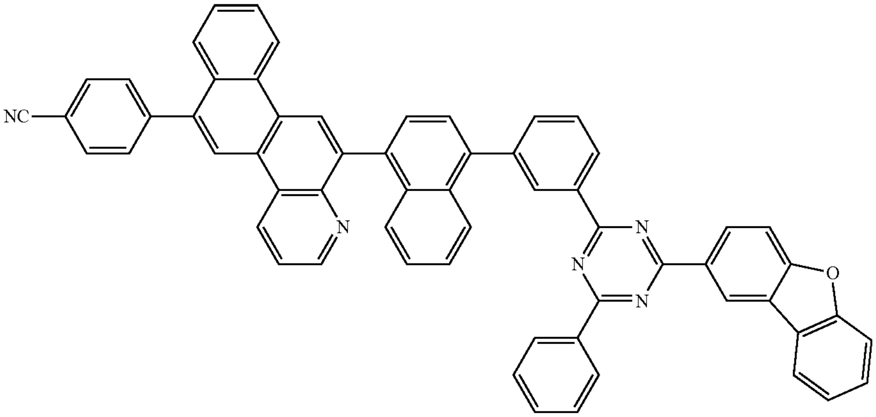
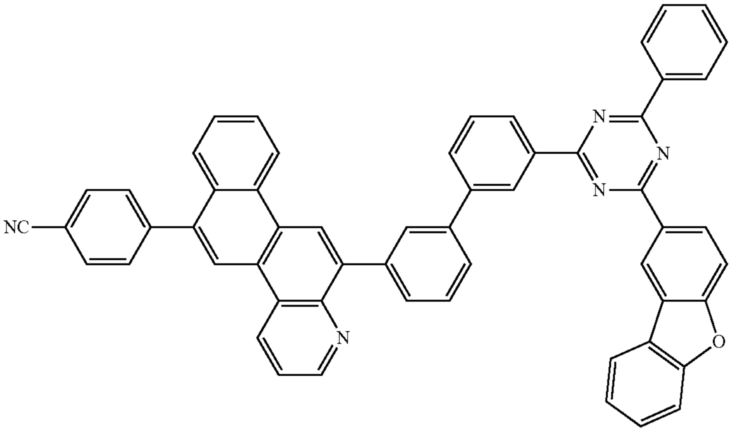
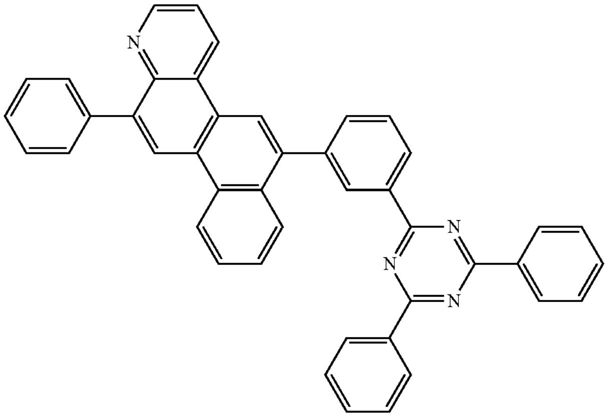
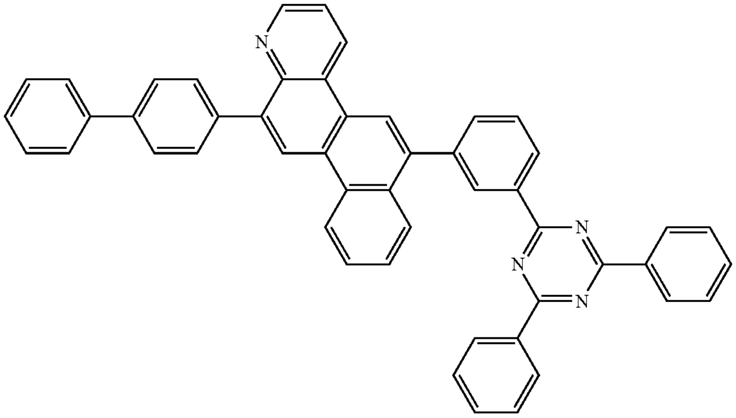

-continued
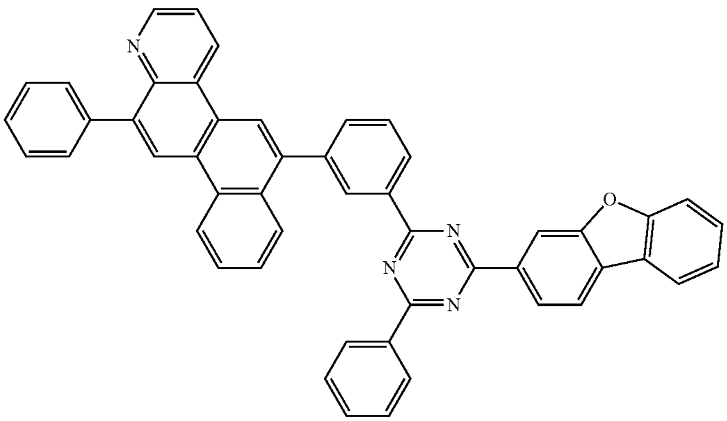
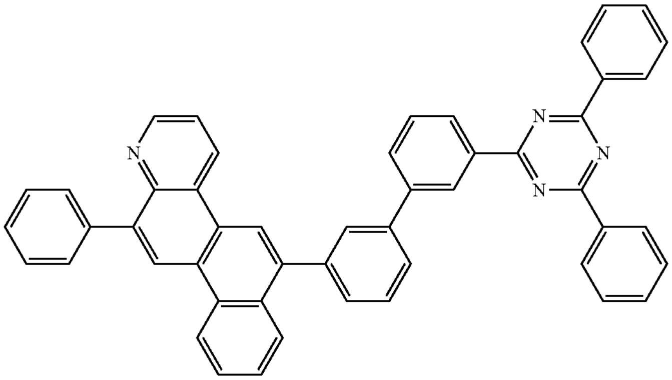
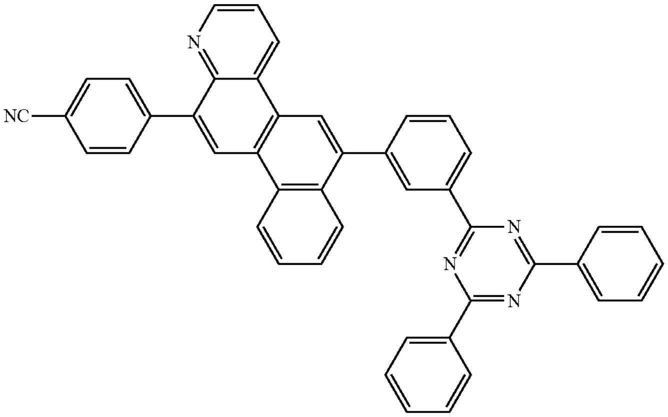
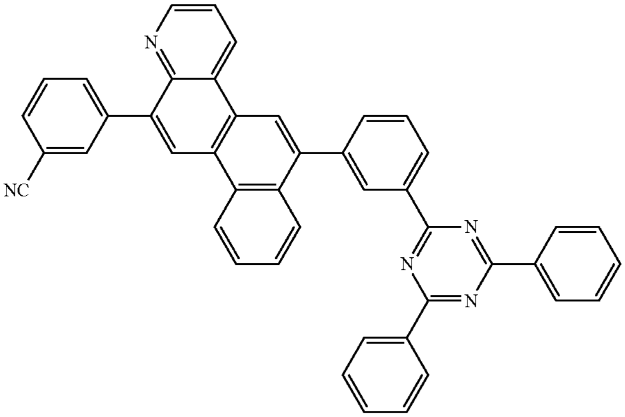

-continued
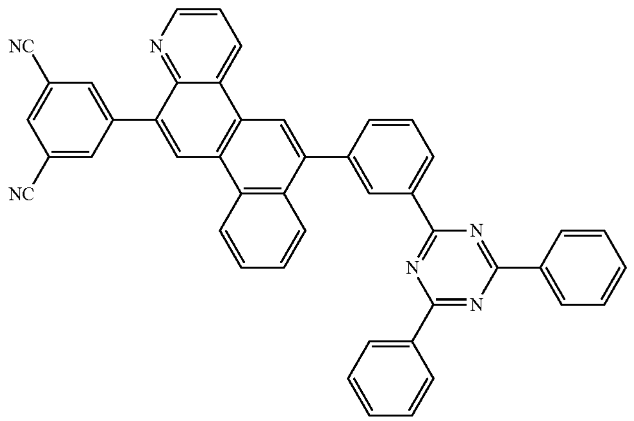
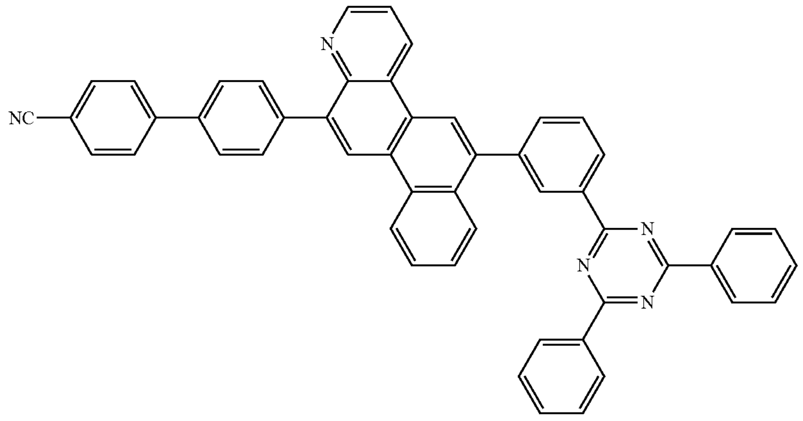
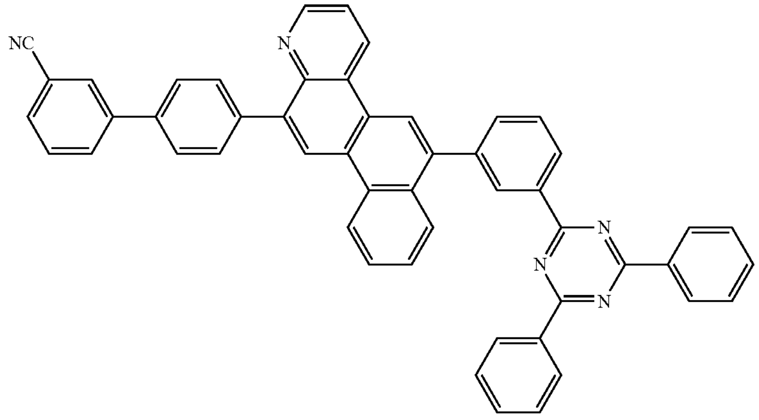
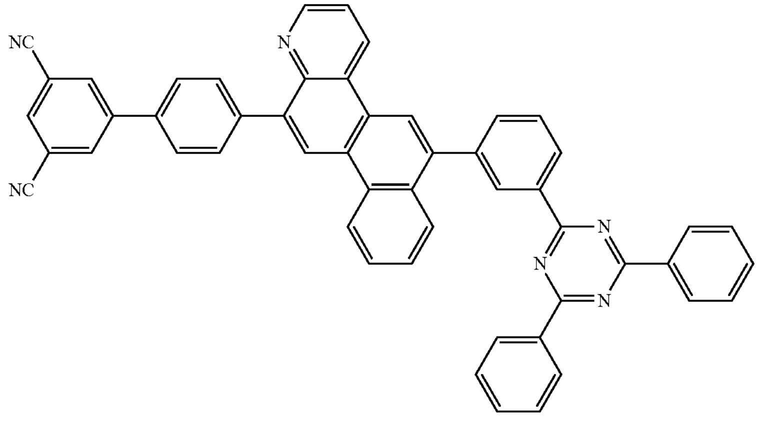

-continued
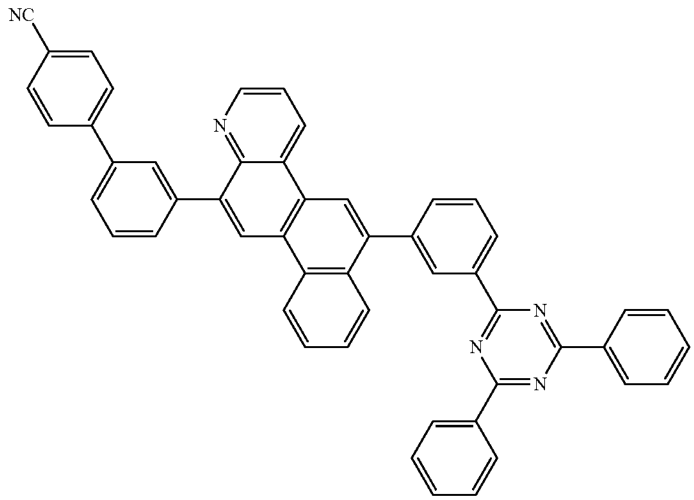
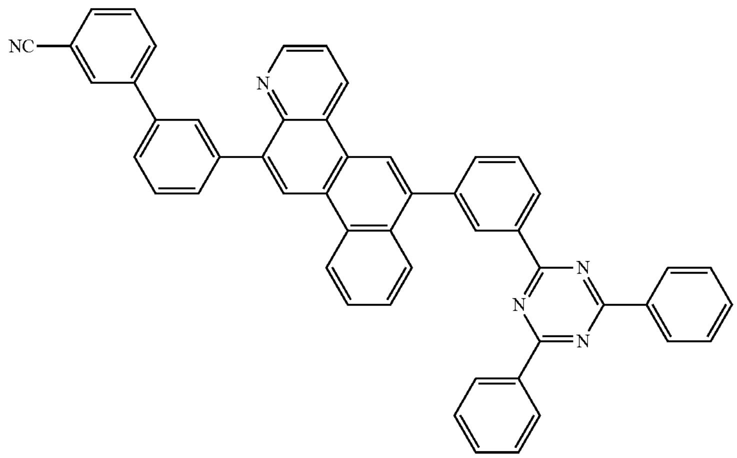
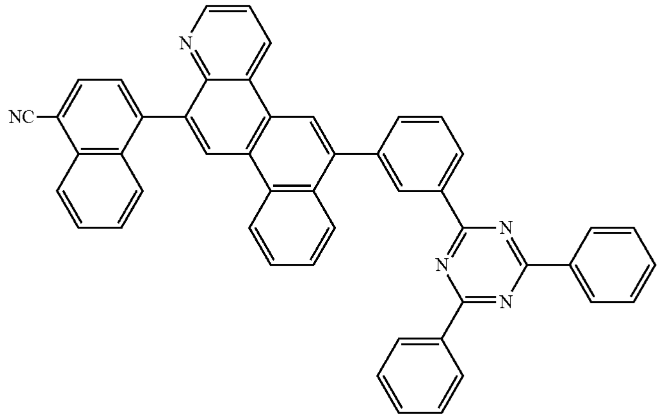

-continued
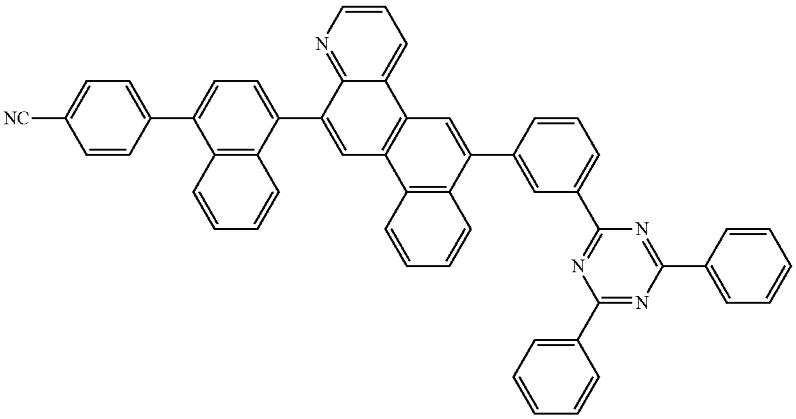
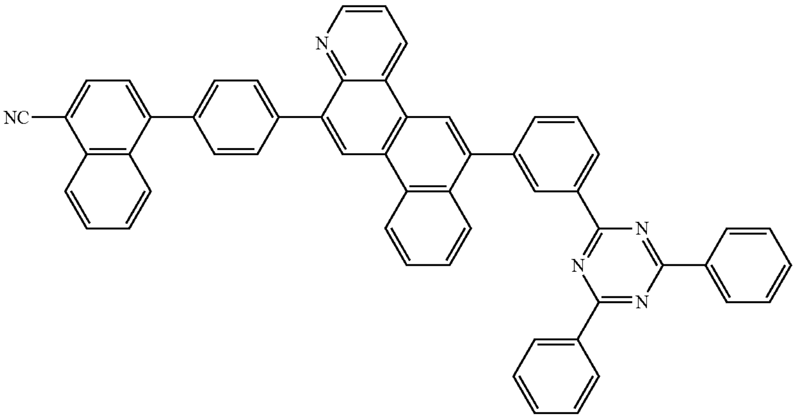
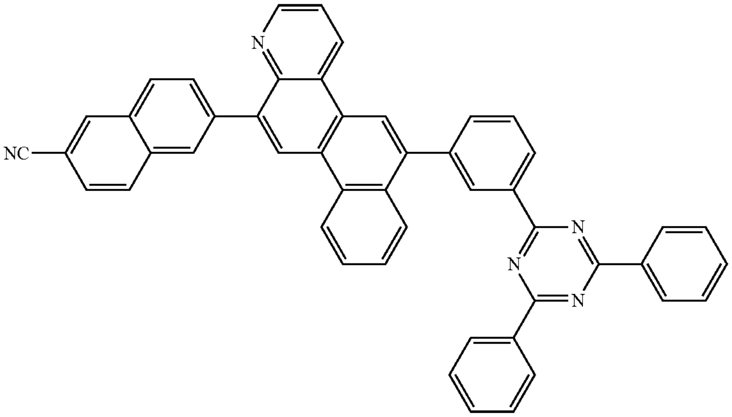
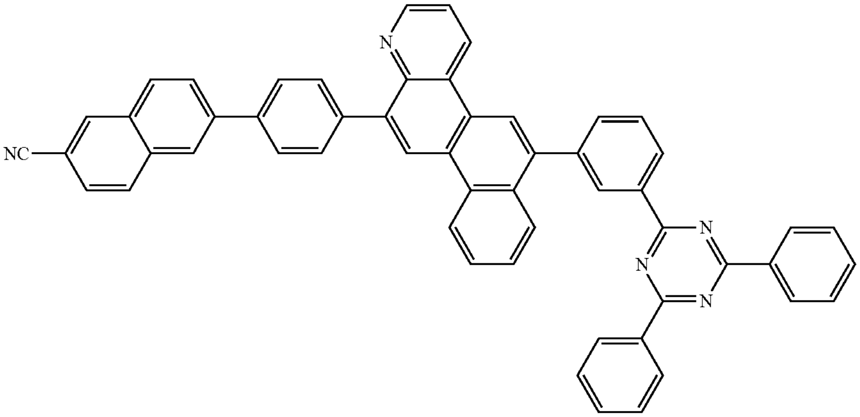

-continued
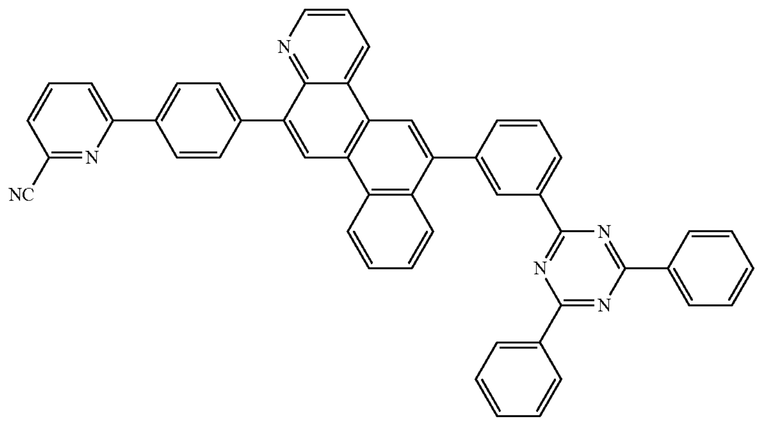
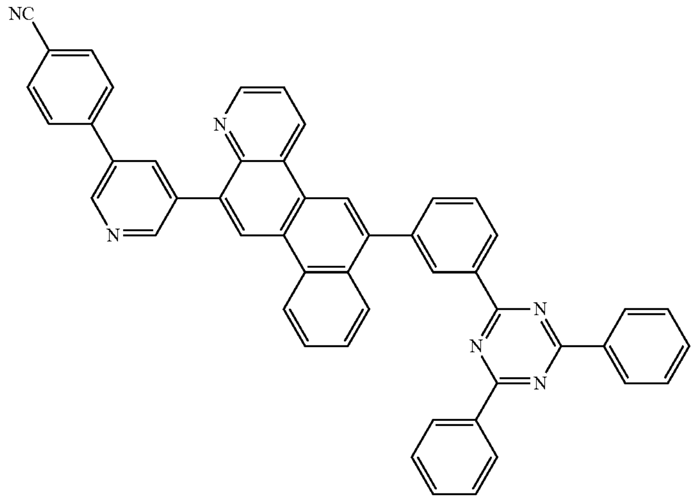
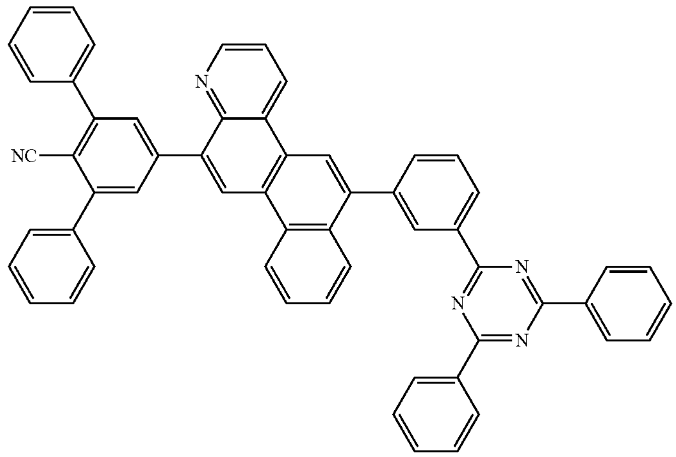

-continued
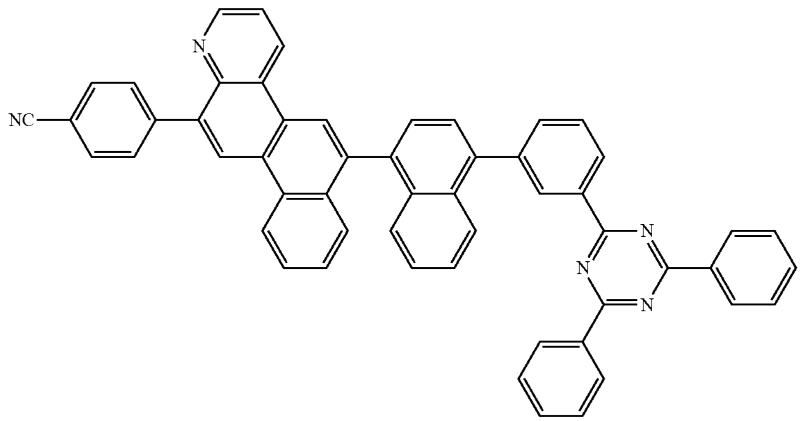
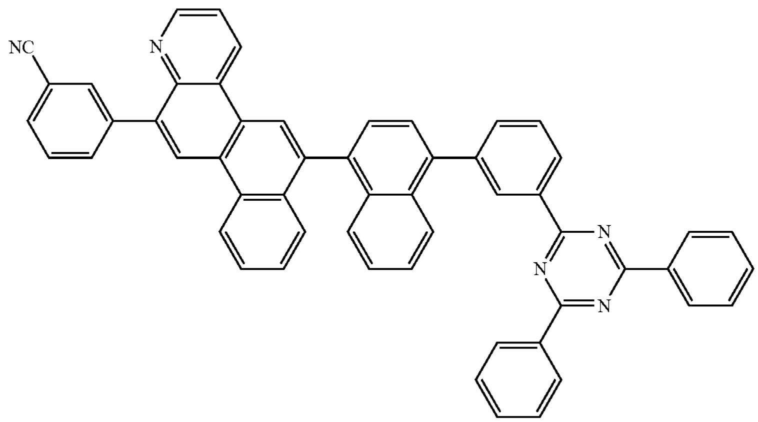
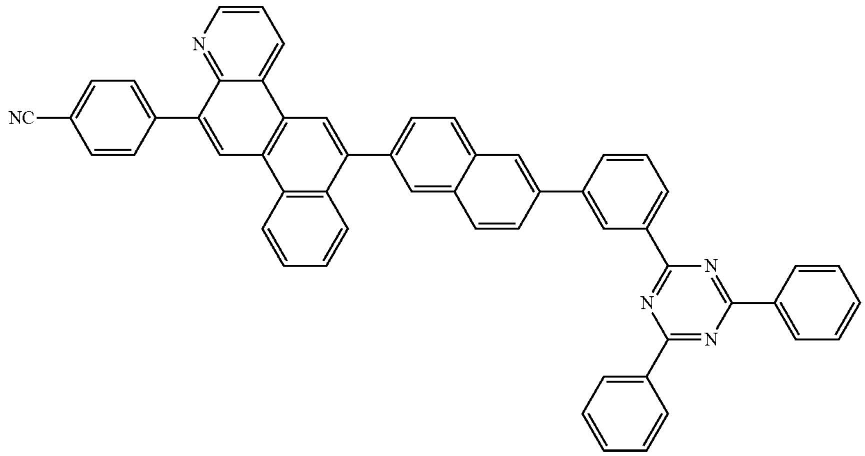

-continued
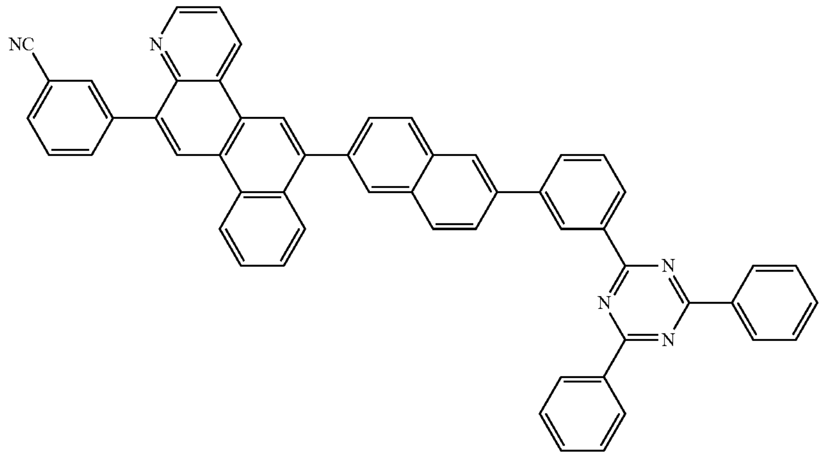
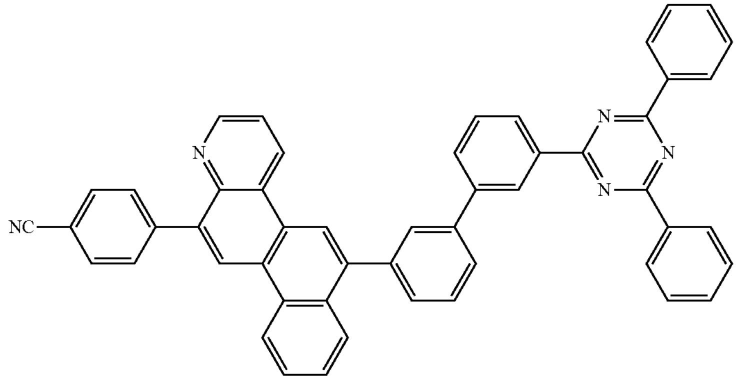
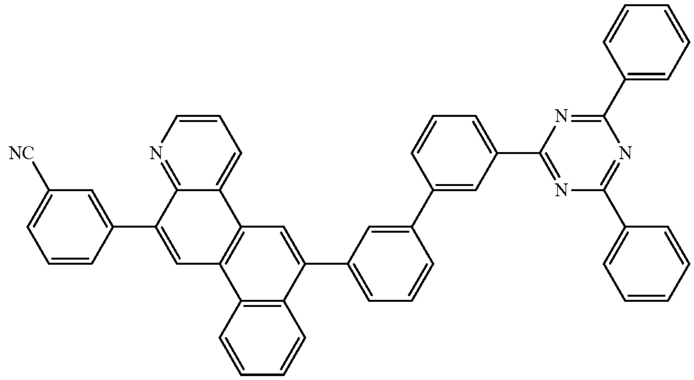
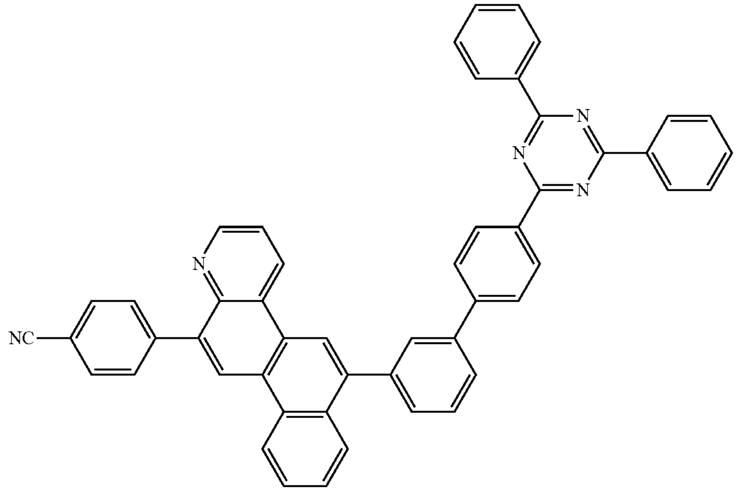

-continued
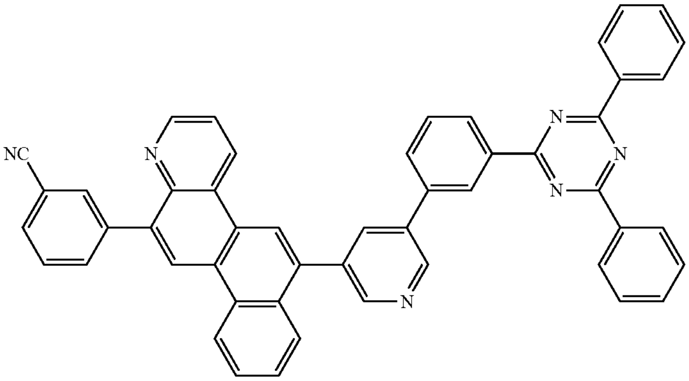
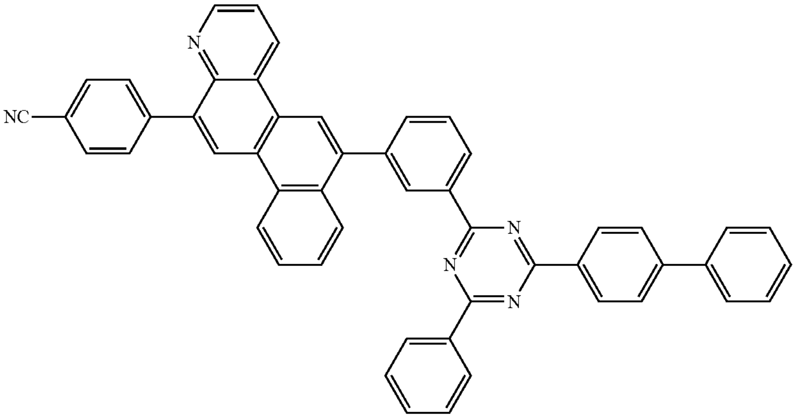
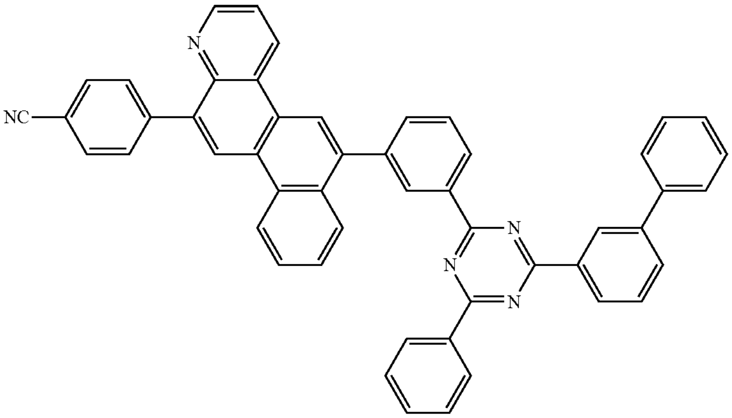
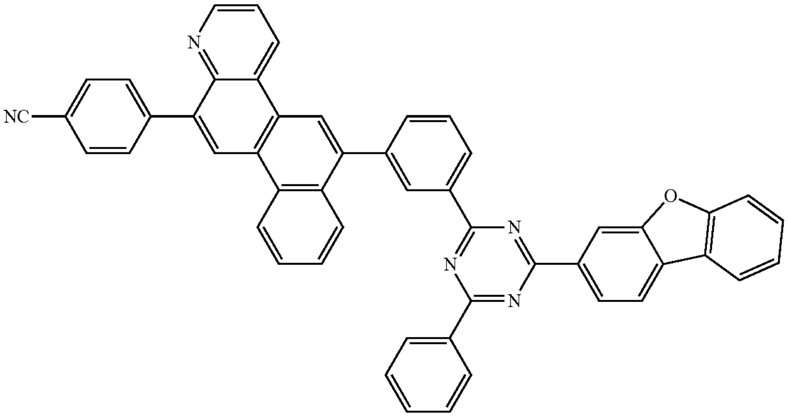

-continued
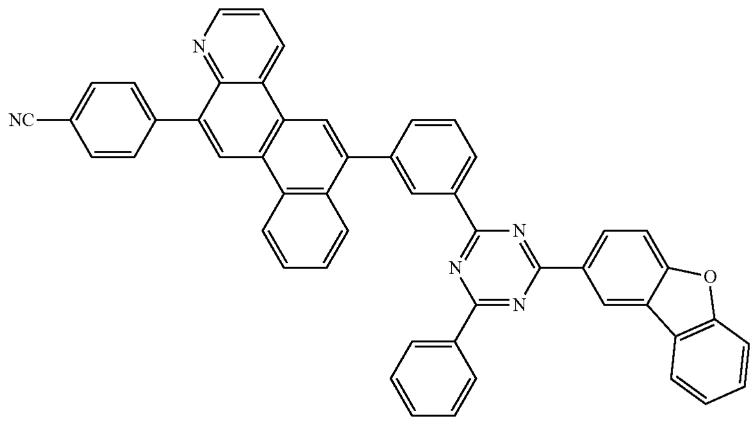
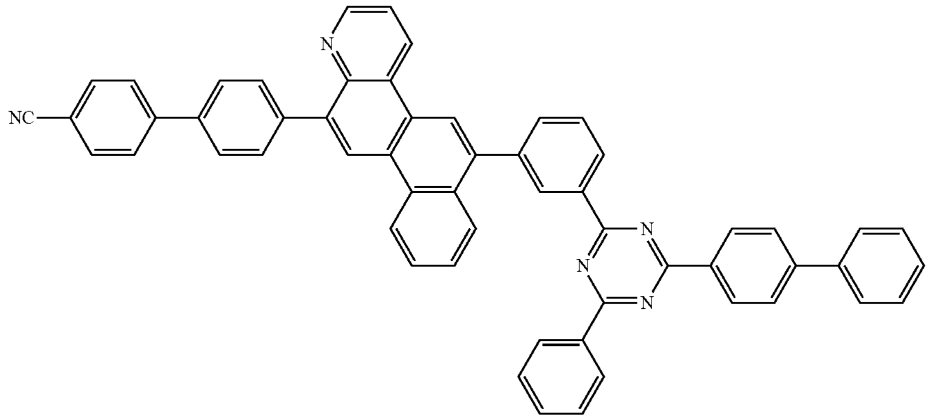
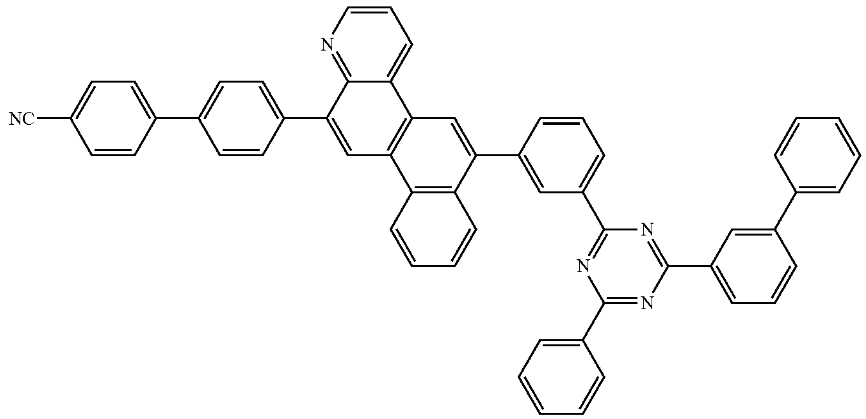
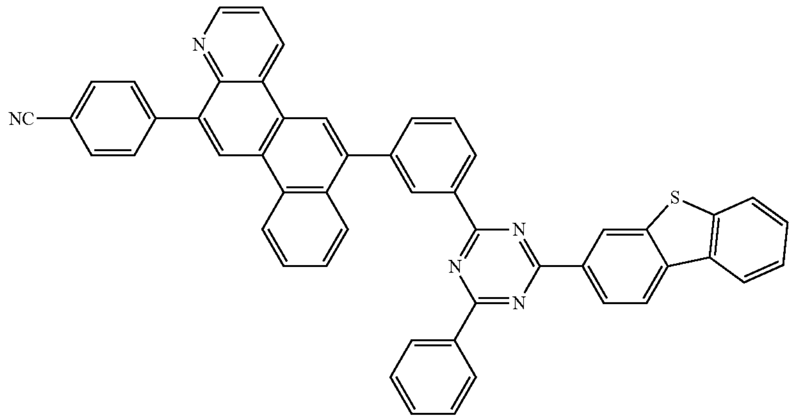

-continued
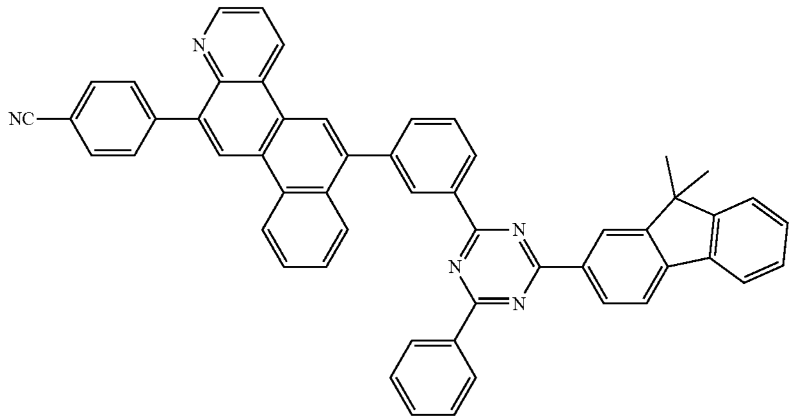
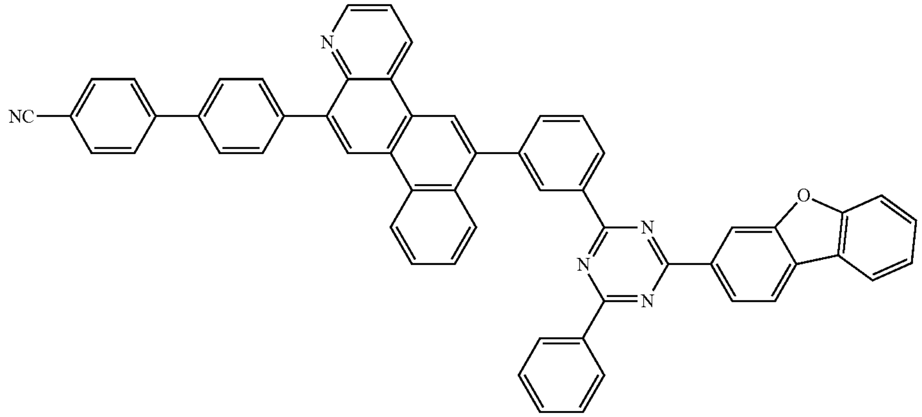
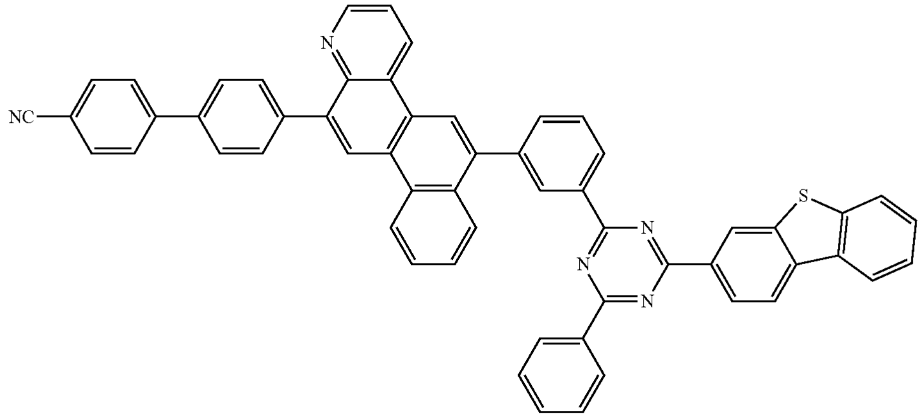
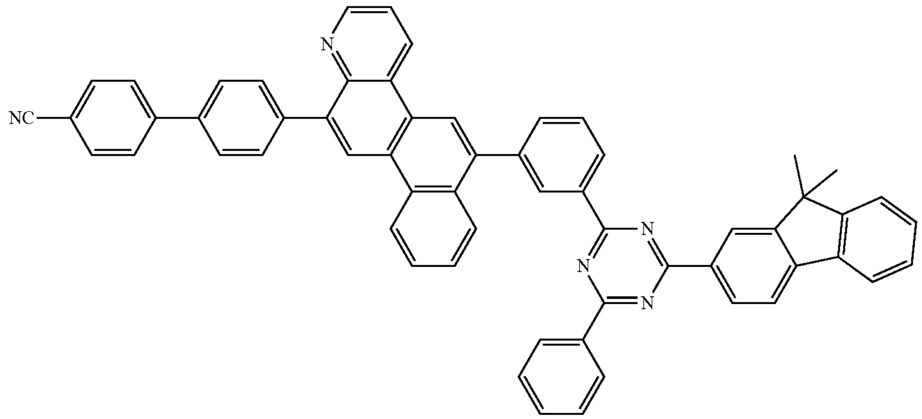

-continued
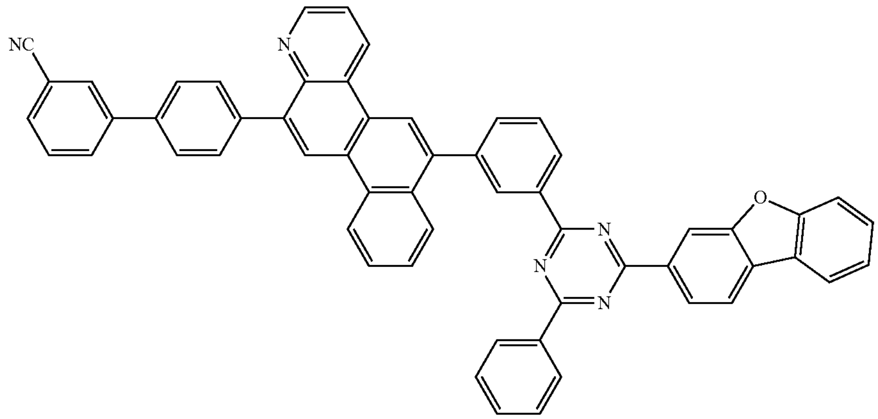
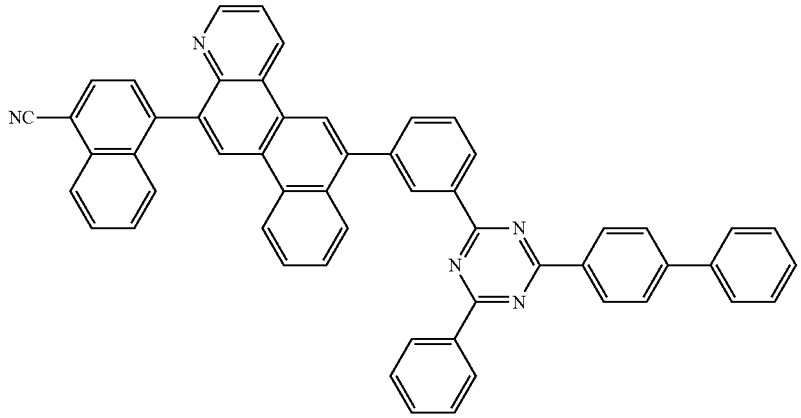
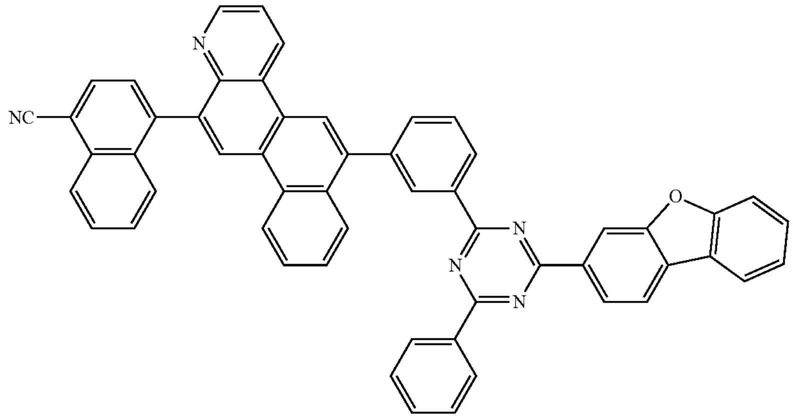
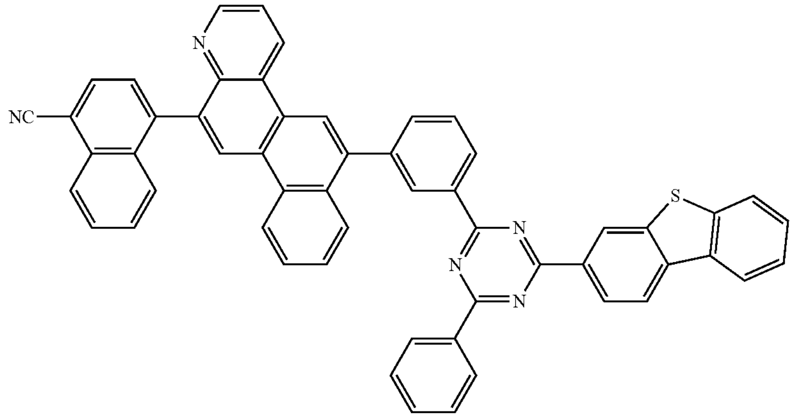

-continued
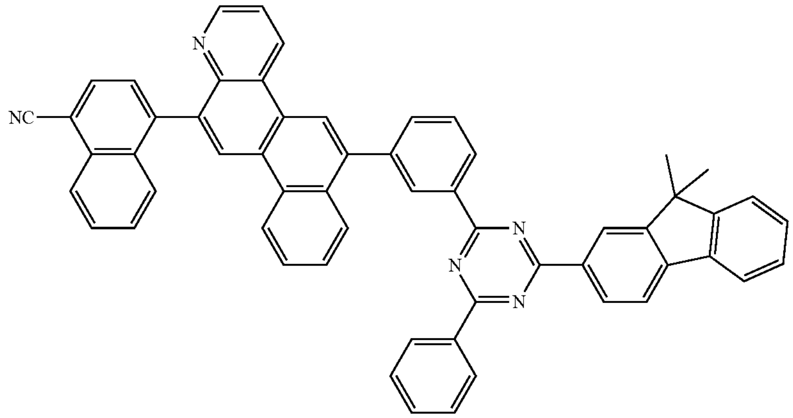
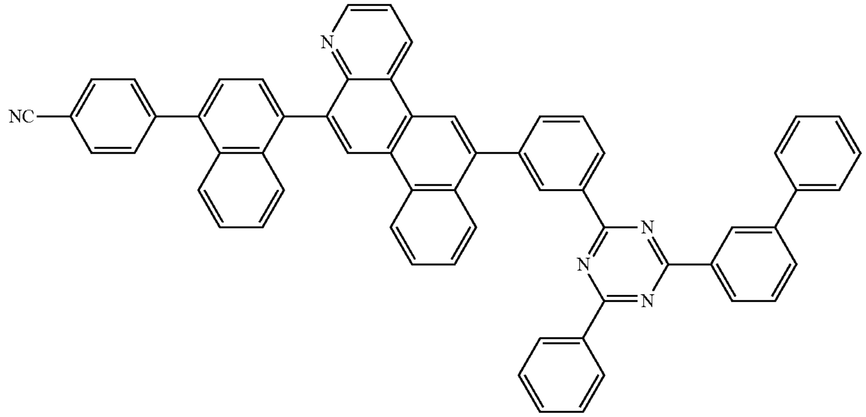
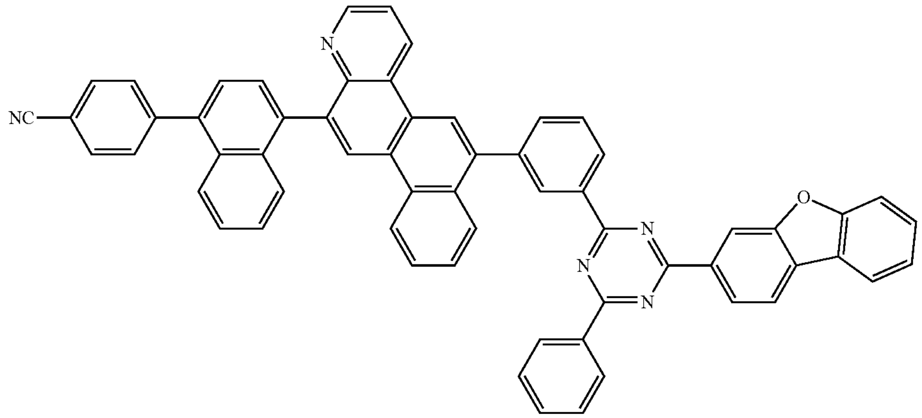
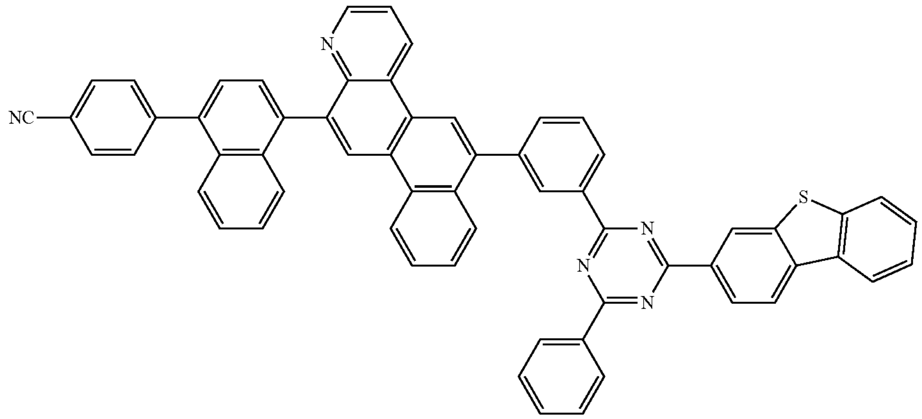

-continued
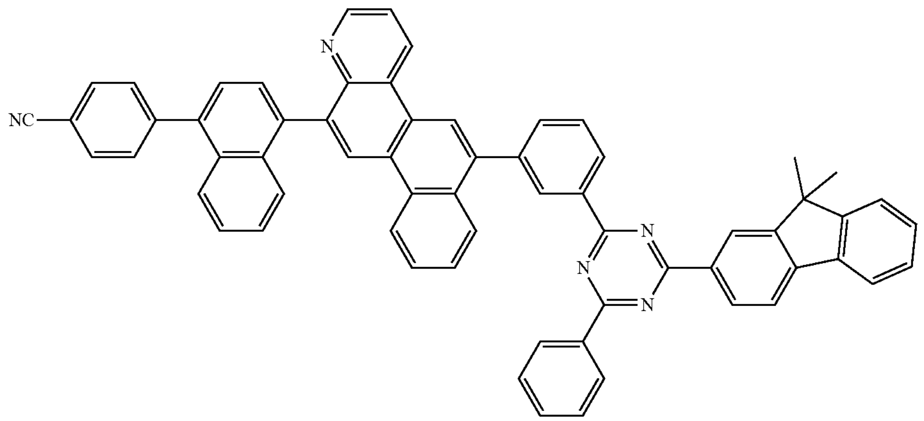
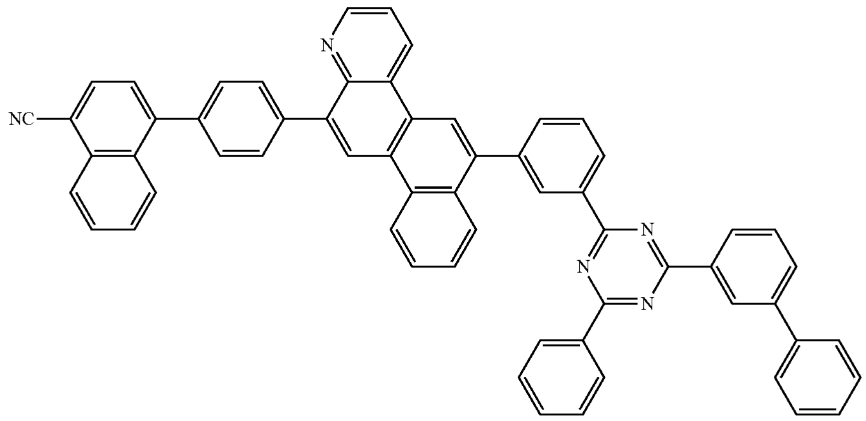
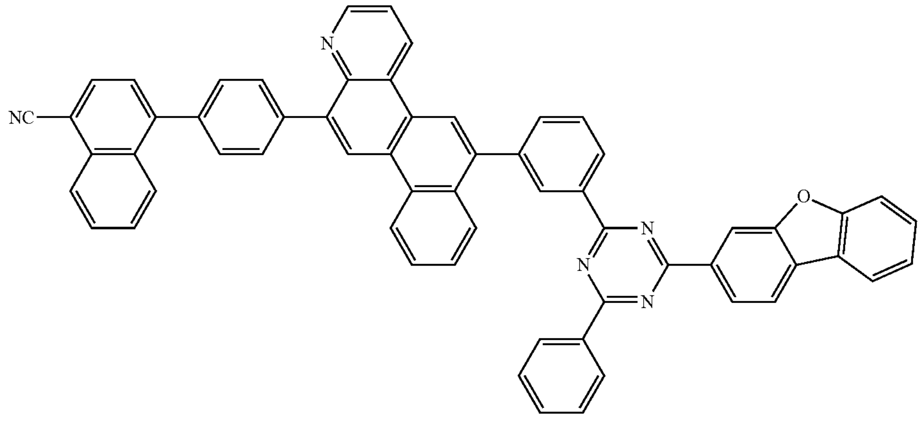
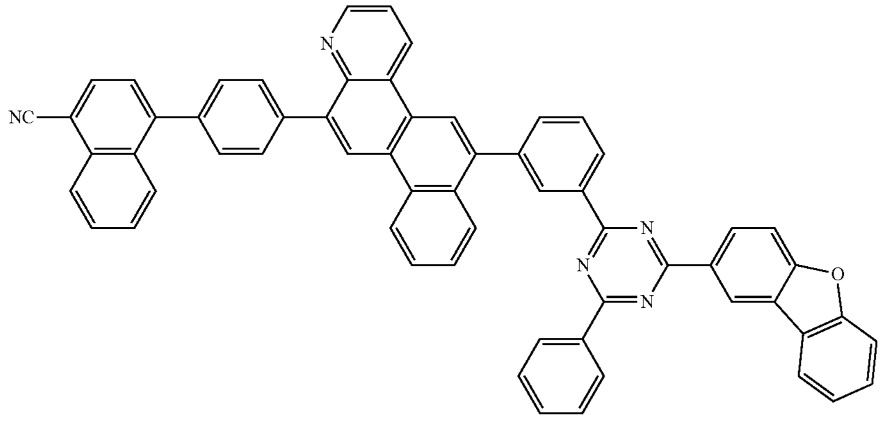

-continued
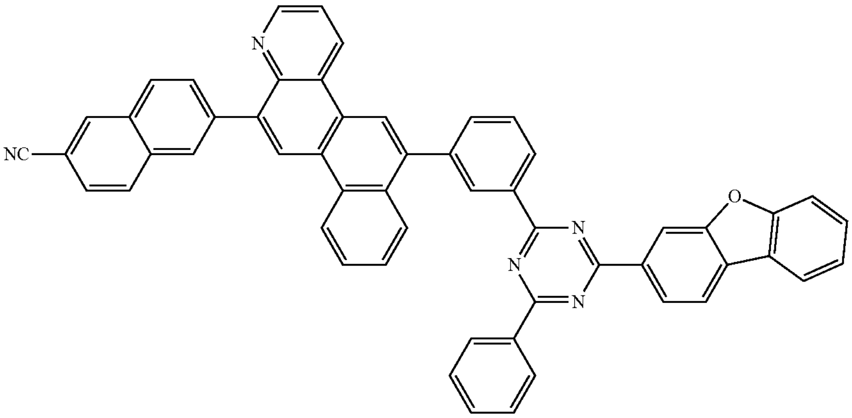
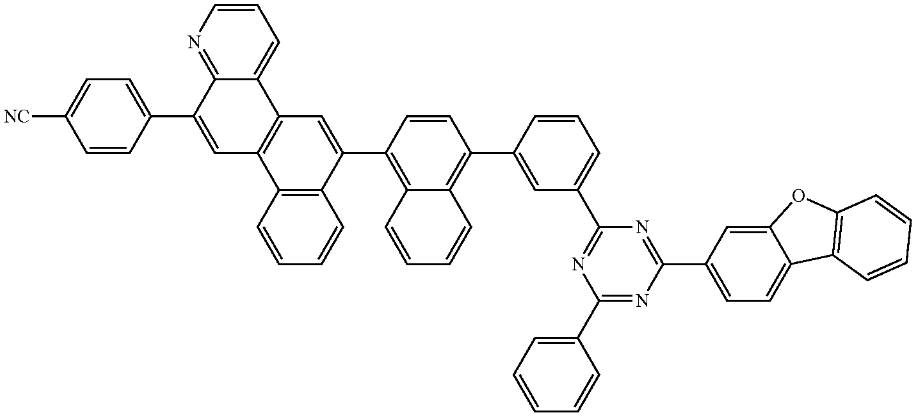
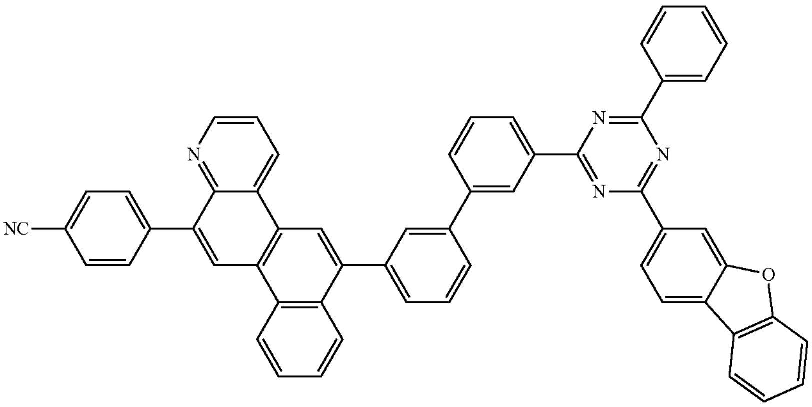
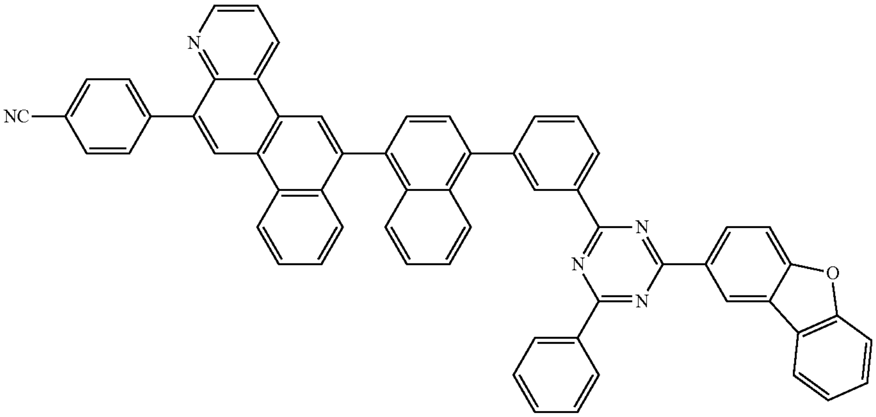

-continued
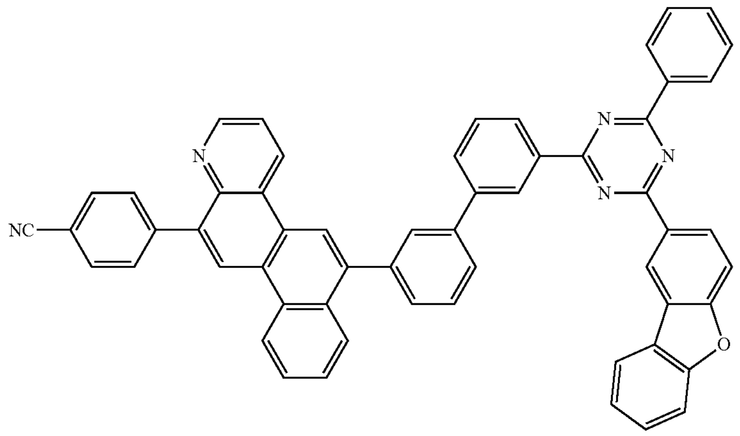
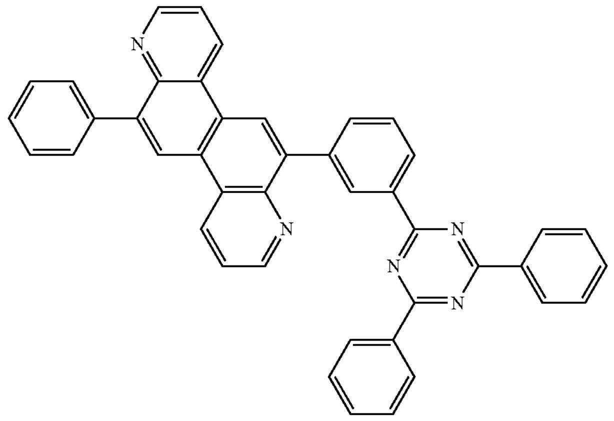
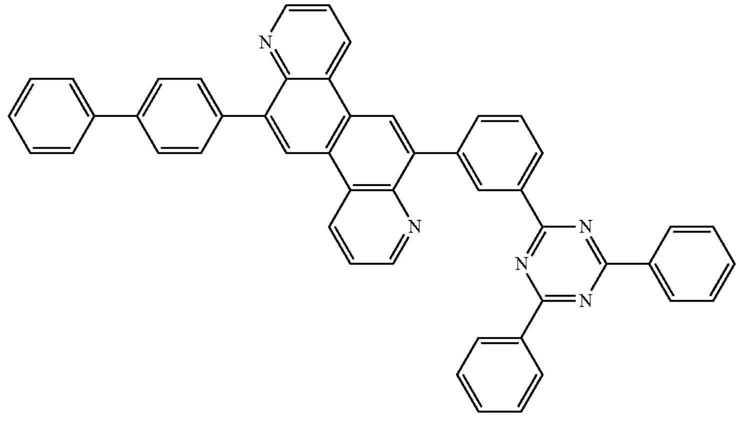
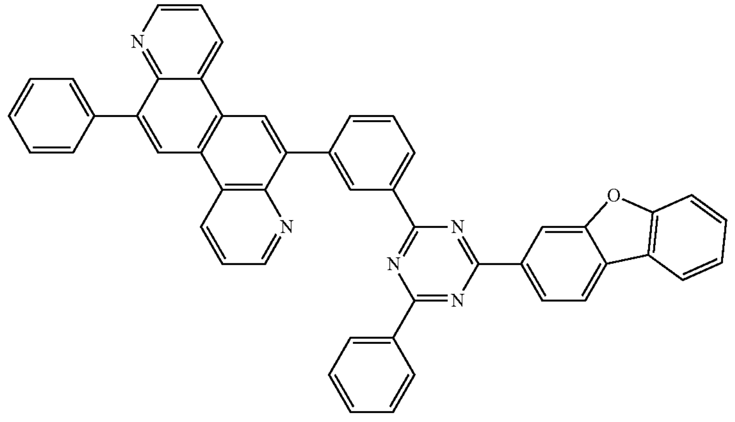

-continued
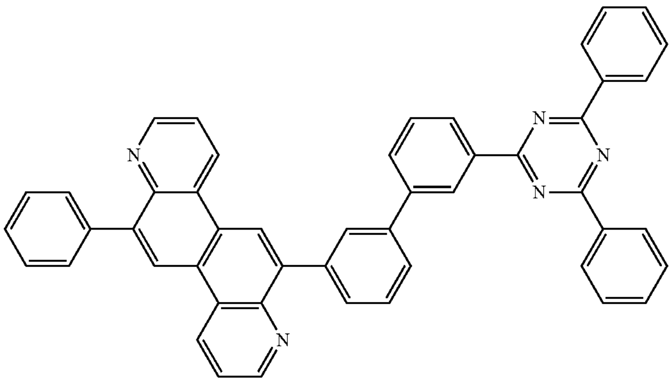
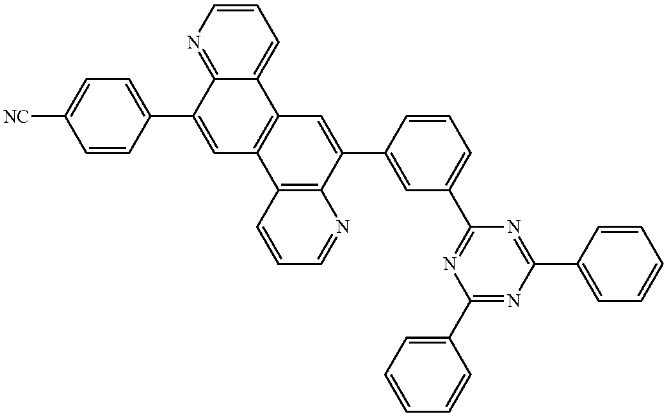
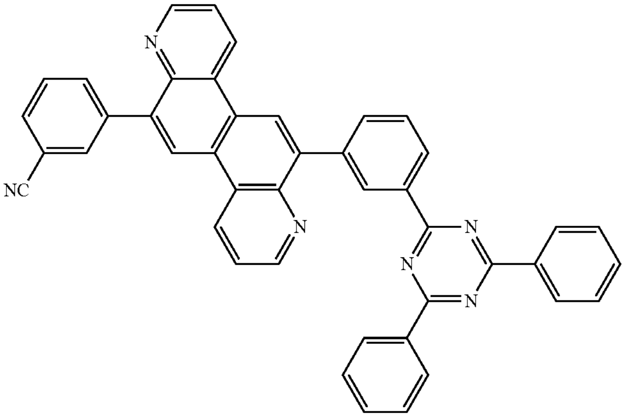
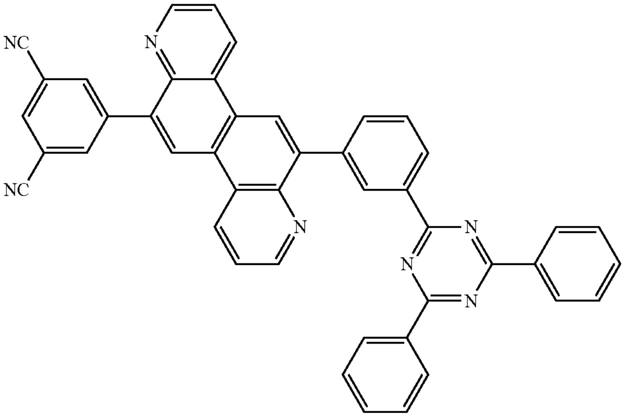

-continued
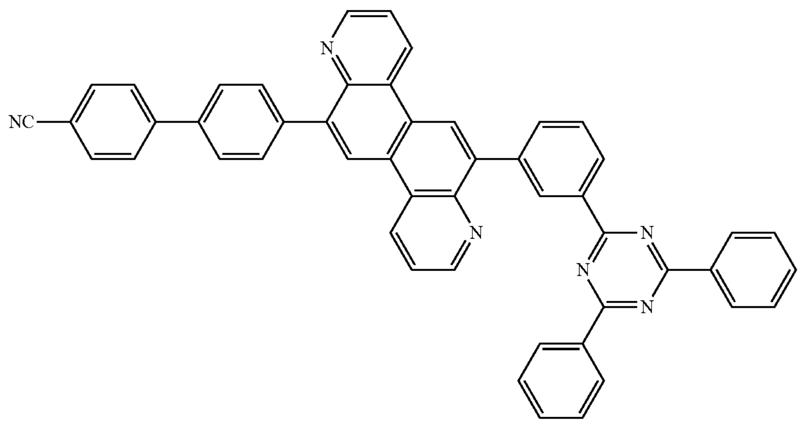
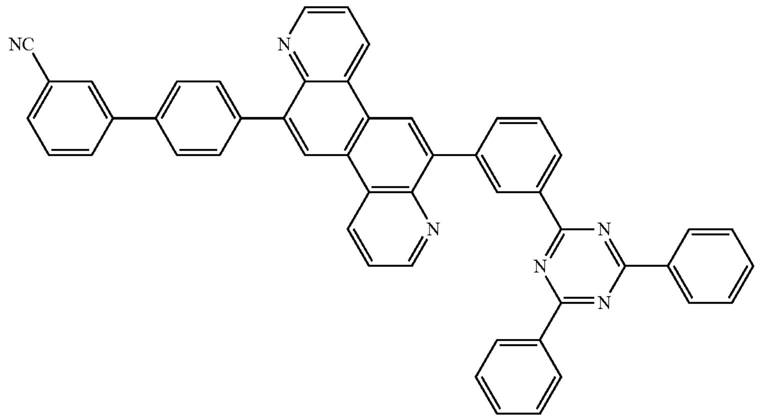
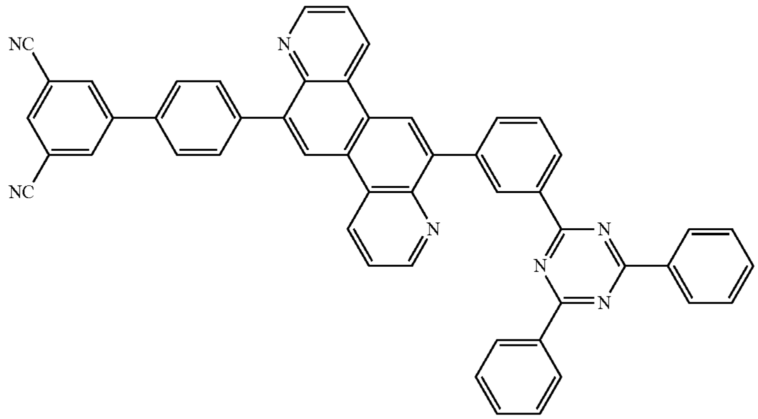

-continued
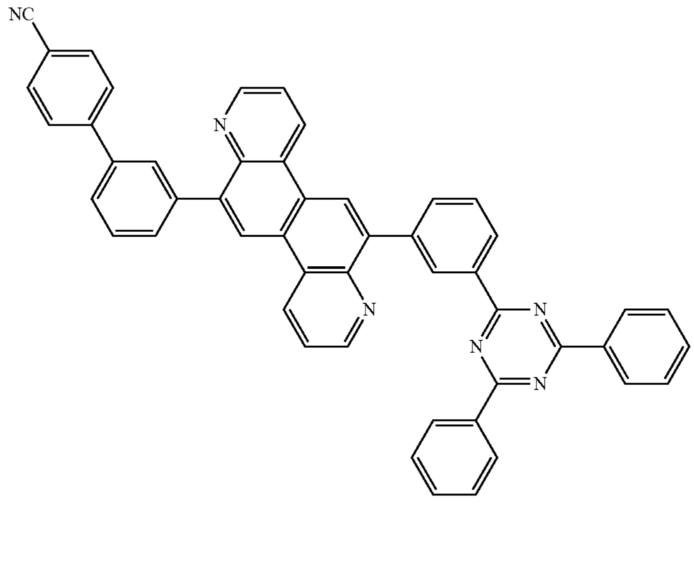
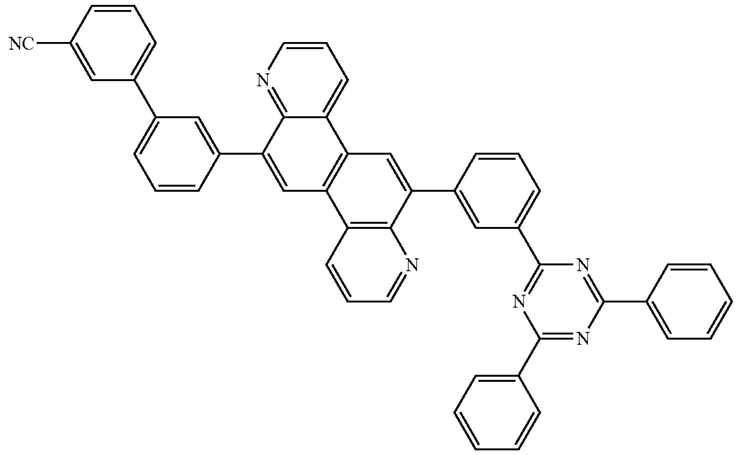
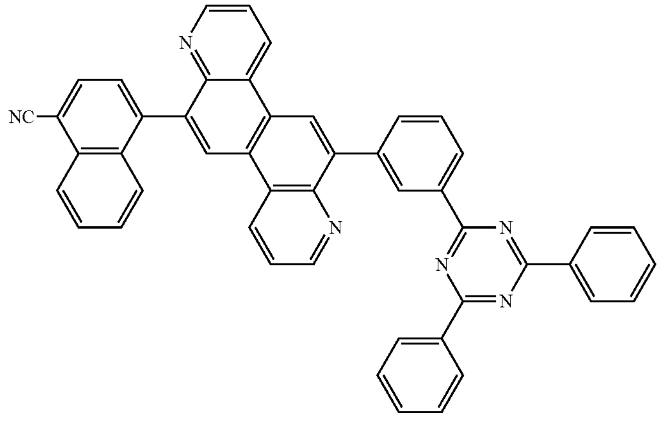

-continued
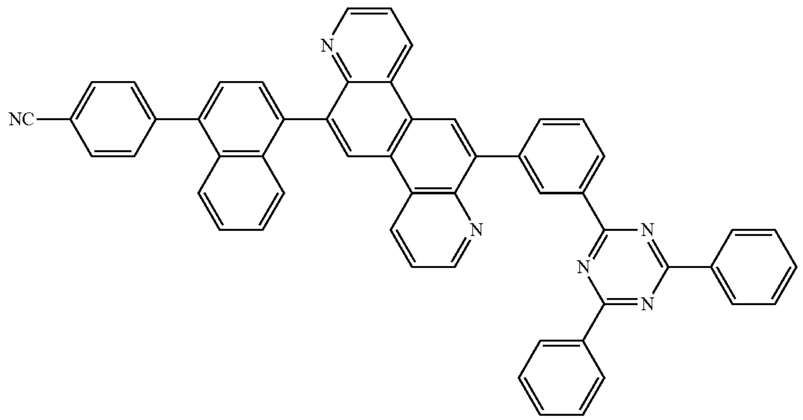
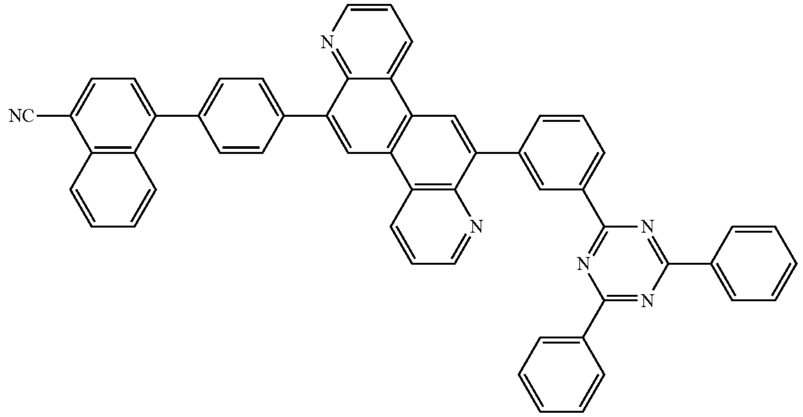
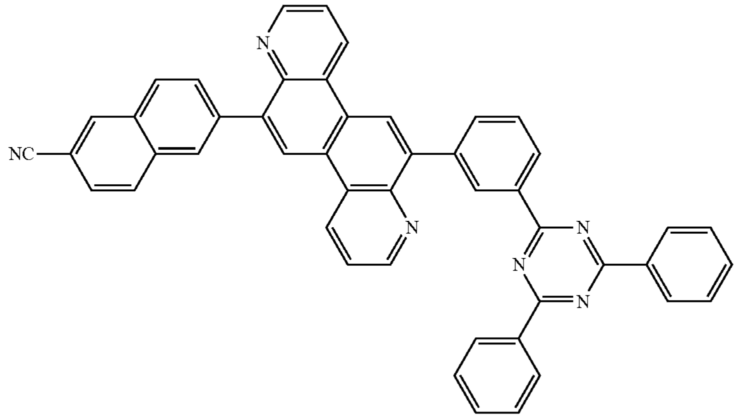
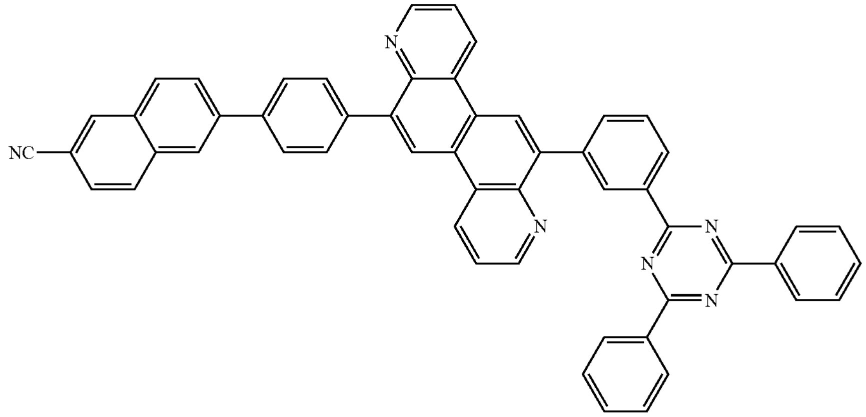

-continued
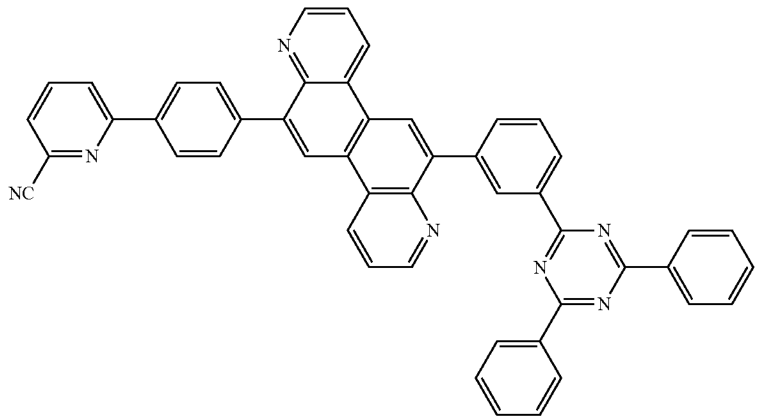
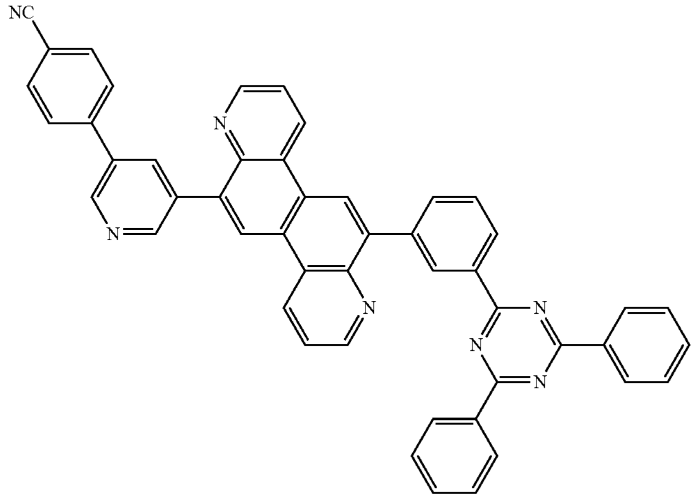
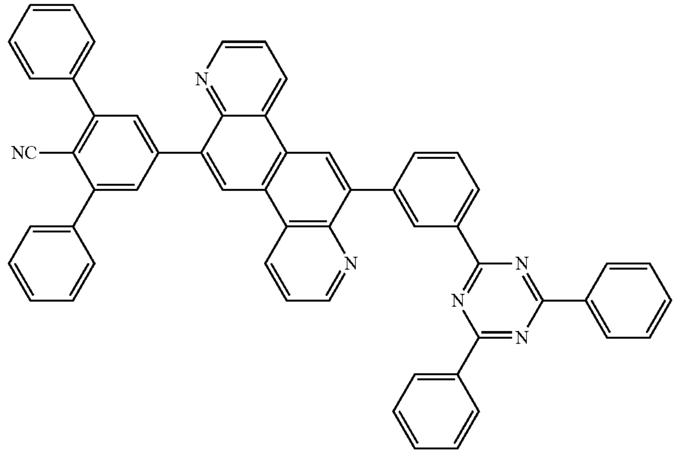

-continued
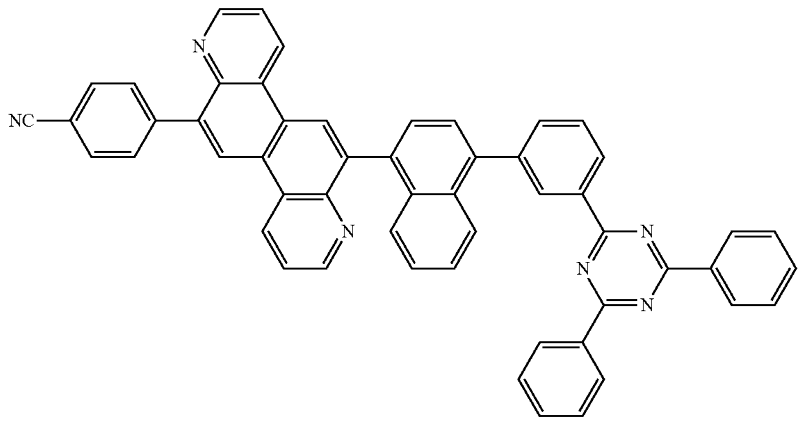
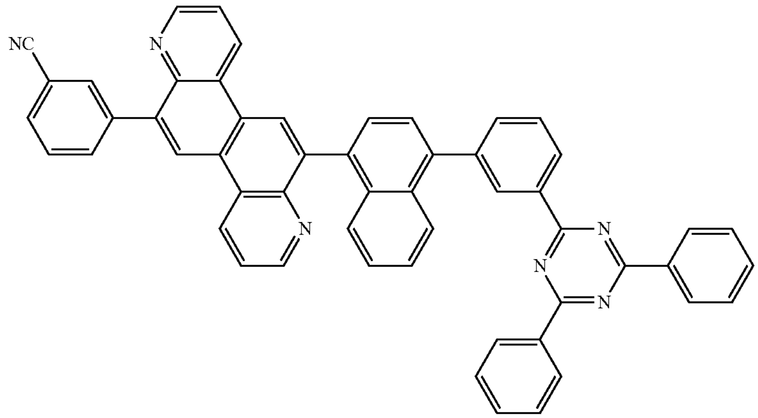
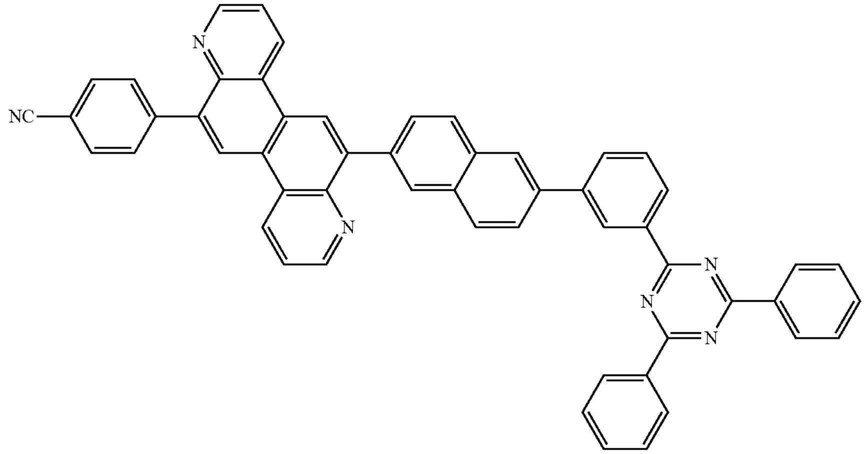

-continued
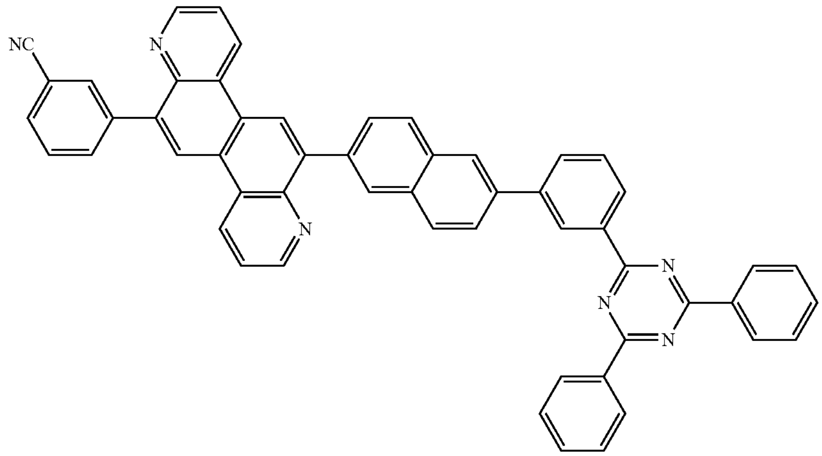
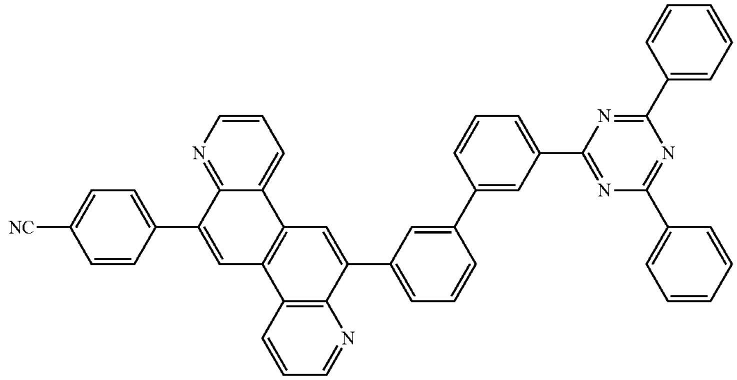
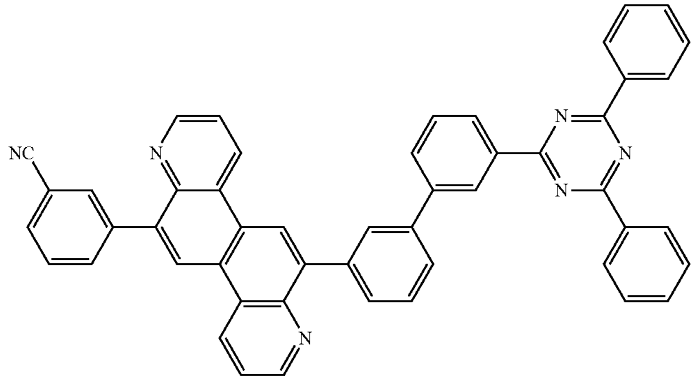
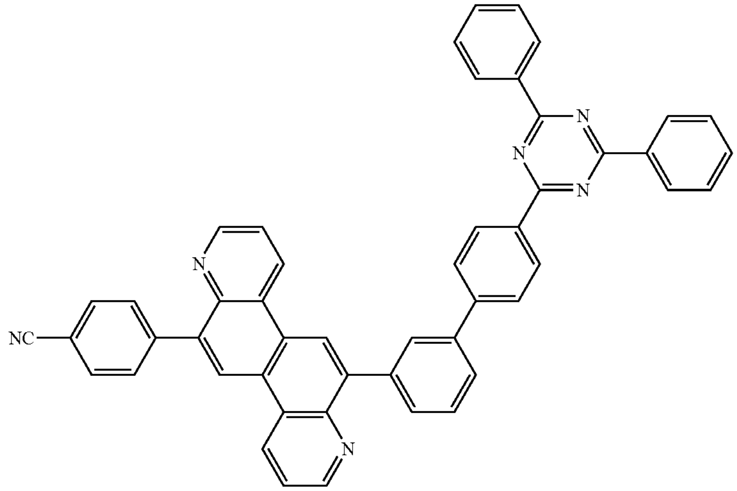

-continued
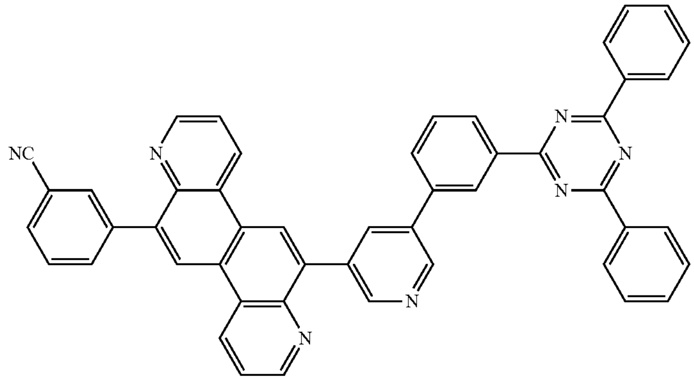
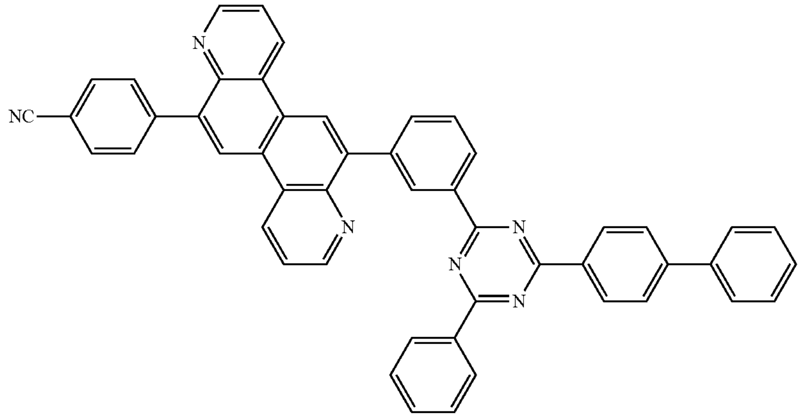
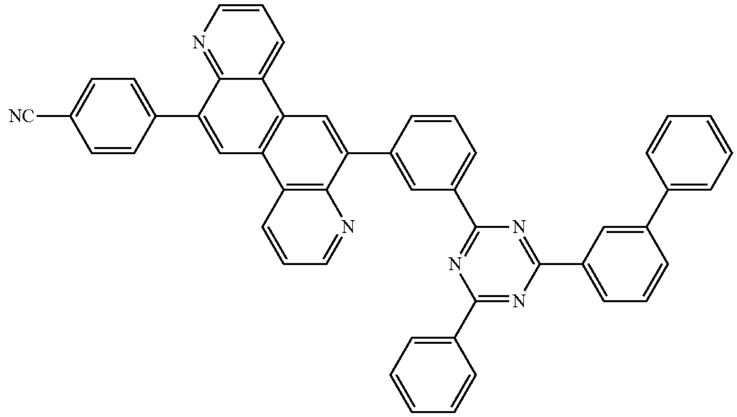
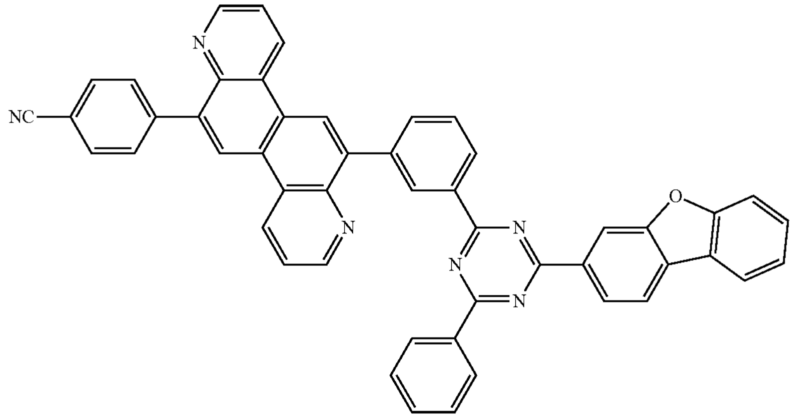

-continued
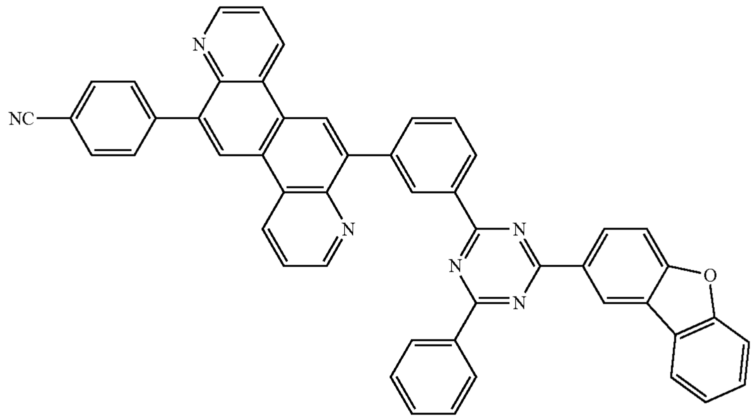
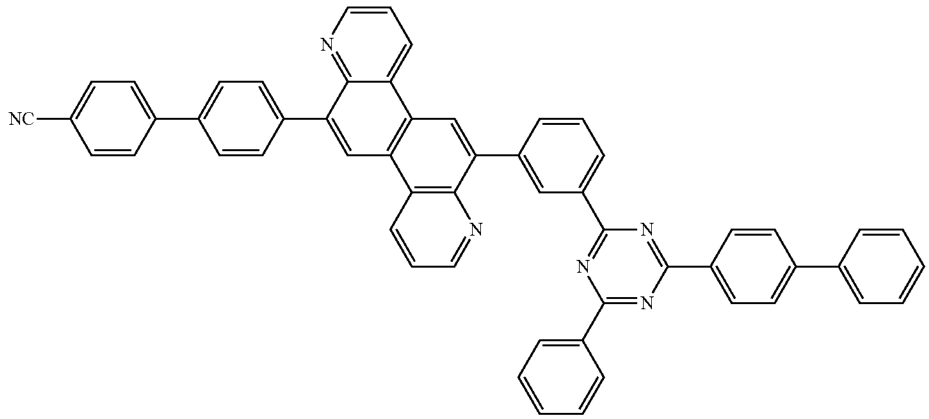
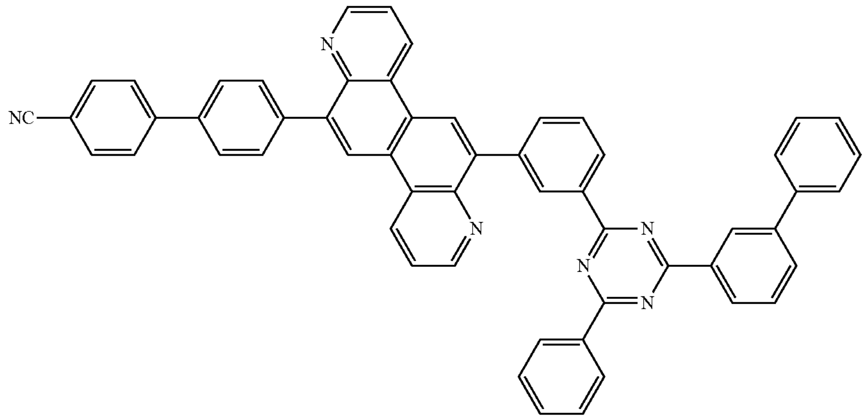
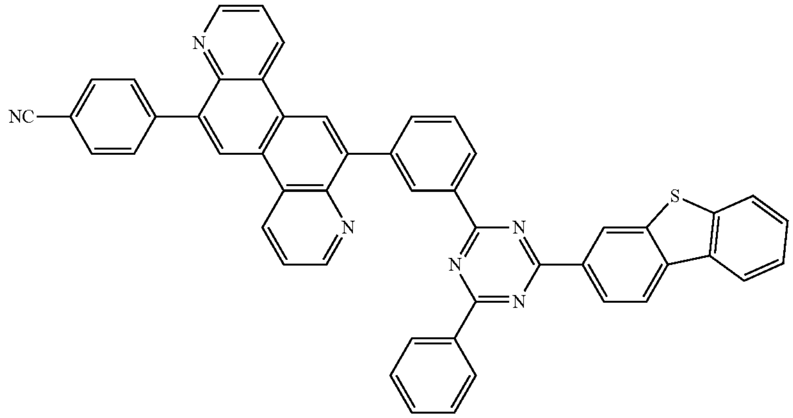

-continued
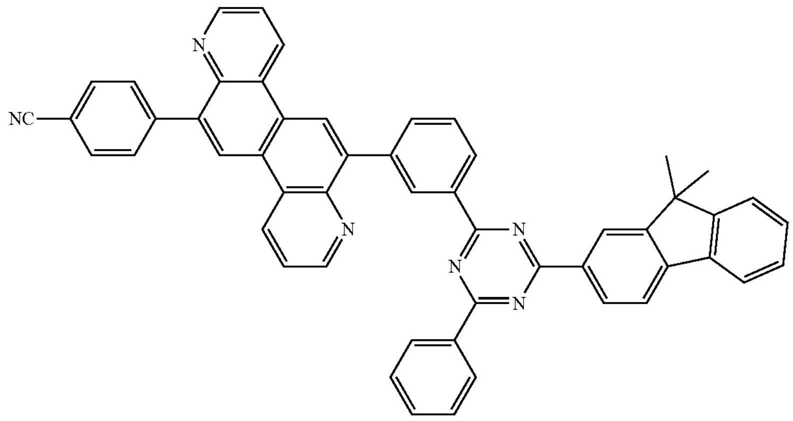
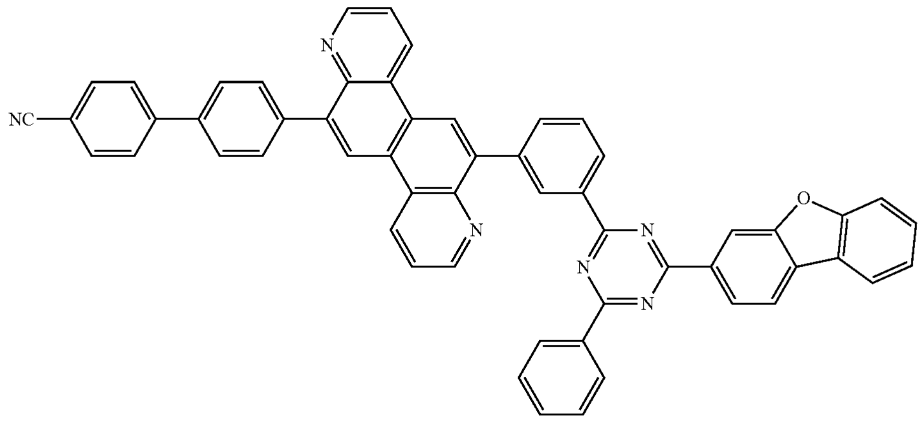
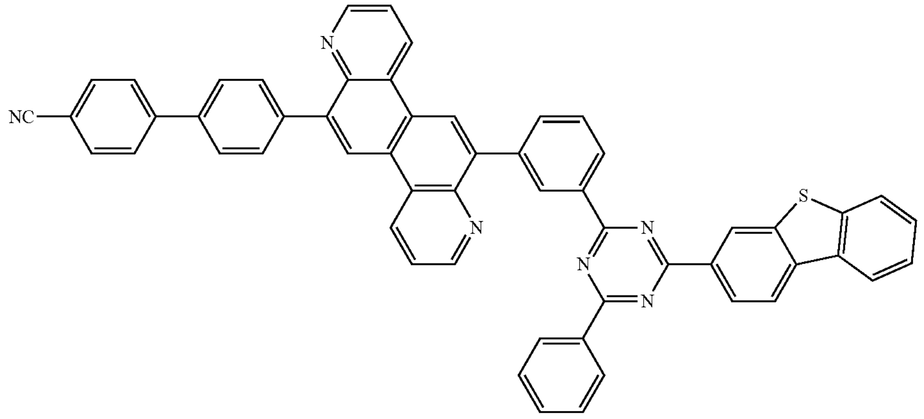
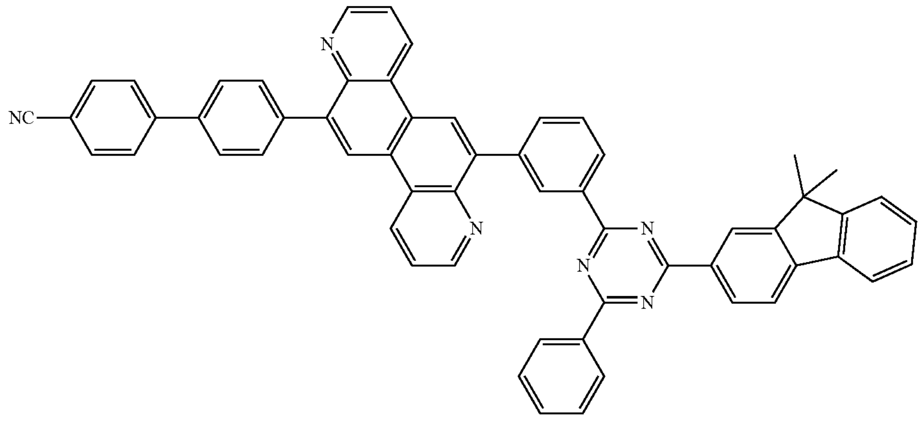

-continued
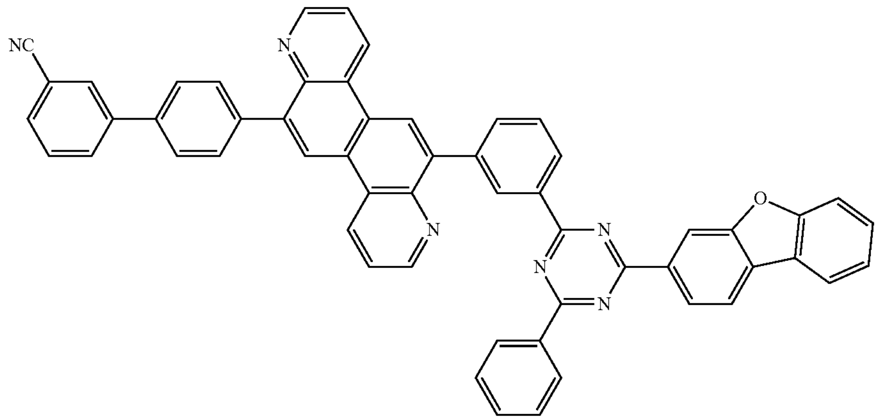
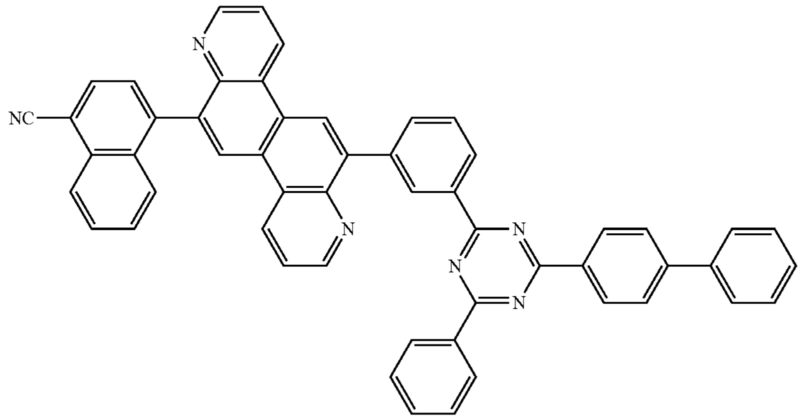
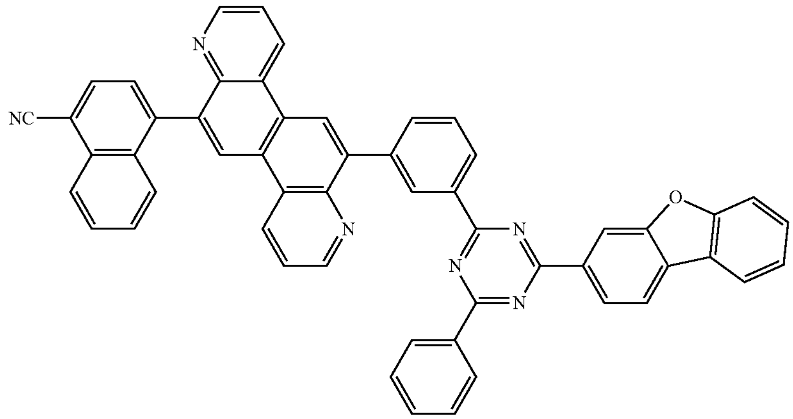
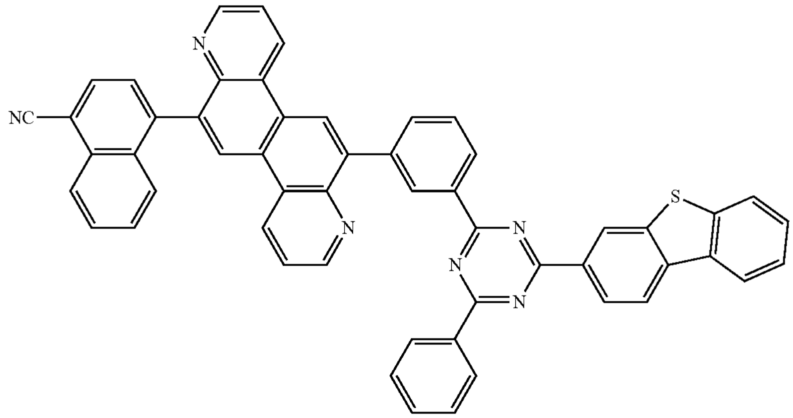

-continued
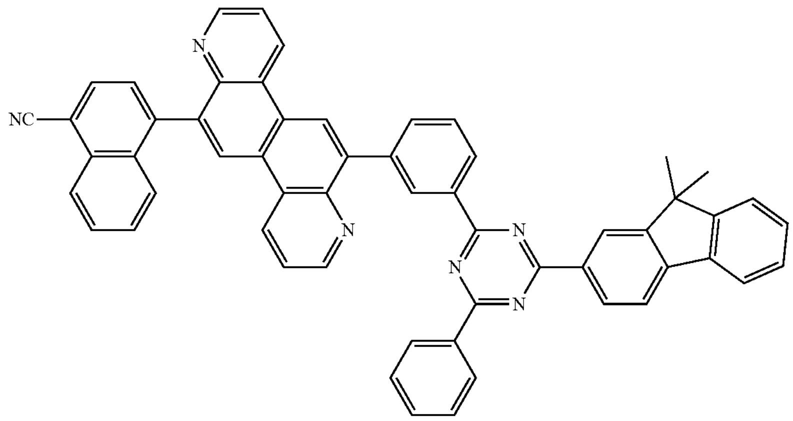
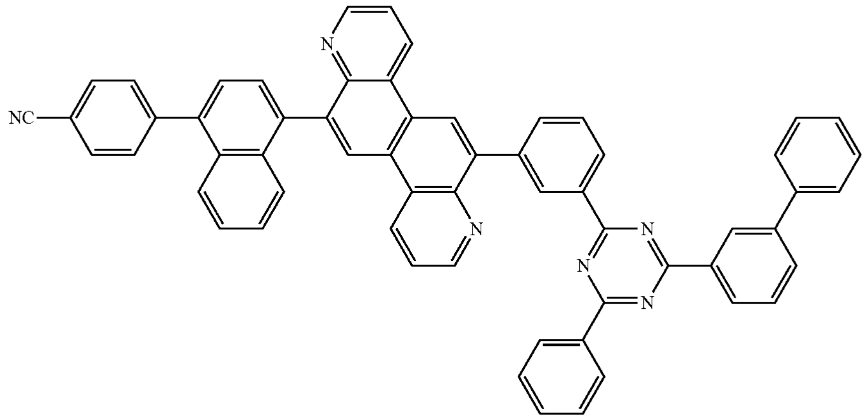
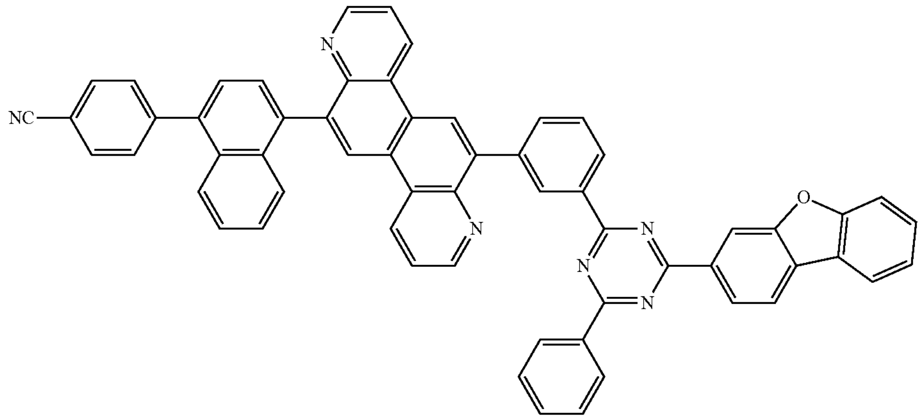
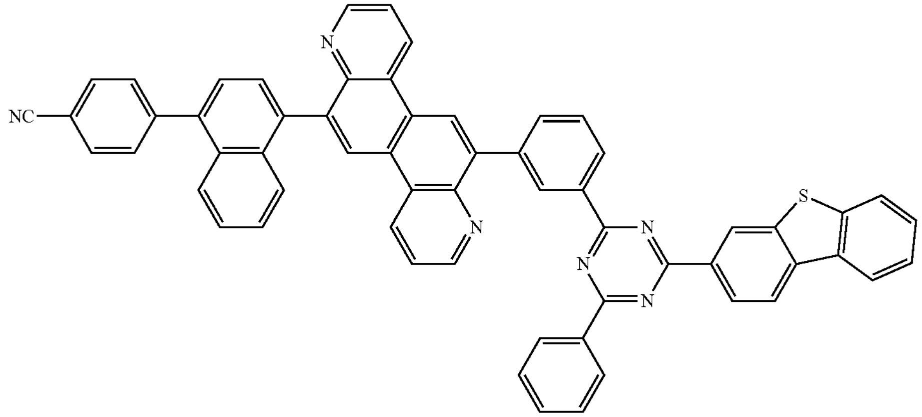

-continued
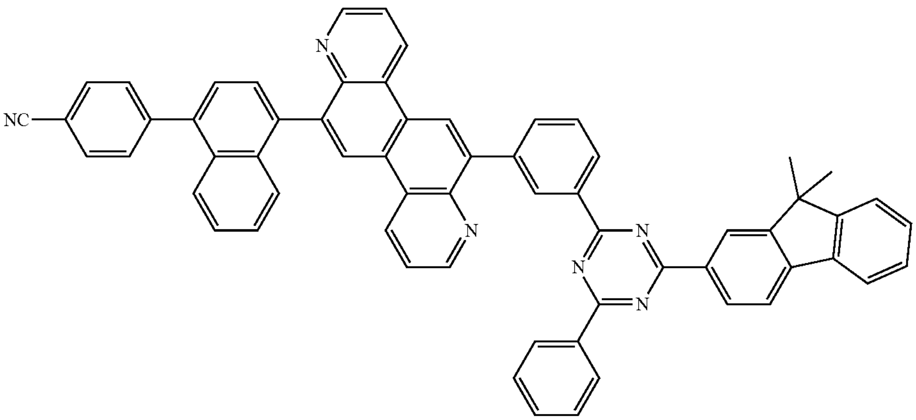
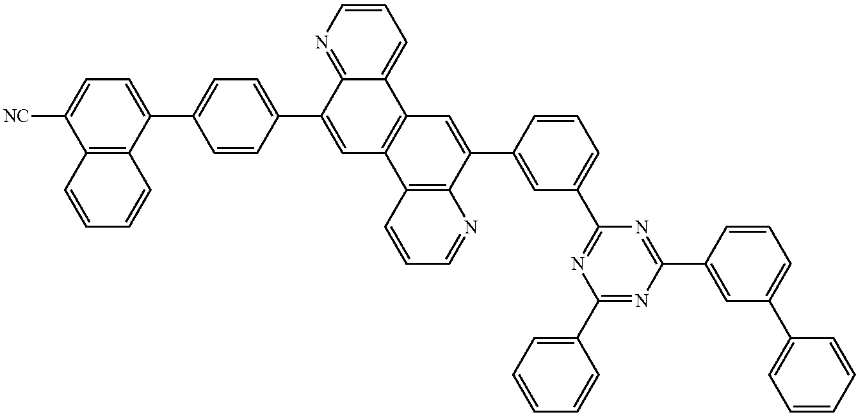
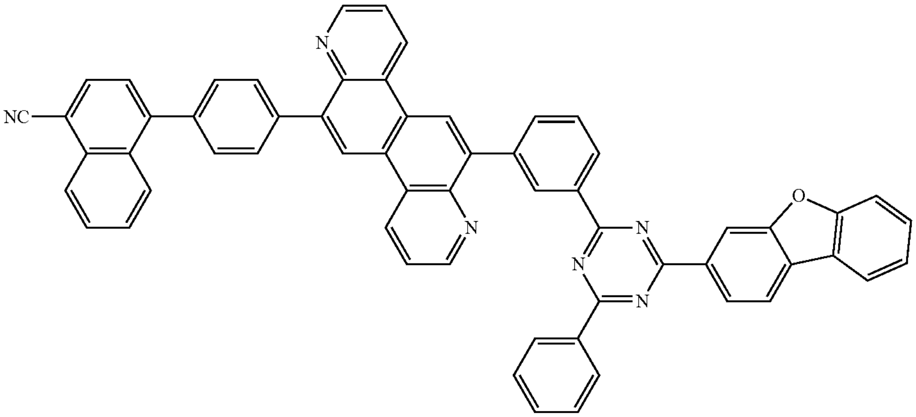
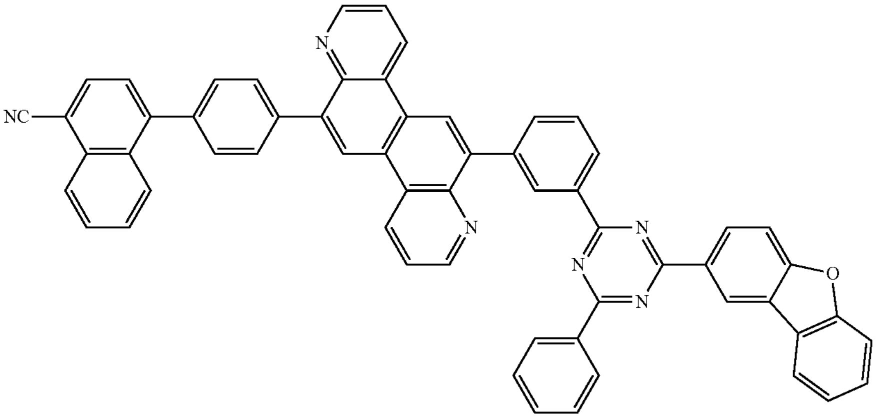

-continued
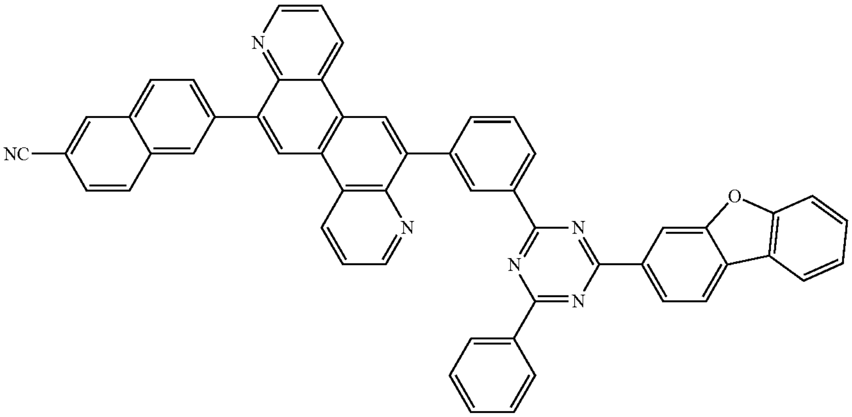
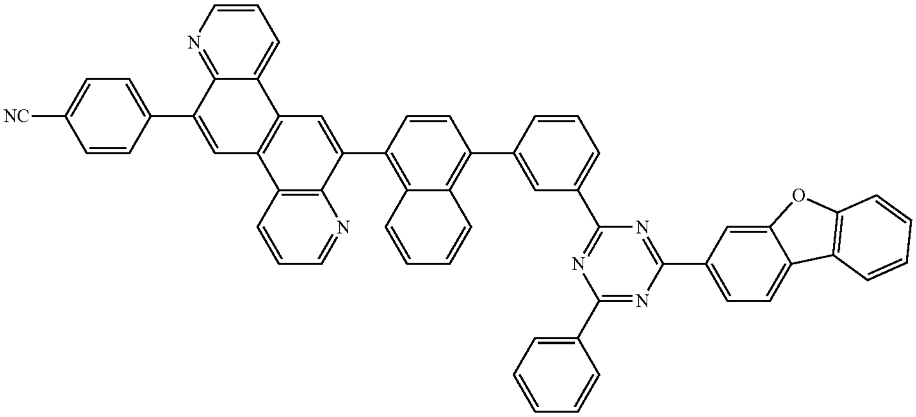
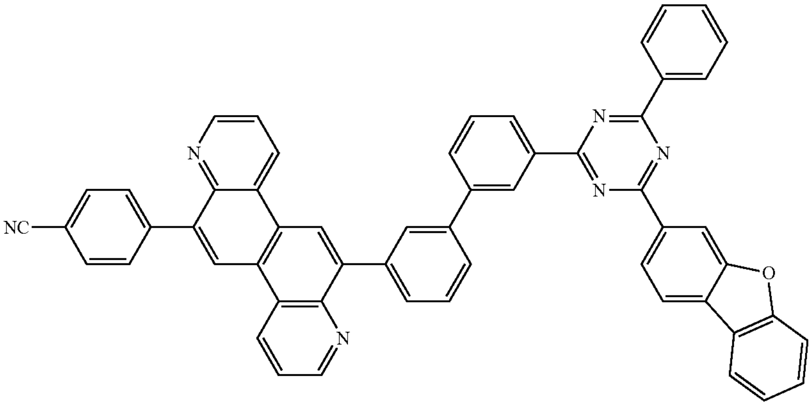
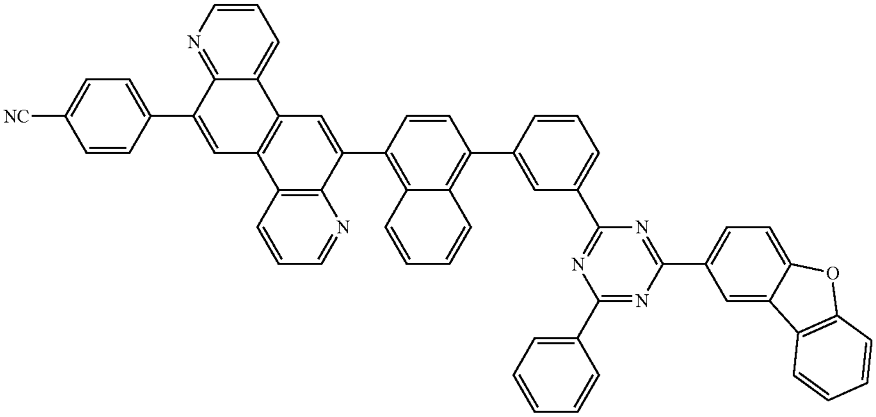

-continued
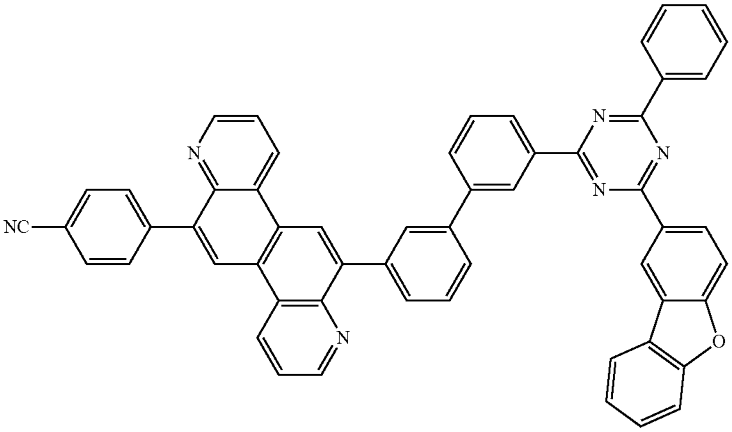
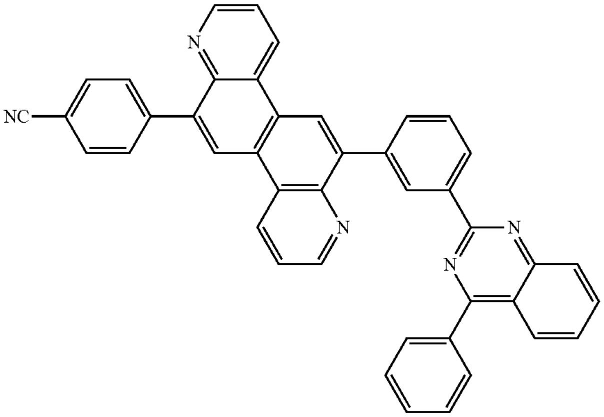
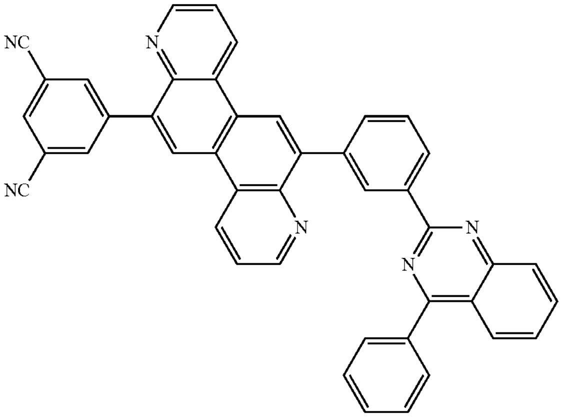
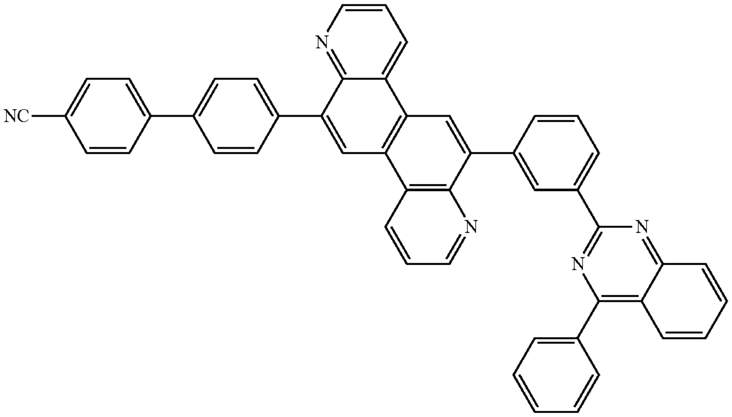
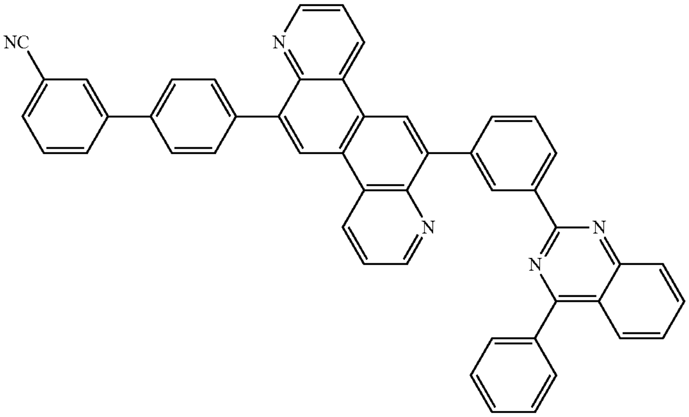

-continued
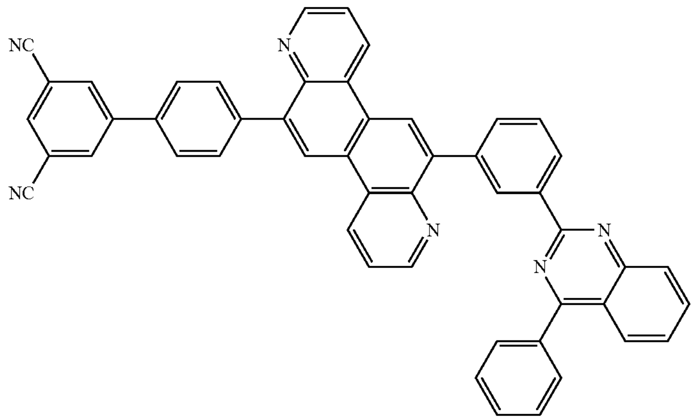
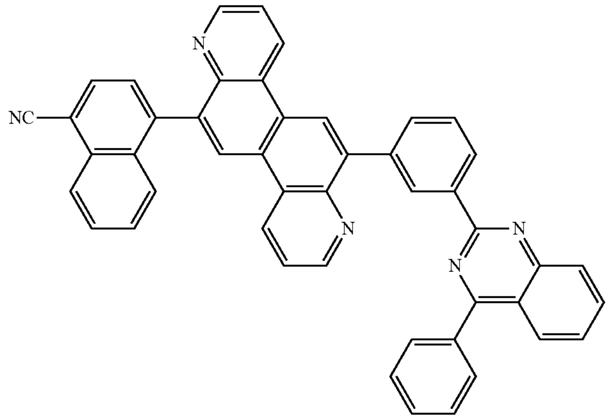
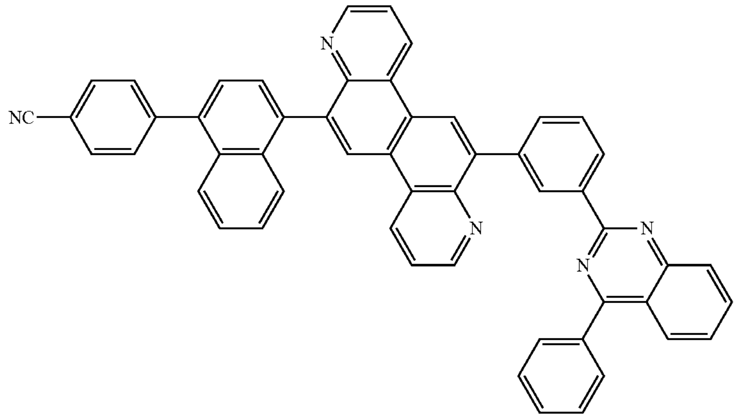
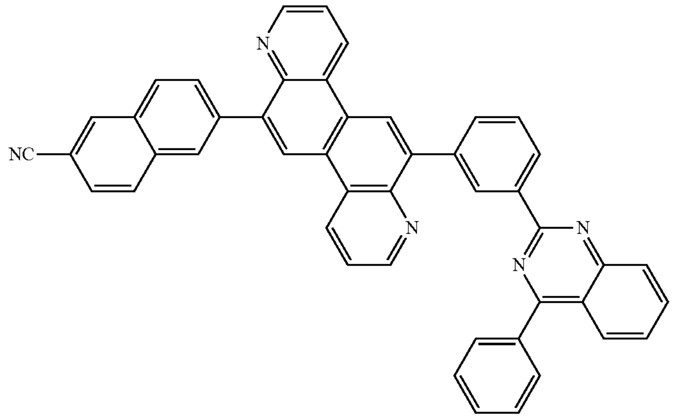

-continued
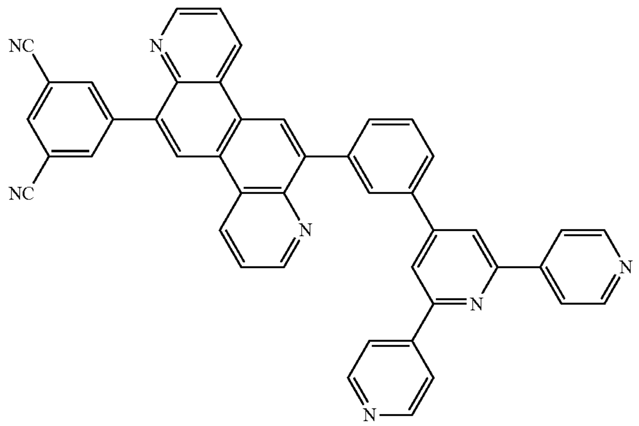
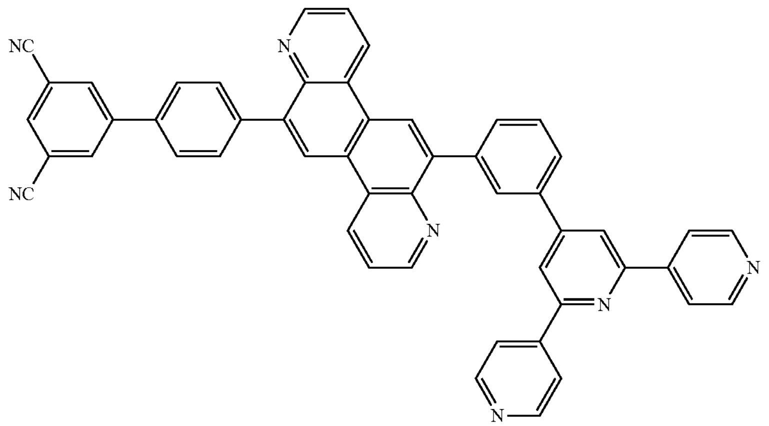
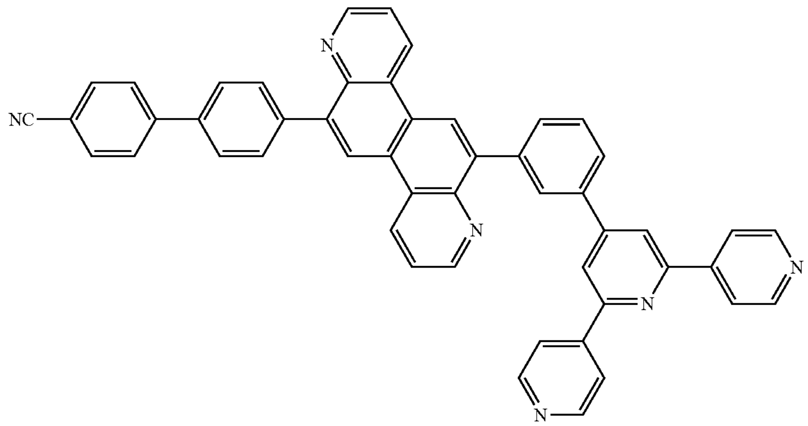
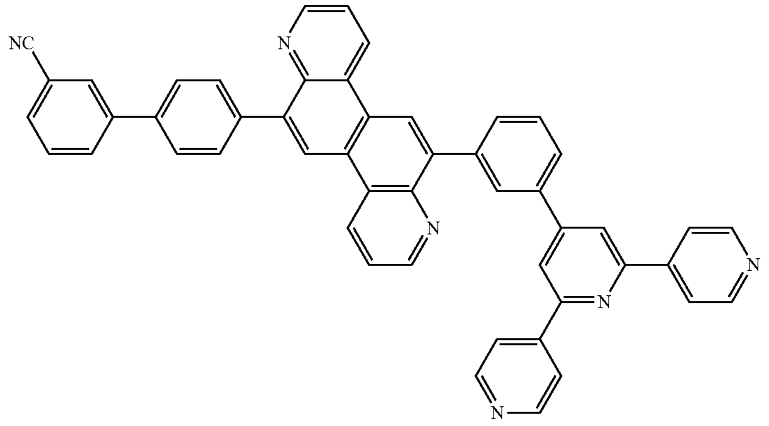

-continued
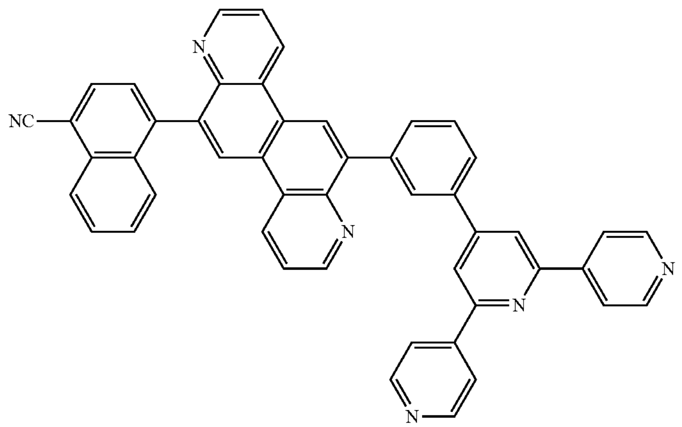
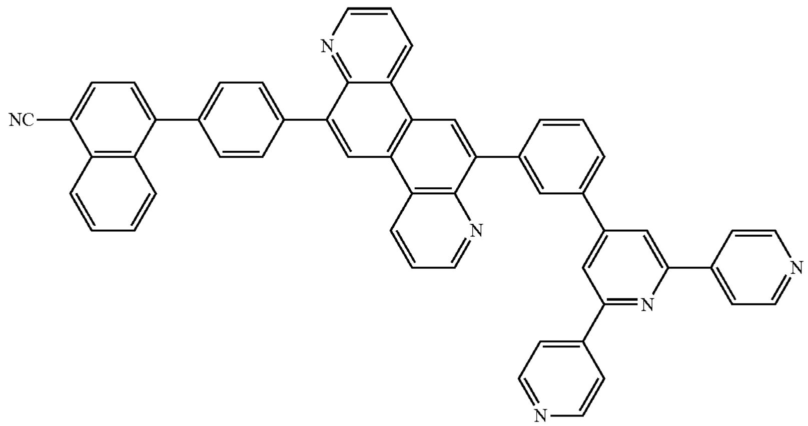
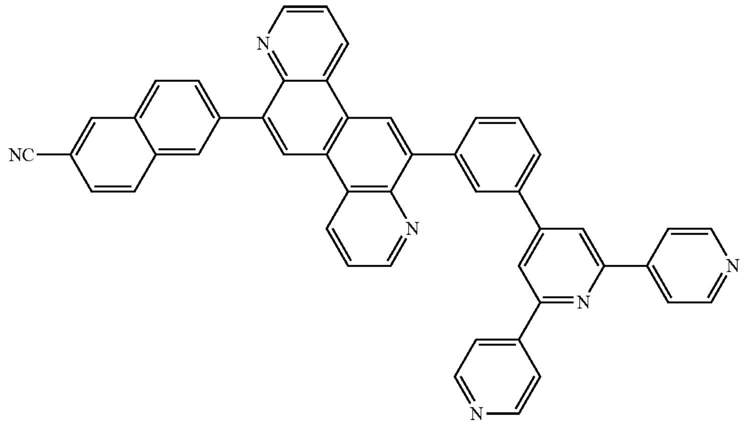
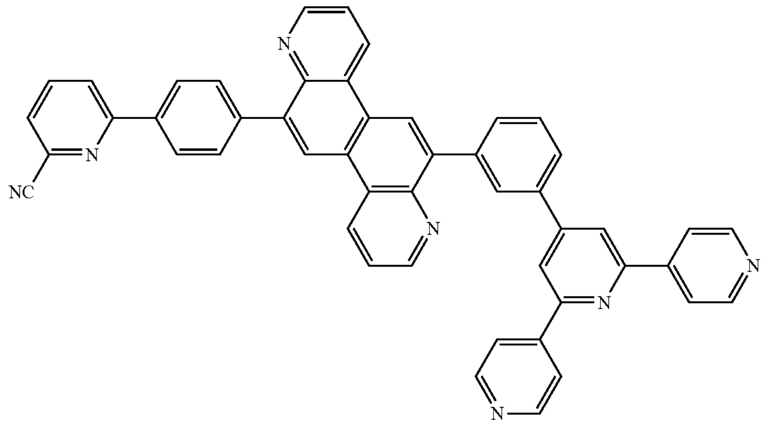

-continued
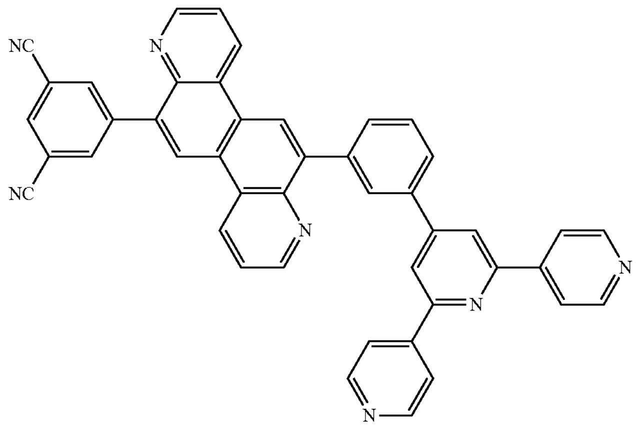
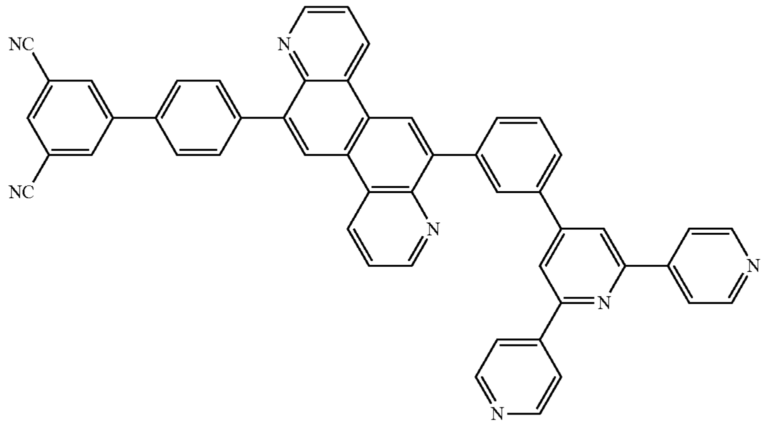
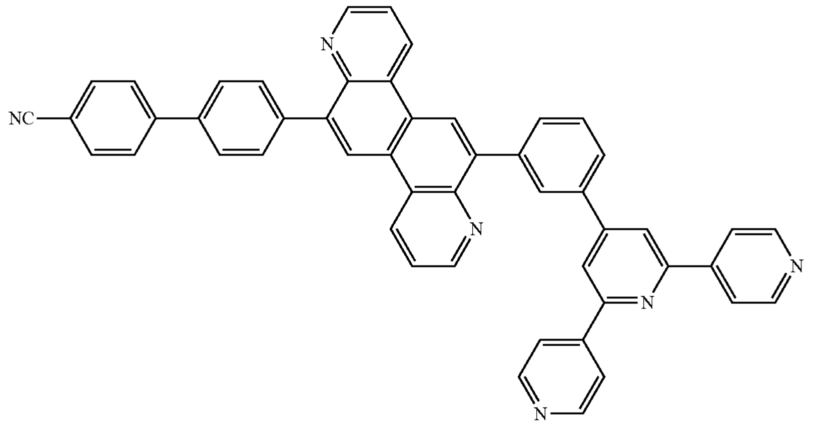
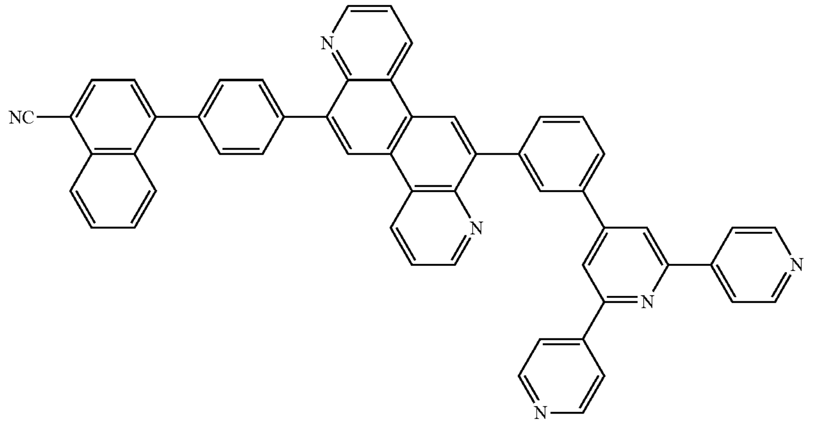

-continued
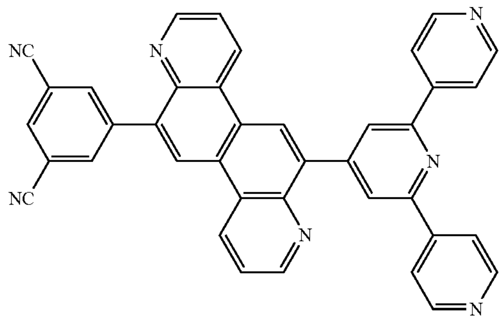
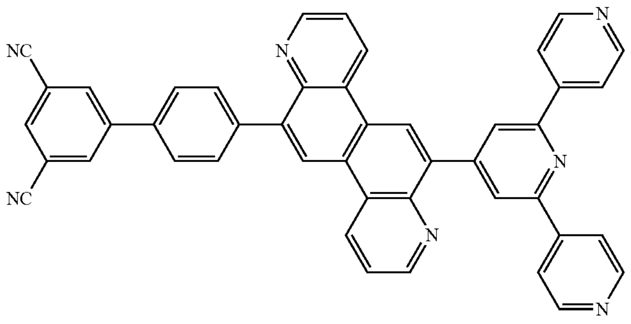
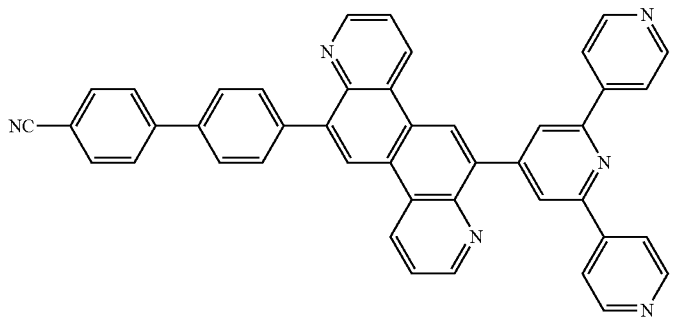
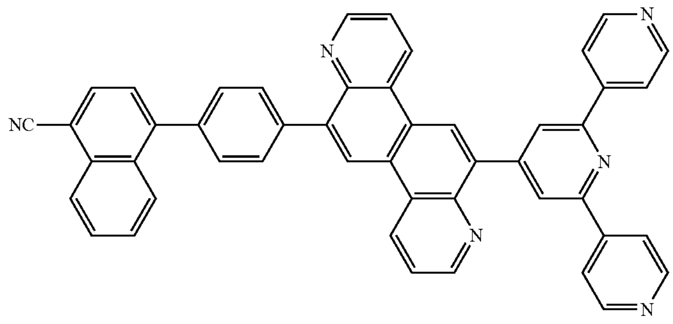
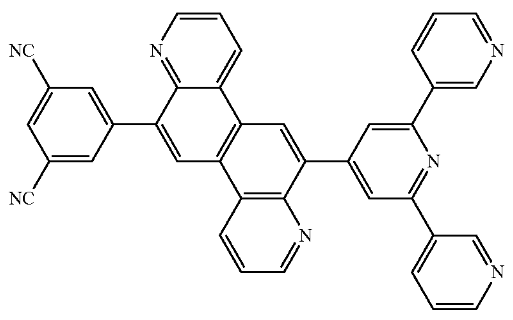
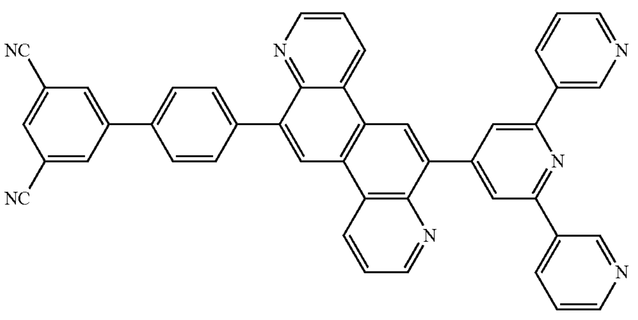

-continued

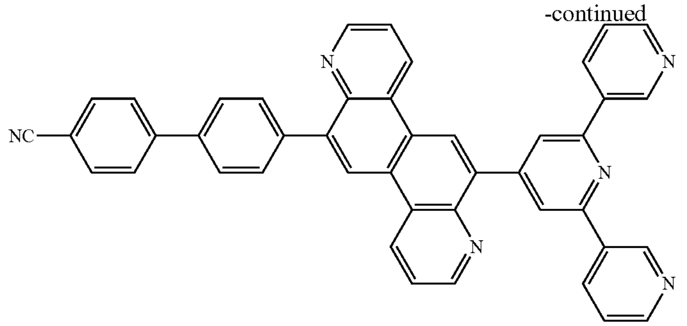

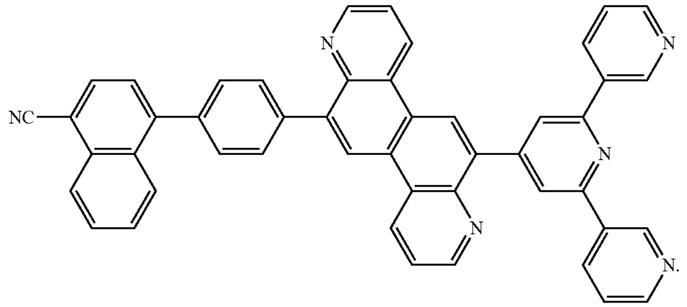 [SMILES: N#Cc1ccc(-c2ccc(-c3cc4c5cccnc5c(-c5cc(-c6cccnc6)nc(-c6cccnc6)c5)cc4c4cccnc34)cc2)c2ccccc12]

A second aspect of the present disclosure is to provide a material of an electron transport layer, wherein the material of the electron transport layer includes the organic compound as described in the first aspect.

A third aspect of the present disclosure is to provide a material of a hole blocking layer, wherein the material of the hole blocking layer includes the organic compound as described in the first aspect.

A fourth aspect of the present disclosure is to provide an OLED device. The OLED device includes an anode, a cathode and an organic thin film layer disposed between the anode and the cathode, wherein a material of the organic thin film layer includes the organic compound as described in the first aspect.

In an embodiment, the organic thin film layer includes an electron transport layer whose material includes at least one of the organic compound as described in the first object.

In an embodiment, the organic thin film layer includes an electron transport layer whose material includes at least one of the organic compound as described in the first object.

In an embodiment, the organic thin film layer includes a hole blocking layer whose material includes the organic compound as described in the first object.

In the OLED device provided by the present disclosure, a material of the anode may be a metal, a metal oxide or a conductive polymer, where the metal includes copper, gold, silver, iron, chromium, nickel, manganese, palladium, platinum and the like as well as alloys thereof, the metal oxide includes indium tin oxide (ITO), indium zinc oxide (IZO), zinc oxide, indium gallium zinc oxide (IGZO) and the like, and the conductive polymer includes polyaniline, polypyrrole, poly(3-methylthiophene) and the like. In addition to the above materials that facilitate hole injection and combinations thereof, the material of the anode further includes known materials suitable for use as the anode.

In the OLED device, a material of the cathode may be a metal or a multilayer metal material, where the metal includes aluminum, magnesium, silver, indium, tin, titanium and the like as well as alloys thereof, and the multilayer metal material includes LiF/Al, $LiO_2$/Al, $BaF_2$/Al and the like. In addition to the above materials that facilitate electron injection and combinations thereof, the material of the cathode further includes known materials suitable for use as the cathode.

In the OLED device, the organic thin film layer includes at least one emissive layer (EML) and any one or a combination of at least two of a hole injection layer (HIL), a hole transport layer (HTL), an electron blocking layer (EBL), a hole blocking layer (HBL), an electron transport layer (ETL) or an electron injection layer (EIL) that are arranged on two sides of the emissive layer. In addition to the organic compound as described in the first object of the present disclosure, the hole/electron injection and transport layers may also include carbazole compounds, arylamine compounds, benzimidazole compounds, metal compounds and the like. The OLED device may further be optionally provided with a capping layer (CPL) disposed on the cathode (on a side of the cathode facing away from the anode).

As shown in the FIGURE, which is a schematic diagram of the OLED device, the OLED device includes an anode 101, a cathode 102 and an emissive layer 103 disposed between the anode 101 and the cathode 102, where a first organic thin film layer 104 and a second organic thin film layer 105 are disposed on two sides of the emissive layer 103. The first organic thin film layer 104 is any one or a combination of at least two of a hole injection layer (HIL), a hole transport layer (HTL) or an electron blocking layer (EBL), and the second organic thin film layer 105 includes any one or a combination of at least two of a hole blocking layer (HBL), an electron transport layer (ETL) or an electron injection layer (EIL). A capping layer (CPL) may further be optionally disposed on the cathode 102 (on a side of the cathode 102 facing away from 105).

The OLED device may be prepared by the following method: forming the anode on a transparent or opaque smooth substrate, forming the organic thin film layer on the anode, and forming the cathode on the organic thin film layer. The organic thin film layer may be formed by using known film forming methods such as evaporation, sputtering, spin coating, impregnation and ion plating.

A fifth aspect of the present disclosure is to provide a display panel. The display panel includes the OLED device as described in the fourth aspect.

A sixth aspect of the present disclosure is to provide an electronic apparatus. The electronic apparatus includes the display panel as described in the fifth aspect.

In the present disclosure, the organic compound having the structure represented by Formula I may be prepared according to the following synthesis route:

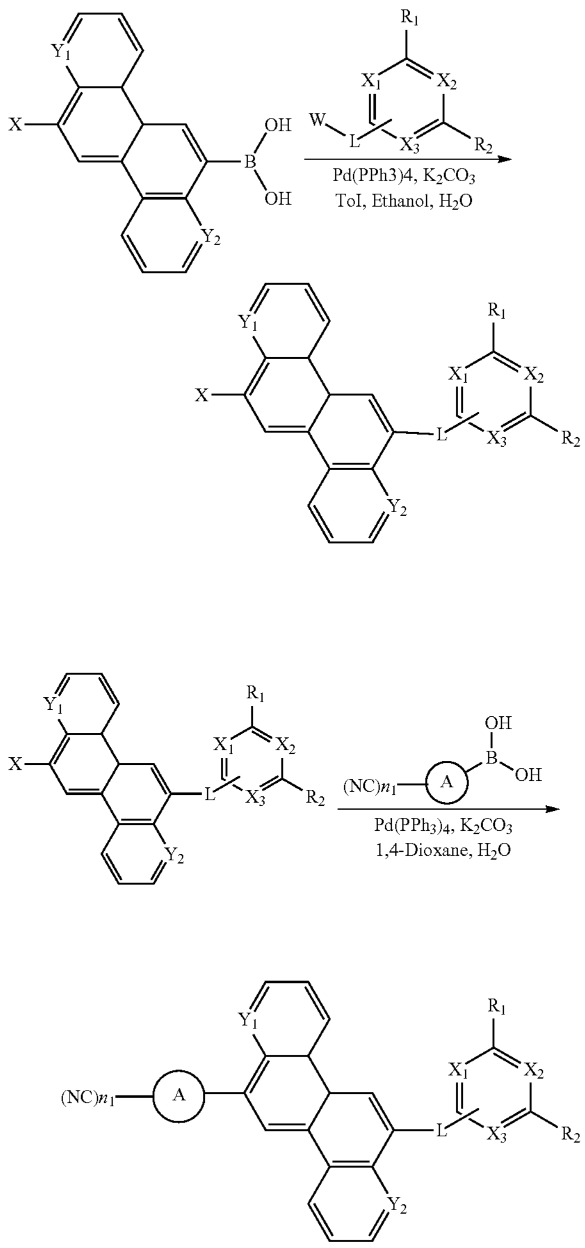

wherein, $X_1$, $X_2$, $X_3$, $Y_1$, $Y_2$, L, $R_1$, $R_2$, A and $n_1$ are defined within the same ranges as in Formula I, and X is selected from halogen (for example, chlorine, bromine or iodine).

Preparation examples of the organic compound of the present disclosure are exemplarily described below.

Preparation Example: Preparation of Compound 1-18

(1)

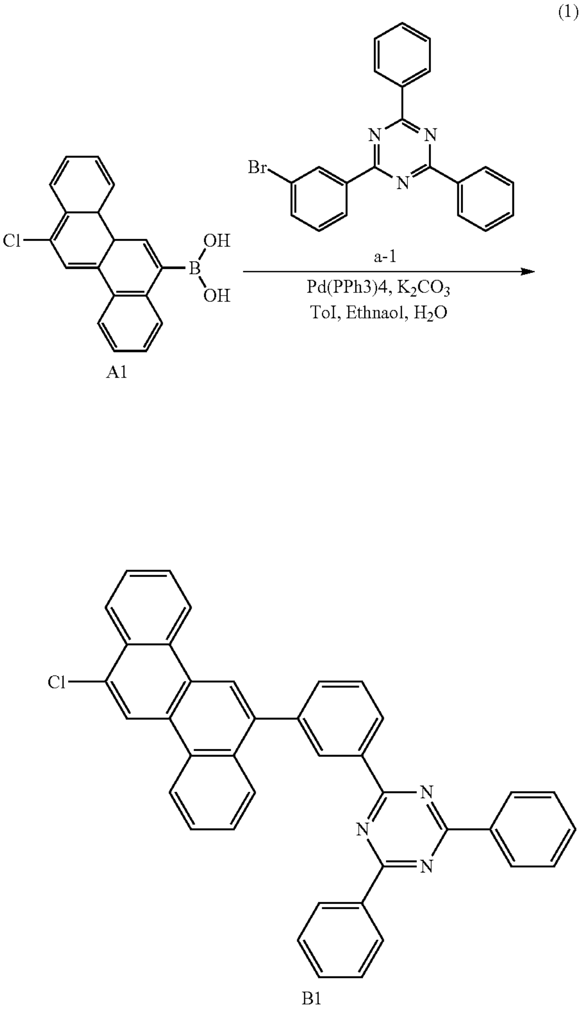

In a nitrogen atmosphere, reaction solvents, toluene, ethanol and water, were added to the reaction flask at a ratio of 7:2:1, and then $K_2CO_3$ (10 mmol) aq, Reactant A1 (5 mmol), Reactant a-1 (5 mmol) and $Pd(PPh_3)_4$ (0.25 mmol) were added in sequence. The system was warmed to 80° C. and reacted overnight. After the reaction was finished, the system was cooled to room temperature, dichloromethane/$H_2O$ were added for extraction, and the collected organic phases were dried over anhydrous $Na_2SO_4$ and suction filtered. The filtrate was collected, the solvents were removed through rotary evaporation, and the product was purified through column chromatography to obtain Intermediate B1 (with a yield of 70%).

MALDI-TOF (m/z): C39H24ClN3: calculated value: 569.17, measured value: 569.38.

(2)

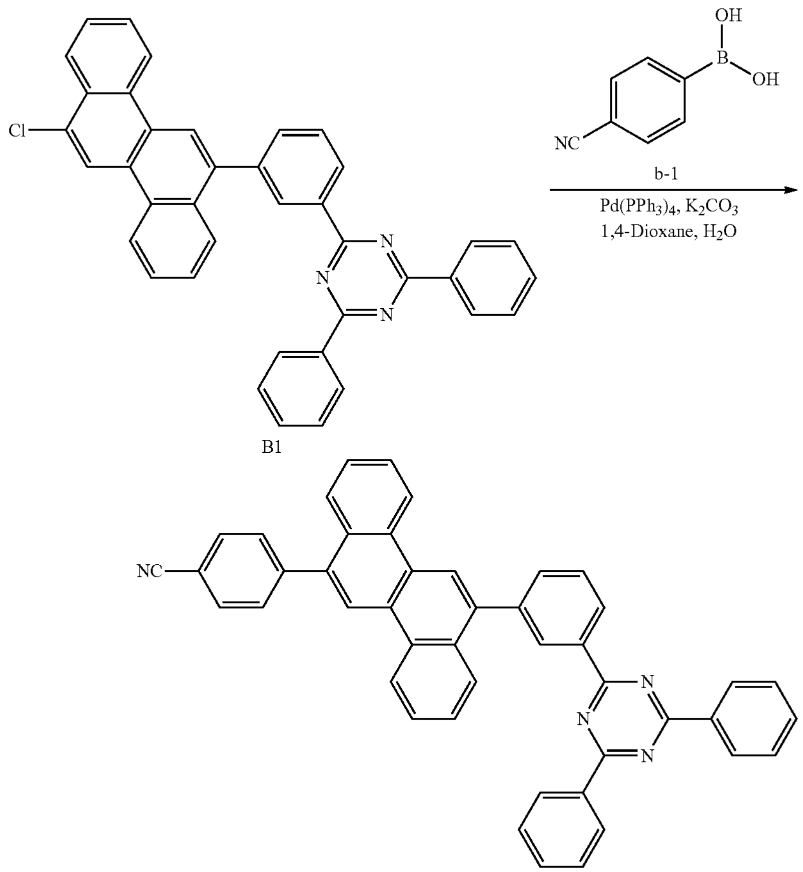

B1

Compound 1

In a nitrogen atmosphere, 1,4-dioxane was added to the reaction flask, and then $K_2CO_3$ (8 mmol) aq, Intermediate B1 (4 mmol), Reactant b-1 (4 mmol) and $Pd(PPh_3)_4$ (0.2 mmol) were added in sequence. The system was warmed to 100° C. and reacted overnight. After the reaction was finished, the system was cooled to room temperature, dichloromethane/$H_2O$ were added for extraction, and the collected organic phases were dried over anhydrous $Na_2SO_4$ and suction filtered. The filtrate was collected, the solvent was removed through rotary evaporation, and the product was purified through column chromatography to obtain Compound 1 (with a yield of 71%).

MALDI-TOF (m/z): C46H28N4: calculated value: 636.23, measured value: 636.45.

Elemental analysis (%): C46H28N4: calculated value: C, 86.77, H, 4.43, N, 8.80; measured value: C, 86.78, H, 4.42, N, 8.82.

The following intermediates/products were synthesized by methods similar to the preceding method.

| Raw Material/Intermediate | Raw Material/Intermediate | Intermediate/Product | Yield (%) | (1) MALDI-TOF (m/z) (2) EA (%) |
|---|---|---|---|---|
| 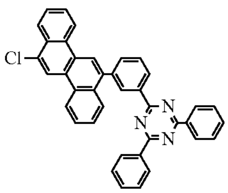 B1 | 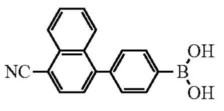 b-2 | 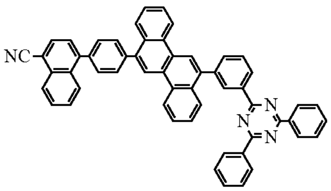 [SMILES: N#Cc1ccc(-c2ccc(-c3cc4c5ccccc5c(-c5cccc(-c6nc(-c7ccccc7)nc(-c7ccccc7)n6)c5)cc4c4ccccc34)cc2)c2ccccc12] Compound 2 | 75 | C56H34N4: (1) calculated value: 762.28, measured value: 762.50; (2) calculated value: C 88.16, H 4.49, N 7.34; |

-continued
| Raw Material/Intermediate | Raw Material/Intermediate | Intermediate/Product | Yield (%) | (1) MALDI-TOF (m/z) (2) EA (%) |
|---|---|---|---|---|
| | | | | measured value: C 88.17, H 4.47, N 7.36. |
| 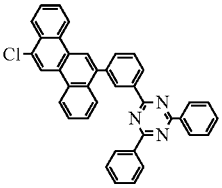 B1 | 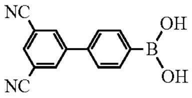 b-3 | 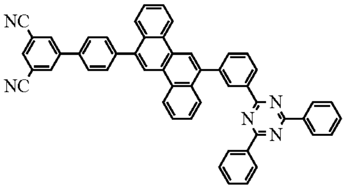 [SMILES: N#Cc1cc(C#N)cc(-c2ccc(-c3cc4c5ccccc5c(-c5cccc(-c6nc(-c7ccccc7)nc(-c7ccccc7)n6)c5)cc4c4ccccc34)cc2)c1] Compound 3 | 72 | C53H31N5: (1) calculated value: 737.26, measured value: 737.47; (2) calculated value: C 86.27, H 4.23, N 9.49; measured value: C 86.28, H 4.22, N 9.51. |
The following intermediates/products were synthesized by methods similar to the preceding method.

| Reaction 1 | | Reaction 2 | | | |
|---|---|---|---|---|---|
| Raw Material 1 | Raw Material 2 | Raw Material 3 | Intermediate/Product | Yield (%) | (1) MALDI-TOF (m/z) (2) EA (%) |
| 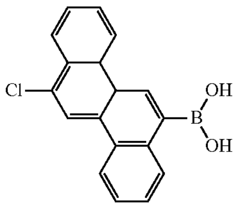 A1 | 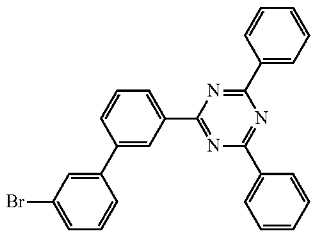 a-2 | 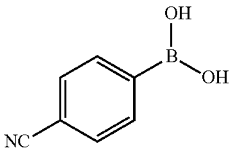 b-1 | 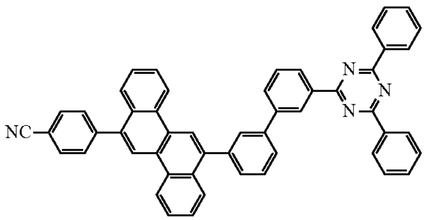 [SMILES: N#Cc1ccc(-c2cc3c4ccccc4c(-c4cccc(-c5cccc(-c6nc(-c7ccccc7)nc(-c7ccccc7)n6)c5)c4)cc3c3ccccc23)cc1] Compound 4 | 72 | $C_{52}H_{32}N_4$: (1) calculated value: 712.26, measured value: 712.56; (2) calculated value: C 87.62, H 4.52, N 7.86; measured value: C 87.64, H 4.51, N 7.87. |
| 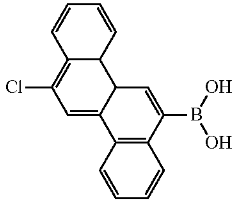 A1 | 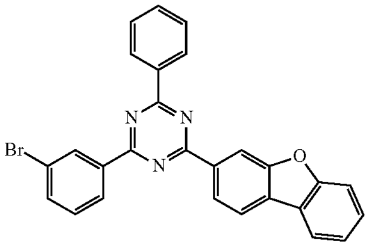 a-3 | 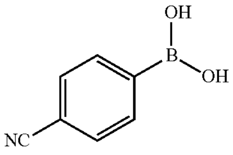 b-1 | 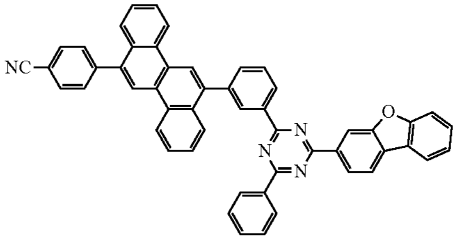 Compound 5 | 71 | $C_{52}H_{30}N_4O$: (1) calculated value: 726.24, measured value: 726.44; (2) calculated value: C 85.93, H 4.16, N 7.71; measured value: C 85.94, H 4.15, N 7.73. |

-continued
| Reaction 1 | | Reaction 2 | | | |
|---|---|---|---|---|---|
| Raw Material 1 | Raw Material 2 | Raw Material 3 | Intermediate/Product | Yield (%) | (1) MALDI-TOF (m/z) (2) EA (%) |
| 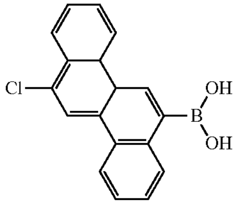 A1 | 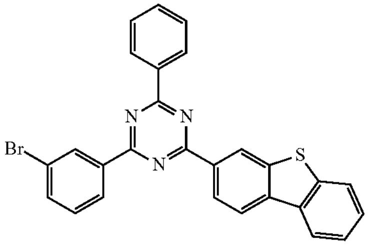 a-4 | 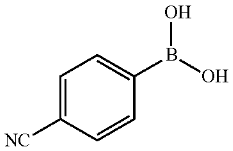 b-1 | 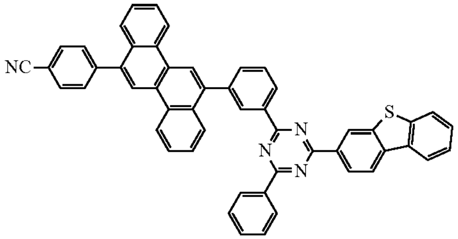 [SMILES: N#Cc1ccc(-c2cc3c4ccccc4c(-c4cccc(-c5nc(-c6ccccc6)nc(-c6ccc7c(c6)sc6ccccc67)n5)c4)cc3c3ccccc23)cc1] Compound 6 | 70 | C52H30N4S: (1) calculated value: 742.22, measured value: 742.52; (2) calculated value: C 84.07, H 4.07, N 7.54; measured value: C 84.08, H 4.06, N 7.56. |

The following intermediates/products were synthesized by methods similar to the preceding method.

| Raw Material/ Intermediate | Raw Material/ Intermediate | Intermediate/Product | Yield (%) | (1) MALDI-TOF (m/z) (2) EA (%) |
|---|---|---|---|---|
| 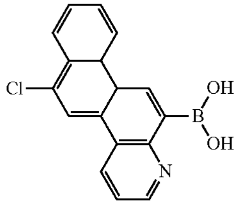 A2 | 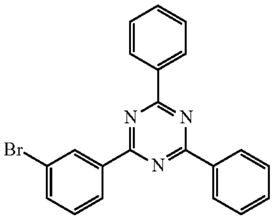 a-1 | 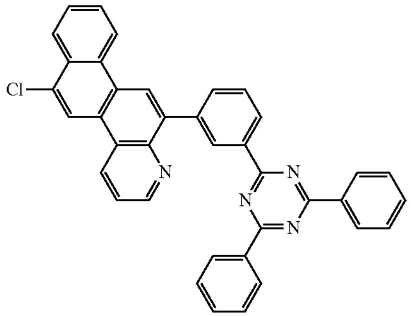 B2 | 72 | C38H23ClN4: (1) calculated value: 570.16, measured value: 570.36. |
| 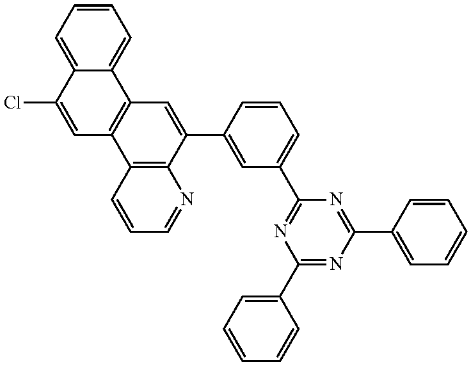 B2 | 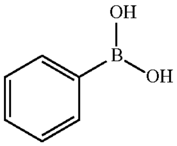 c-1 | 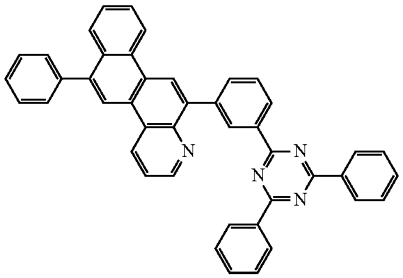 Compound 7 | 78 | C44H28N4: (1) calculated value: 612.23, measured value: 612.45; (2) calculated value: C 86.25, H 4.61, N 9.14; measured value: C 86.26, H 4.60, N 9.16. |

-continued
| Raw Material/ Intermediate | Raw Material/ Intermediate | Intermediate/Product | Yield (%) | (1) MALDI-TOF (m/z) (2) EA (%) |
|---|---|---|---|---|
| 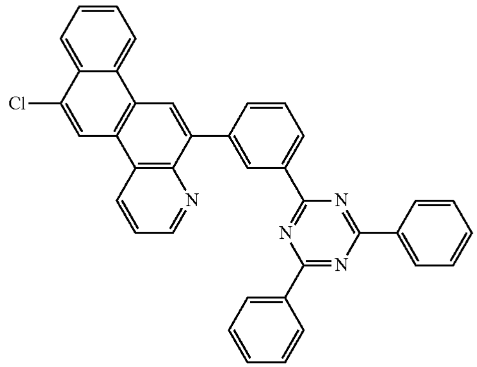 B2 | 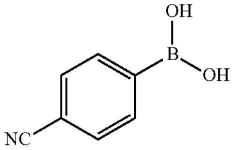 b-1 | 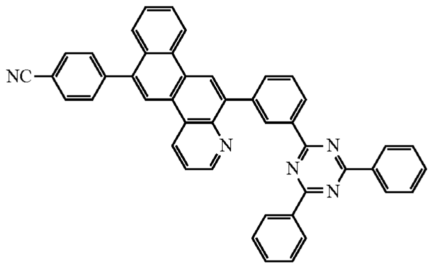 [SMILES: N#Cc1ccc(-c2cc3c4cccnc4c(-c4cccc(-c5nc(-c6ccccc6)nc(-c6ccccc6)n5)c4)cc3c3ccccc23)cc1] Compound 8 | 74 | C45H27N5: (1) calculated value: 637.23, measured value: 637.51; (2) calculated value: C 84.75, H 4.27, N 10.98; measured value: C 84.76, H 4.26, N 11.00. |
| 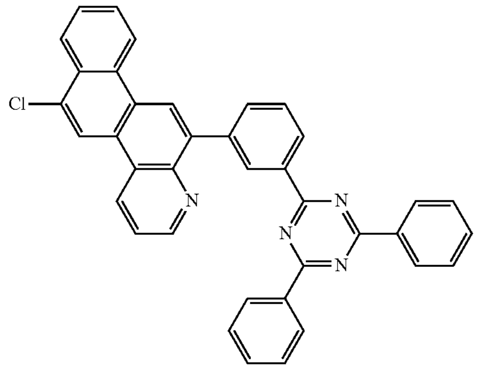 B2 | 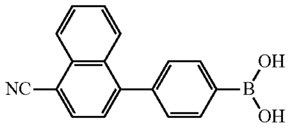 b-2 | 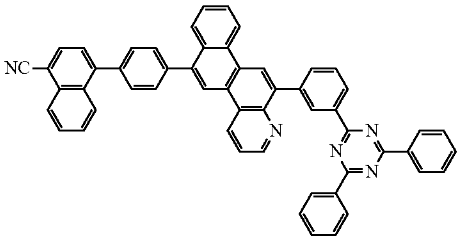 [SMILES: N#Cc1ccc(-c2ccc(-c3cc4c5cccnc5c(-c5cccc(-c6nc(-c7ccccc7)nc(-c7ccccc7)n6)c5)cc4c4ccccc34)cc2)c2ccccc12] Compound 9 | 76 | C55H33N5: (1) calculated value: 763.27, measured value: 763.57; (2) calculated value: C 86.48, H 4.35, N 9.17; measured value: C 86.49, H 4.34, N 9.19. |

-continued
| Raw Material/ Intermediate | Raw Material/ Intermediate | Intermediate/Product | Yield (%) | (1) MALDI-TOF (m/z) (2) EA (%) |
|---|---|---|---|---|
| 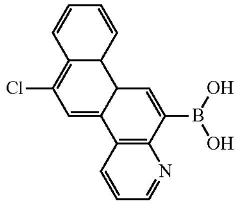 A2 | 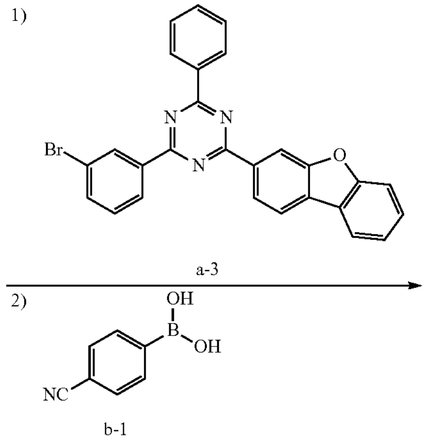 [SMILES: Brc1cccc(-c2nc(-c3ccccc3)nc(-c3ccc4c(c3)oc3ccccc34)n2)c1 ; N#Cc1ccc(B(O)O)cc1] | 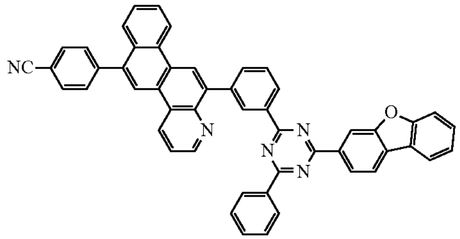 [SMILES: N#Cc1ccc(-c2cc3c4cccnc4c(-c4cccc(-c5nc(-c6ccccc6)nc(-c6ccc7c(c6)oc6ccccc67)n5)c4)cc3c3ccccc23)cc1] Compound 10 | 72 | $C_{51}H_{29}N_5O$: (1) calculated value: 727.24, measured value: 727.46; (2) calculated value: C 84.16, H 4.02, N 9.62; measured value: C 84.17, H 4.01, N 9.64. |

| Raw Material/ Intermediate | Raw Material/ Intermediate | Intermediate/Product | Yield (%) | (1) MALDI-TOF (m/z) (2) EA (%) |
|---|---|---|---|---|
| 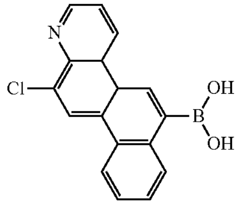 A3 | 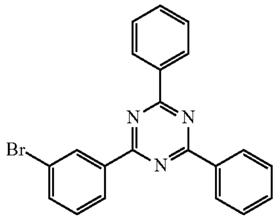 a-1 | 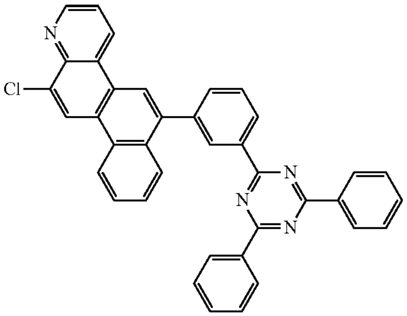 B3 | 73 | C38H23ClN4: (1) calculated value: 570.16, measured value: 570.46. |
| 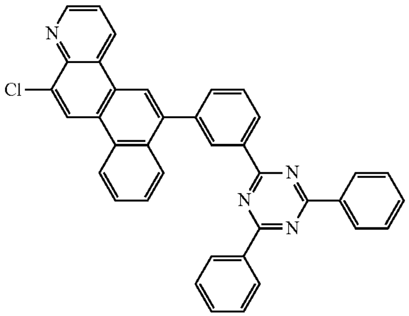 B3 | 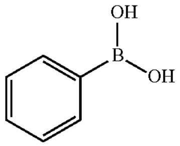 c-1 | 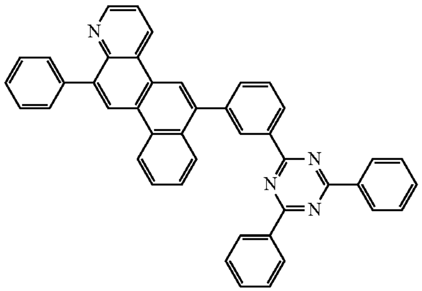 Compound 11 | 79 | C44H28N4: (1) calculated value: 612.23, measured value: 612.43; (2) calculated value: C 86.25, H 4.61, N 9.14; measured value: C 86.26, H 4.60, N 9.16. |

-continued
| Raw Material/ Intermediate | Raw Material/ Intermediate | Intermediate/Product | Yield (%) | (1) MALDI-TOF (m/z) (2) EA (%) |
|---|---|---|---|---|
| 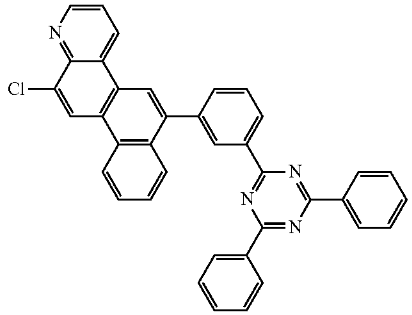 B3 | 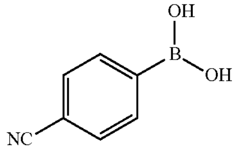 b-1 | 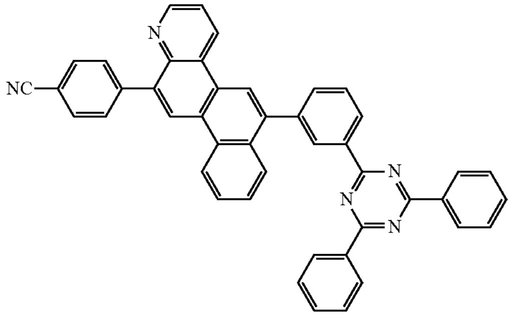 [SMILES: N#Cc1ccc(-c2cc3c4ccccc4c(-c4cccc(-c5nc(-c6ccccc6)nc(-c6ccccc6)n5)c4)cc3c3cccnc23)cc1] Compound 12 | 75 | C45H27N5: (1) calculated value: 637.23, measured value: 637.50; (2) calculated value: C 84.75, H 4.27, N 10.98; measured value: C 84.76, H 4.26, N 10.99. |
| 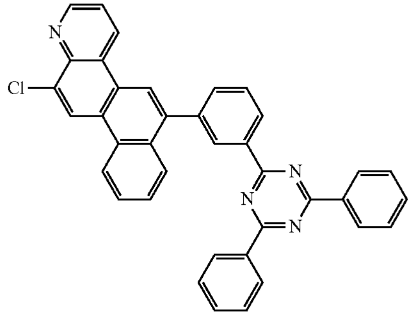 B3 | 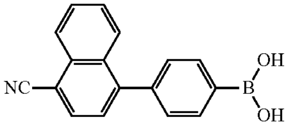 b-2 | 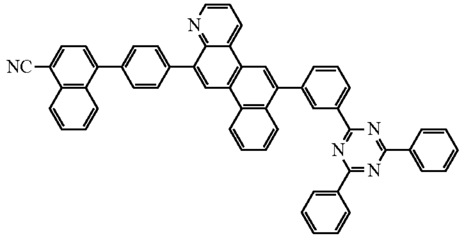 [SMILES: N#Cc1ccc(-c2ccc(-c3cc4c5ccccc5c(-c5cccc(-c6nc(-c7ccccc7)nc(-c7ccccc7)n6)c5)cc4c4cccnc34)cc2)c2ccccc12] Compound 13 | 77 | C55H33N5: (1) calculated value: 763.27, measured value: 763.57; (2) calculated value: C 86.48, H 4.35, N 9.17; measured value: C 86.49, H 4.34, N 9.19. |

-continued
| Raw Material/ Intermediate | Raw Material/ Intermediate | Intermediate/Product | Yield (%) | (1) MALDI-TOF (m/z) (2) EA (%) |
|---|---|---|---|---|
| 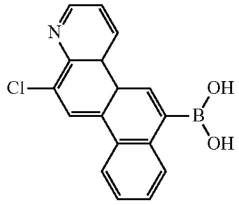 A3 | 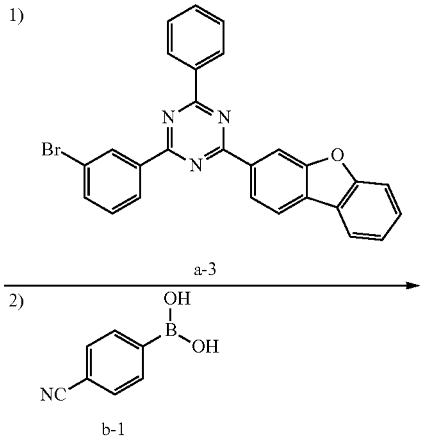 [SMILES: Brc1cccc(-c2nc(-c3ccccc3)nc(-c3ccc4c(c3)oc3ccccc34)n2)c1 ; N#Cc1ccc(B(O)O)cc1] | 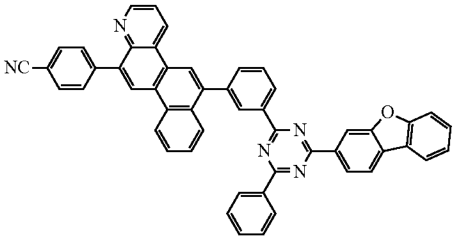 Compound 14 | 73 | C51H29N5O: (1) calculated value: 727.24, measured value: 727.54; (2) calculated value: C 84.16, H 4.02, N 9.62; measured value: C 84.17, H 4.01, N 9.64. |

The following intermediates/products were synthesized by methods similar to the preceding method.

| Raw Material/ Intermediate | Raw Material/ Intermediate | Intermediate/Product | Yield (%) | (1) MALDI-TOF (m/z) (2) EA (%) |
|---|---|---|---|---|
| 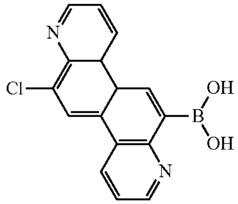 A4 | 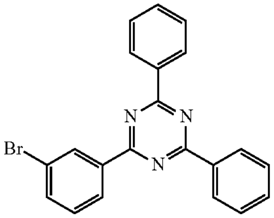 a-1 | 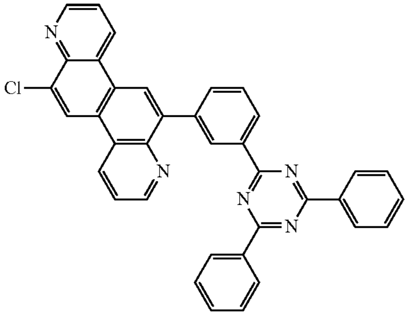 B4 | 72 | C37H22ClN5: (1) calculated value: 571.16, measured value: 571.45. |
| 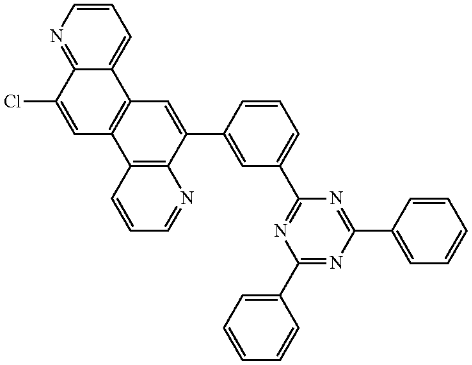 B4 | 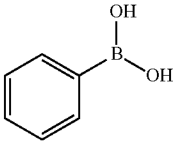 c-1 | 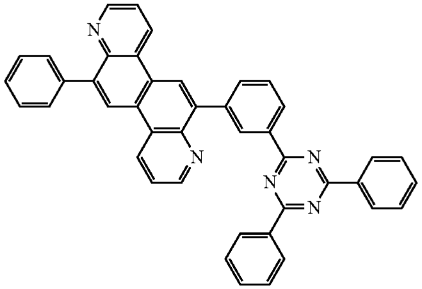 Compound 15 | 79 | C43H27N5: (1) calculated value: 613.23, measured value: 613.43; (2) calculated value: C 84.15, H 4.43, N 11.41; measured value: C 84.16, H 4.42, N 11.43. |

-continued
| Raw Material/ Intermediate | Raw Material/ Intermediate | Intermediate/Product | Yield (%) | (1) MALDI-TOF (m/z) (2) EA (%) |
|---|---|---|---|---|
| 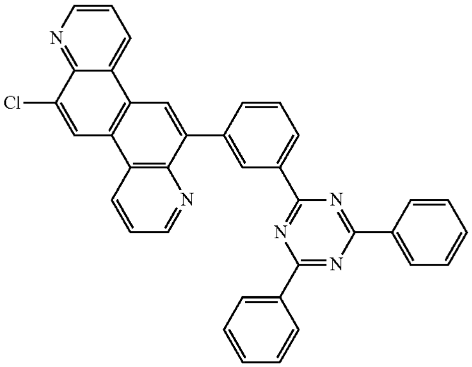 B4 | 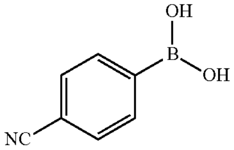 b-1 | 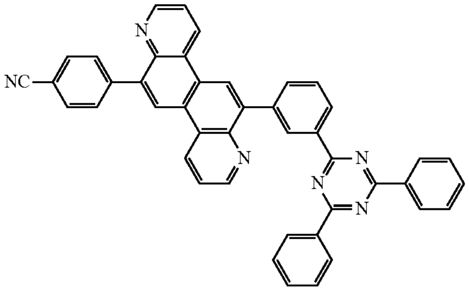 Compound 16 | 75 | C44H26N6: (1) calculated value: 638.22, measured value: 638.50; (2) calculated value: C 82.74, H 4.10, N 13.16; measured value: C 82.75, H 4.09, N 13.18. |
| 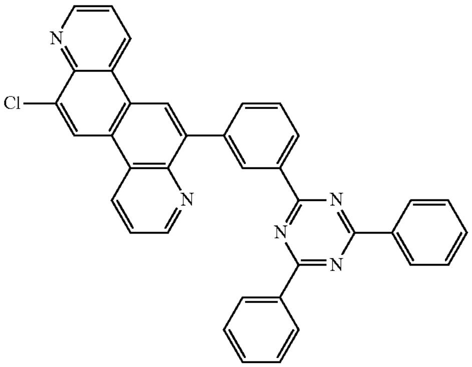 B4 | 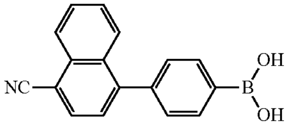 b-2 | 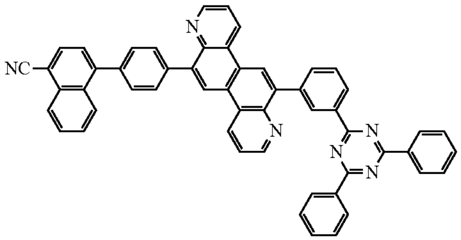 Compound 17 | 77 | C54H32N6: (1) calculated value: 764.27, measured value: 764.47; (2) calculated value: C 84.80, H 4.22, N 10.99; measured value: C 84.81, H 4.21, N 11.01. |

-continued
| Raw Material/ Intermediate | Raw Material/ Intermediate | Intermediate/Product | Yield (%) | (1) MALDI-TOF (m/z) (2) EA (%) |
|---|---|---|---|---|
| 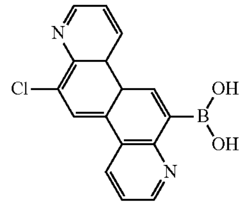 A4 | 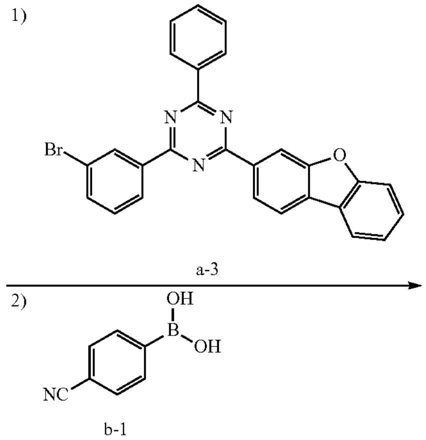 [SMILES: Brc1cccc(-c2nc(-c3ccccc3)nc(-c3ccc4c(c3)oc3ccccc34)n2)c1 ; N#Cc1ccc(B(O)O)cc1] | 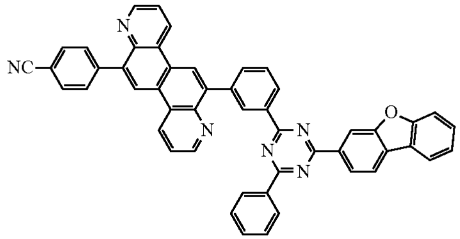 [SMILES: N#Cc1ccc(-c2cc3c4cccnc4c(-c4cccc(-c5nc(-c6ccccc6)nc(-c6ccc7c(c6)oc6ccccc67)n5)c4)cc3c3cccnc23)cc1] Compound 18 | 74 | C50H28N6O: (1) calculated value: 728.23, measured value: 728.53; (2) calculated value: C 82.40, H 3.87, N 11.53; measured value: C 82.41, H 3.86, N 11.55. |

Simulated Calculations of Energy Levels of Compounds

By use of a density-functional theory (DFT), the distribution of molecular frontier orbital HOMO and LUMO was optimized and calculated for the organic compounds provided in the examples of the present disclosure using a Guassian 09 package (Guassian Inc.) at a calculation level of B3LYP/6-31G(d). Meanwhile, based on a time-dependent density-functional theory (TDDFT), the lowest singlet energy level S1 and the lowest triplet energy level T1 of molecules of the compounds were simulated and calculated. Results are shown in Table 1.

TABLE 1

| Compound | HOMO (eV) | LUMO (eV) | $E_{S1}$ (eV) | $E_{T1}$ (eV) |
|---|---|---|---|---|
| Compound 1 | −5.62 | −1.94 | 3.27 | 2.34 |
| Compound 2 | −5.55 | −1.92 | 3.26 | 2.34 |
| Compound 3 | −5.51 | −1.98 | 3.23 | 2.34 |
| Compound 4 | −5.60 | −1.93 | 3.27 | 2.34 |
| Compound 5 | −5.61 | −1.98 | 3.27 | 2.34 |
| Compound 6 | −5.60 | −1.98 | 3.27 | 2.34 |
| Compound 7 | −5.50 | −1.76 | 3.33 | 2.33 |
| Compound 8 | −5.66 | −1.96 | 3.29 | 2.33 |
| Compound 9 | −5.62 | −1.94 | 3.28 | 2.33 |
| Compound 10 | −5.67 | −1.98 | 3.28 | 2.33 |
| Compound 11 | −5.51 | −1.78 | 3.33 | 2.33 |
| Compound 12 | −5.64 | −1.98 | 3.27 | 2.32 |
| Compound 13 | −5.61 | −1.96 | 3.26 | 2.32 |
| Compound 14 | −5.65 | −1.99 | 3.26 | 2.32 |
| Compound 15 | −5.53 | −1.80 | 3.33 | 2.34 |
| Compound 16 | −5.78 | −1.98 | 3.24 | 2.30 |
| Compound 17 | −5.76 | −1.97 | 3.23 | 2.30 |
| Compound 18 | −5.79 | −1.99 | 3.23 | 2.30 |

As can be seen from Table 1, the compounds provided by the present disclosure have relatively deep LUMO energy levels (−1.76 to −1.99 eV) and can reduce a potential barrier of electron transport, improve an electron injection ability, and effectively reduce the voltage of an OLED device. Such compounds all have relatively deep HOMO energy levels (−5.50 to −5.79 eV) and can effectively block holes so that more holes and electrons are recombined in a light-emitting region, which can achieve higher luminescence efficiency.

Application examples in which the organic compounds of the present disclosure are applied to the OLED device are described below.

Application Example 1

This application example provides an OLED device whose structure is shown in the FIGURE. The OLED device includes a substrate 1, an anode 2, a hole injection layer 3, a hole transport layer 4, an electron blocking layer 5, an emissive layer 6, a hole blocking layer 7, an electron transport layer 8, an electron injection layer 9 and a cathode 10 which are stacked in sequence. An arrow in the FIGURE represents a light-emitting direction of the device.

The OLED device was prepared by specific steps described below.

(1) A glass substrate 1 having an indium tin oxide (ITO) anode 2 (with a thickness of 100 nm) was sonicated in isopropyl alcohol and deionized water for 30 minutes separately and cleaned under ozone for about 10 minutes. The cleaned glass substrate was installed onto a vacuum deposition apparatus.

(2) On the ITO anode 2, Compound a was deposited through vacuum evaporation as the hole injection layer 3 with a thickness of 10 nm.

(3) On the hole injection layer 3, Compound b was deposited through vacuum evaporation as the hole transport layer 4 with a thickness of 40 nm.

(4) On the hole transport layer 4, Compound c was deposited through vacuum evaporation as the electron blocking layer 5 with a thickness of 10 nm.

(5) On the electron blocking layer 5, Compound d and Compound e were co-deposited through vacuum evaporation at a doping proportion of 5% (mass ratio) as the emissive layer 6 with a thickness of 20 nm.

(6) On the emissive layer 6, Compound f was deposited through vacuum evaporation as the hole blocking layer 7 with a thickness of 10 nm.

(7) On the hole blocking layer 7, Compound 1 in Preparation Example 1 was deposited through vacuum evaporation as the electron transport layer 8 with a thickness of 30 nm.

(8) On the electron transport layer 8, Compound LiF was deposited through vacuum evaporation as the electron injection layer 9 with a thickness of 2 nm.

(9) On the electron injection layer 9, an aluminum electrode was deposited through vacuum evaporation as the cathode 10 with a thickness of 100 nm.

The compounds used for preparing the OLED device are as follows:

Compound a

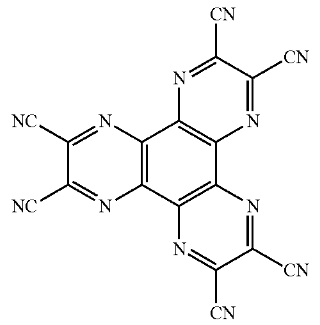

Compound b

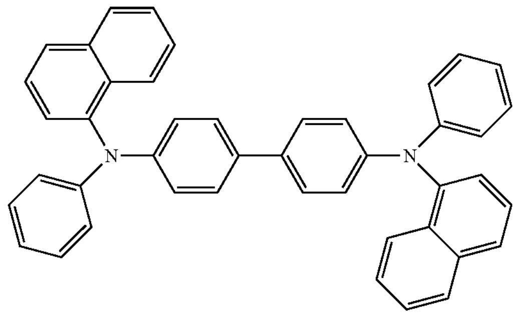

-continued

Compound c

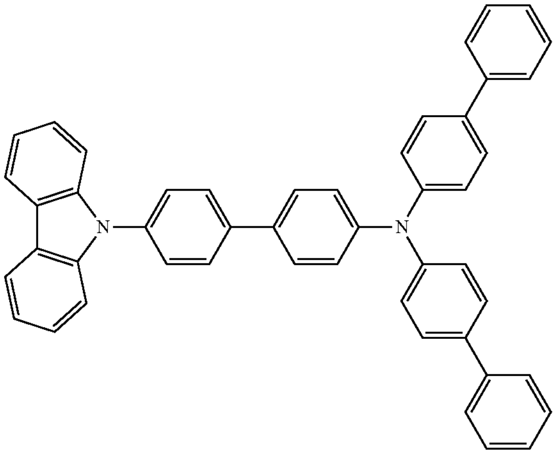

Compound d

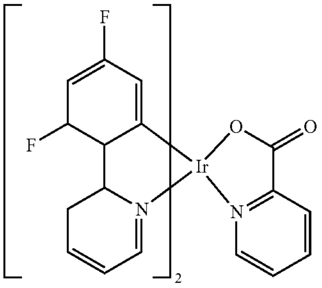

Compound e

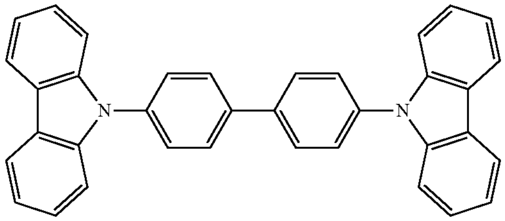

Compound f

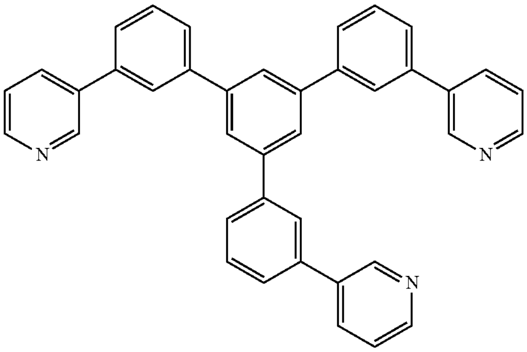

-continued

Comparative Compound 1

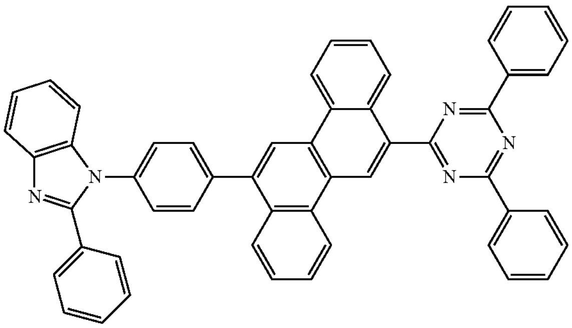

Comparative Compound 2

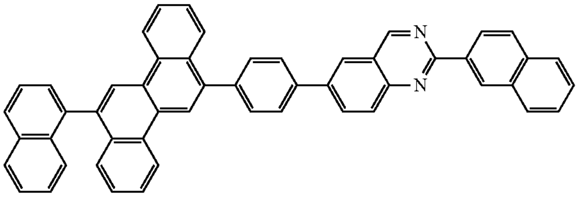

Performance Evaluation of the OLED Device

According to the current densities and brightness of the OLED device under different voltages, the operating voltage V and current efficiency CE (cd/A) of the OLED device at a current density (10 mA/cm$^2$) were obtained. The lifetime LT95 (h) was obtained by measuring the time taken for the OLED device to reach 95% of its initial brightness (at 50 mA/cm$^2$). Measured data is shown in Table 2.

TABLE 2

| OLED Device | Electron Transport Layer | V (V) | CE (cd/A) | LT95 (h) |
|---|---|---|---|---|
| Application Example 1 | 1 | 4.06 | 15.9 | 67 |
| Application Example 2 | 2 | 4.07 | 16.1 | 68 |
| Application Example 3 | 3 | 4.03 | 15.6 | 64 |
| Application Example 4 | 4 | 4.08 | 15.7 | 65 |
| Application Example 5 | 5 | 4.02 | 15.9 | 66 |
| Application Example 6 | 6 | 4.04 | 15.8 | 64 |
| Application Example 7 | 7 | 4.13 | 14.8 | 58 |
| Application Example 8 | 8 | 4.05 | 15.8 | 65 |
| Application Example 9 | 9 | 4.06 | 15.9 | 66 |
| Application Example 10 | 10 | 4.04 | 15.7 | 62 |
| Application Example 11 | 11 | 4.12 | 14.9 | 58 |
| Application Example 12 | 12 | 4.05 | 15.8 | 65 |
| Application Example 13 | 13 | 4.06 | 15.9 | 66 |
| Application Example 14 | 14 | 4.04 | 15.7 | 62 |
| Application Example 15 | 15 | 4.10 | 15.0 | 59 |
| Application Example 16 | 16 | 4.04 | 15.9 | 66 |

TABLE 2-continued

| OLED Device | Electron Transport Layer | V (V) | CE (cd/A) | LT95 (h) |
|---|---|---|---|---|
| Application Example 17 | 17 | 4.05 | 16.0 | 67 |
| Application Example 18 | 18 | 4.03 | 15.8 | 64 |
| Comparative Example 1 | Comparative Compound 1 | 4.19 | 14.1 | 52 |
| Comparative Example 2 | Comparative Compound 2 | 4.27 | 13.7 | 50 |

As can be seen from Table 2, the OLED devices provided by the present disclosure have relatively low driving voltage, relatively high luminescence efficiency and relatively long lifetimes, where the operating voltage is less than or equal to 4.13 V, the current efficiency CE is greater than or equal to 14.8 cd/A, and the lifetime LT95 is greater than or equal to 58 h. Compared with those in Comparative Examples 1 and 2, the OLED devices using the compounds of the present disclosure have reduced operating voltage and improved efficiency and lifetimes for the following reasons: the organic compounds of the present disclosure have relatively deep LUMO energy levels so that more smooth electron injection is achieved and the operating voltage of the device is reduced; the organic compounds have relatively deep HOMO values and can effectively block holes and restrict the holes in the light-emitting region to be recombined with electrons, which is conducive to widening a light-emitting recombination region and improving the luminescence efficiency of the device. Meanwhile, the organic compounds provided by the present disclosure have good thermal stability and a good film-forming property, which is conducive to the stability of the device and improves the lifetime of the device.

The applicant has stated that although the organic compound and the application thereof in the present disclosure are described through the preceding embodiments, the present disclosure is not limited to the preceding embodiments, which means that the implementation of the present disclosure does not necessarily depend on the preceding embodiments. It should be apparent to those skilled in the art that any improvements made to the present disclosure, equivalent replacements of raw materials selected in the present disclosure and additions of adjuvant ingredients thereof and selections of specific methods, etc., all fall within the protection scope and the disclosure scope of the present disclosure.

What is claimed is:

1. An organic compound having a structure represented by Formula I:

Formula I

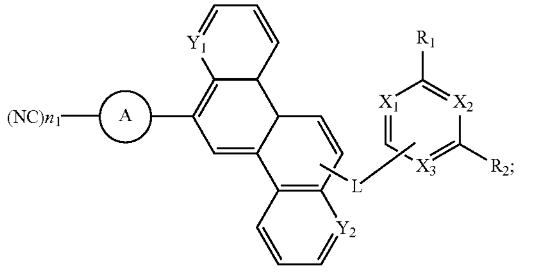

wherein the ring A is any one of biphenylene, terphenylene, pyridylene, phenylene-pyridylene and phenylene-naphthylene;

wherein $Y_1$ and $Y_2$ are selected from a N atom;

wherein L is selected from substituted or unsubstituted C6-C20 aryl, or substituted or unsubstituted C5-C30 heteroaryl;

wherein $X_1$ to $X_3$ are independently selected from the C atom or the N atom, and at least one of $X_1$ to $X_3$ is N;

wherein $R_1$ and $R_2$ are independently selected from substituted or unsubstituted C6-C30 aryl or substituted or unsubstituted C5-C30 heteroaryl; and wherein $n_1$ is an integer from 1 to 3.

2. The organic compound according to claim 1, wherein the organic compound has a structure represented by Formula II:

Formula II

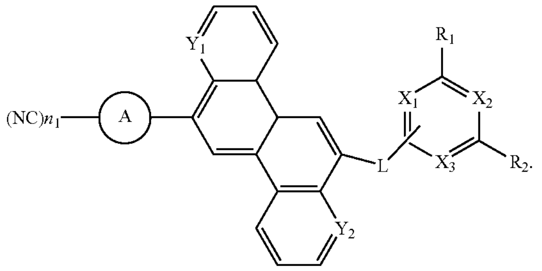

3. The organic compound according to claim 1, wherein when the substituted or unsubstituted C6-C20 aromatic ring, substituted or unsubstituted C5-C30 aromatic heterocycle, substituted or unsubstituted C6-C20 aryl, substituted or unsubstituted C5-C30 heteroaryl, substituted or unsubstituted C6-C30 aryl or substituted or unsubstituted C5-C30 heteroaryl contains a substituent, the substituent is selected from at least one of deuterium, cyano, halogen, unsubstituted or halogenated C1-C10 linear or branched alkyl, unsubstituted or halogenated C1-C10 alkoxy, C1-C10 alkylthio, C6-C20 aryl, C5-C20 heteroaryl or C6-C18 arylamine.

4. The organic compound according to claim 1, wherein L is selected from any one of phenylene, biphenylene, naphthylene, terphenylene and pyridylene.

5. The organic compound according to claim 1, wherein two of $X_1$ to $X_3$ are N or all of $X_1$ to $X_3$ are N.

6. The organic compound according to claim 1, wherein $R_1$ and $R_2$ are independently selected from any one of the following groups:

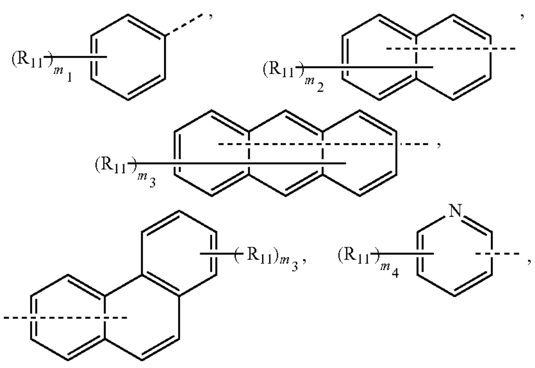

-continued

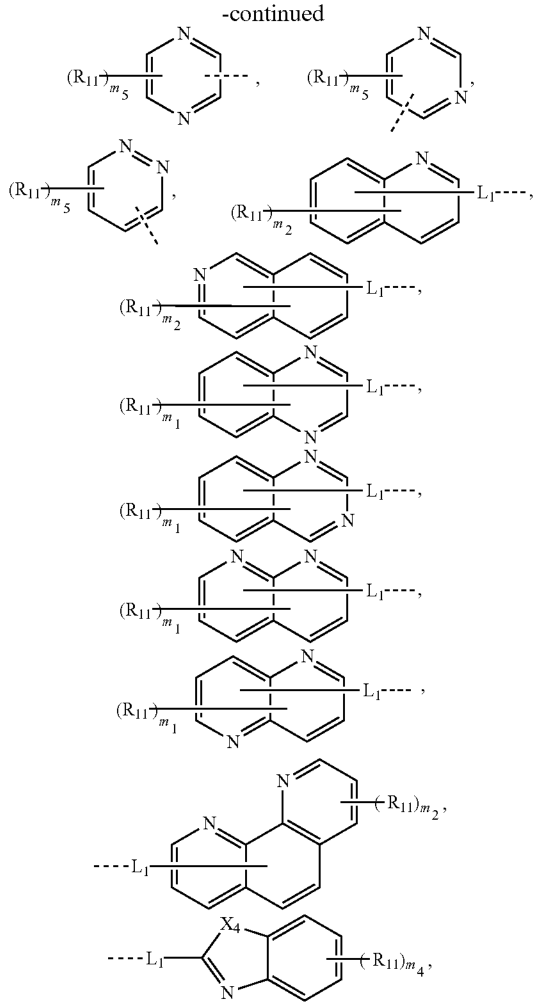

,

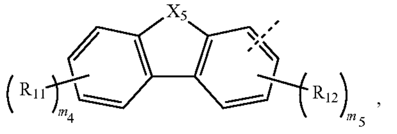

and

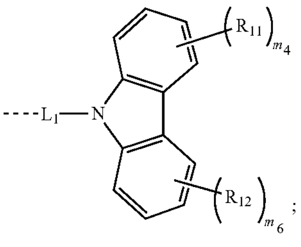

;

wherein the dashed line represents a linkage site of the group;

wherein $L_1$ is selected from any one of a single bond or substituted or unsubstituted C6-C20 arylene;

wherein $X_4$ is selected from O, S or $NR_{N1}$;

wherein $X_5$ is selected from O, S, $NR_{N2}$ or $CR_{C3}R_{C4}$;

wherein $R_{N1}$, $R_{N2}$, $R_{C3}$ and $R_{C4}$ are each independently selected from any one of hydrogen, substituted or unsubstituted C1-C20 linear or branched alkyl, substituted or unsubstituted C6-C20 aryl or substituted or unsubstituted C5-C20 heteroaryl;

wherein $R_{11}$ and $R_{12}$ are each independently selected from any one of deuterium, cyano, halogen, unsubstituted or halogenated C1-C10 linear or branched alkyl, unsubstituted or halogenated C1-C10 alkoxy, C1-C10 alkylthio, C6-C20 aryl, C5-C20 heteroaryl or C6-C18 arylamine;

wherein $m_1$ is selected from an integer from 0 to 5;

wherein $m_2$ is selected from an integer from 0 to 6;

wherein $m_3$ is selected from an integer from 0 to 9;

wherein $m_4$ and $m_6$ are each independently selected from an integer from 0 to 4; and wherein $m_5$ is selected from an integer from 0 to 3.

7. The organic compound according to claim 6, wherein $R_1$ and $R_2$ are independently selected from any one of the following substituted or unsubstituted groups:

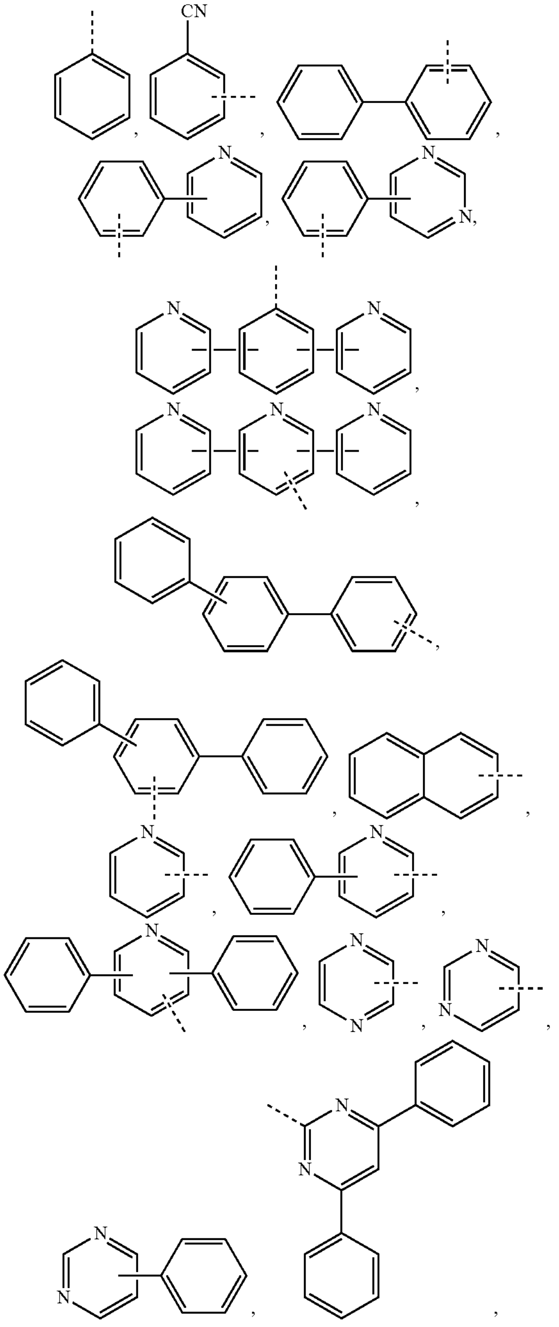

,

-continued

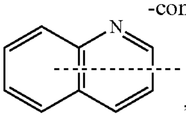,
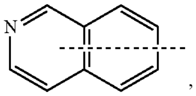,
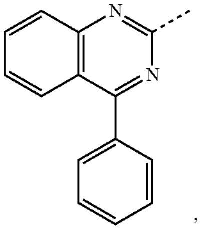
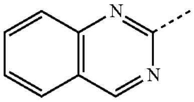,
,
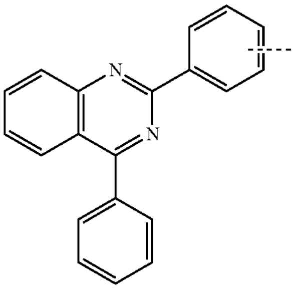
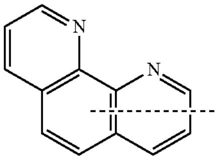,
,
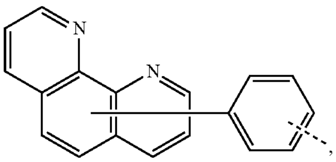,
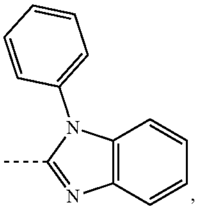,
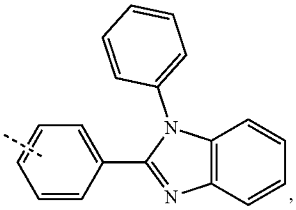,
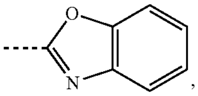,
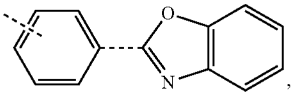,
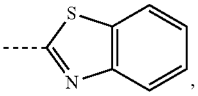, -continued

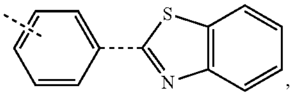,
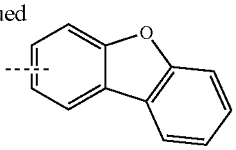,
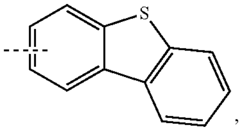,
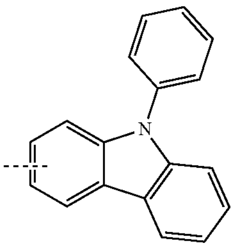,
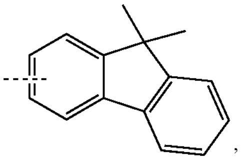,
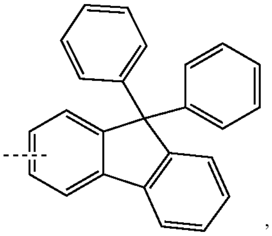,
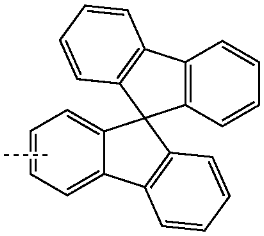, and
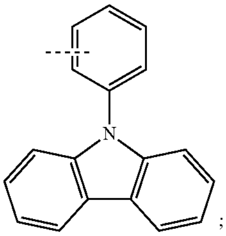;

wherein the dashed line represents a linkage site of the group;

wherein the substituted substituents are each independently selected from at least one of deuterium, cyano, halogen, unsubstituted or halogenated C1-C10 linear or branched alkyl, unsubstituted or halogenated C1-C10 alkoxy, C1-C10 alkylthio, C6-C20 aryl, C2-C20 heteroaryl or C6-C18 arylamine.

8. The organic compound according to claim 1, wherein the organic compound is any one of the following compounds:

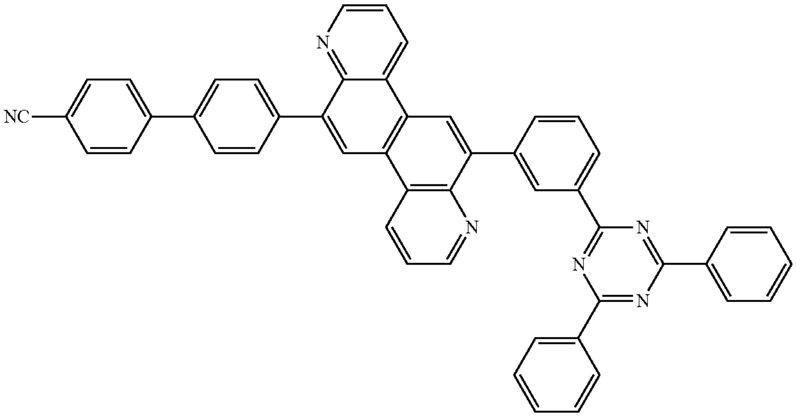 [SMILES: N#Cc1ccc(-c2ccc(-c3cc4c5cccnc5c(-c5cccc(-c6nc(-c7ccccc7)nc(-c7ccccc7)n6)c5)cc4c4cccnc34)cc2)cc1]

-continued
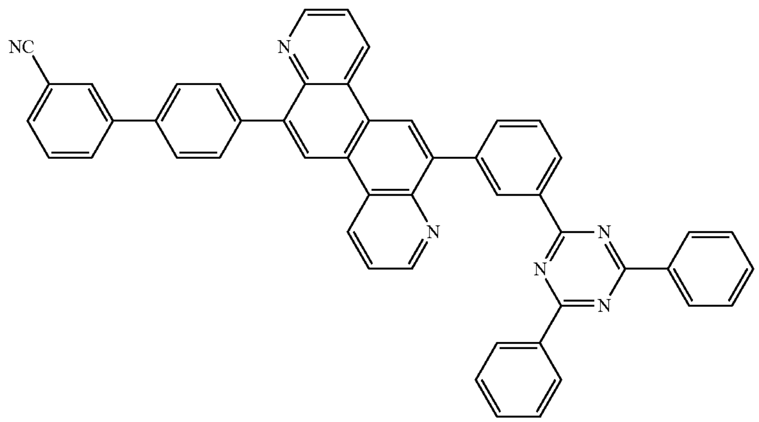
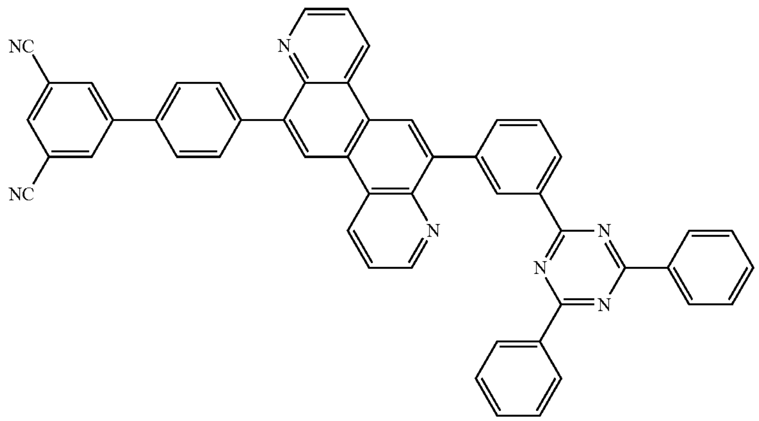
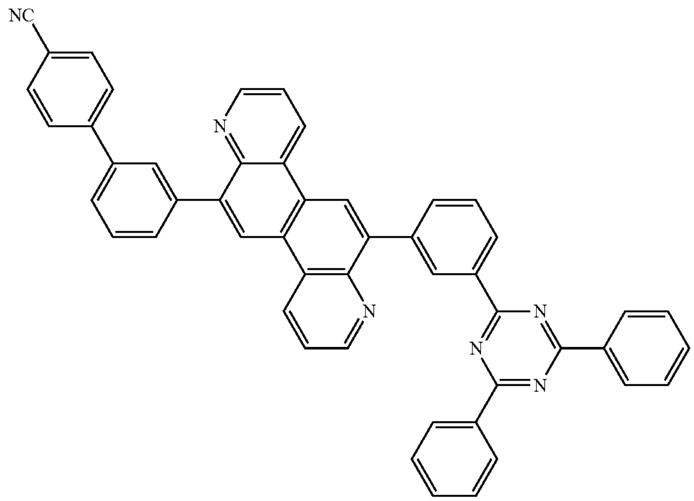

-continued
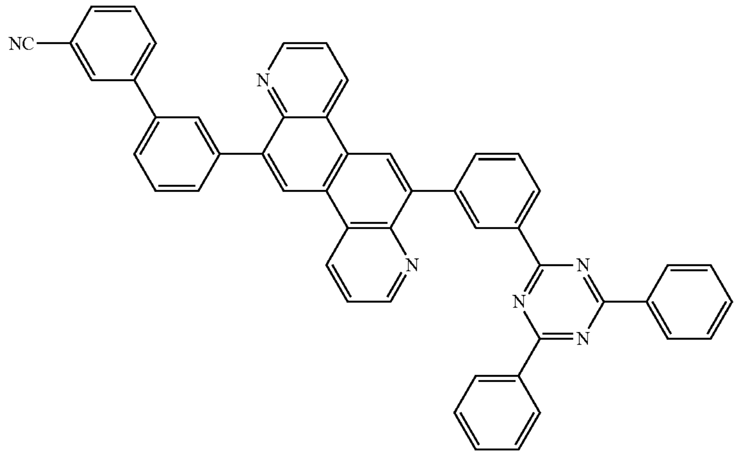
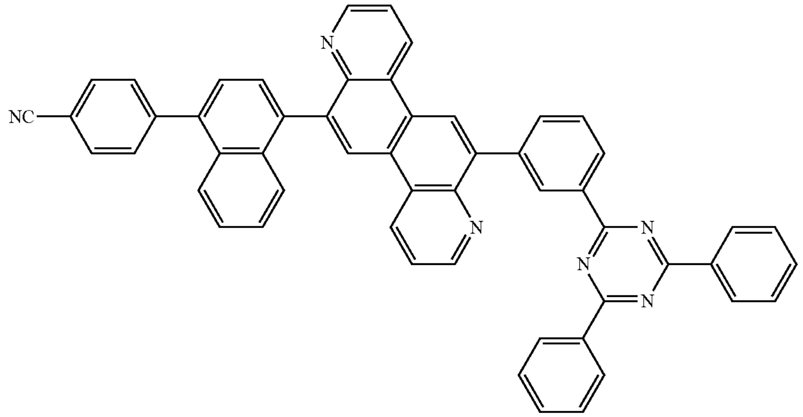
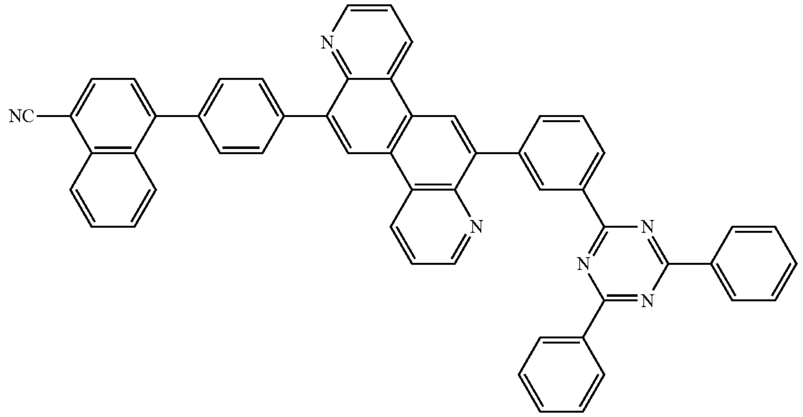
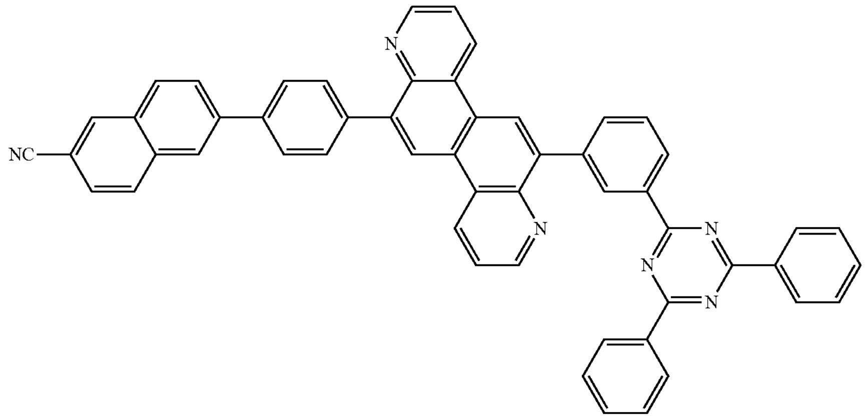

-continued
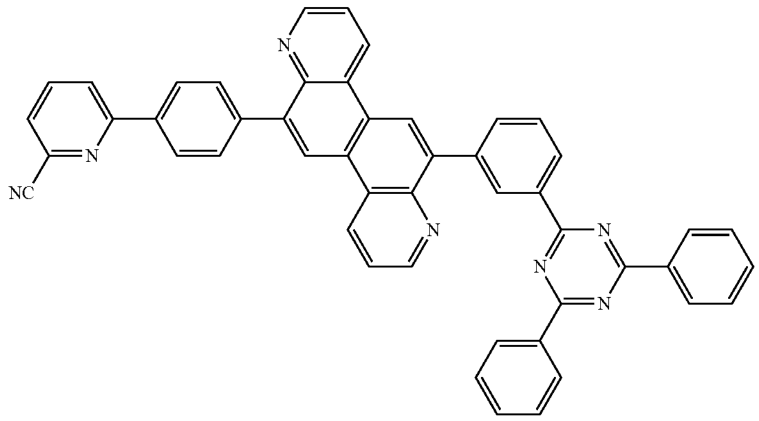
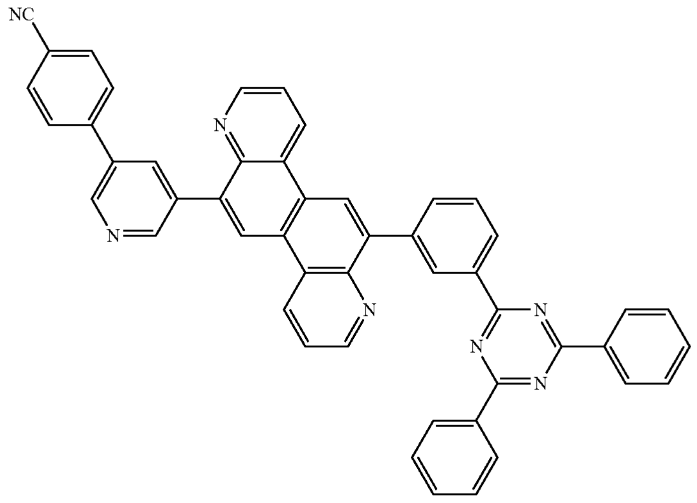
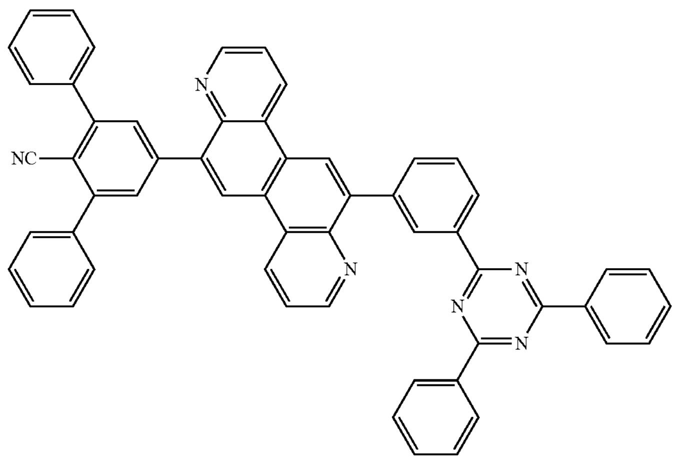

-continued
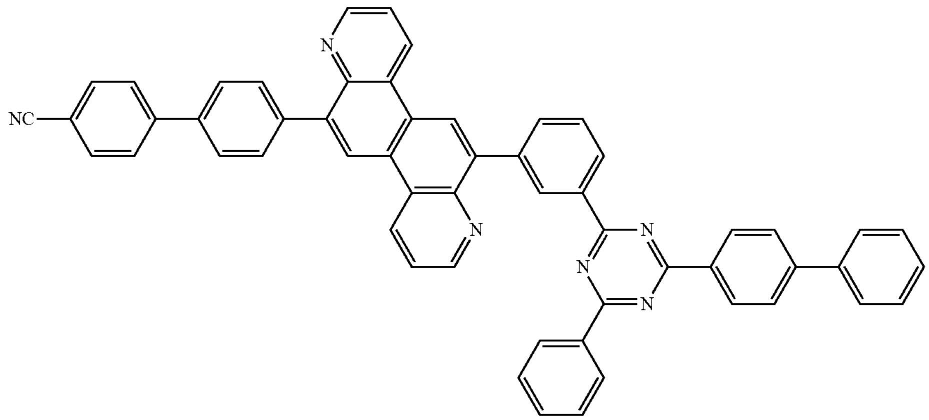
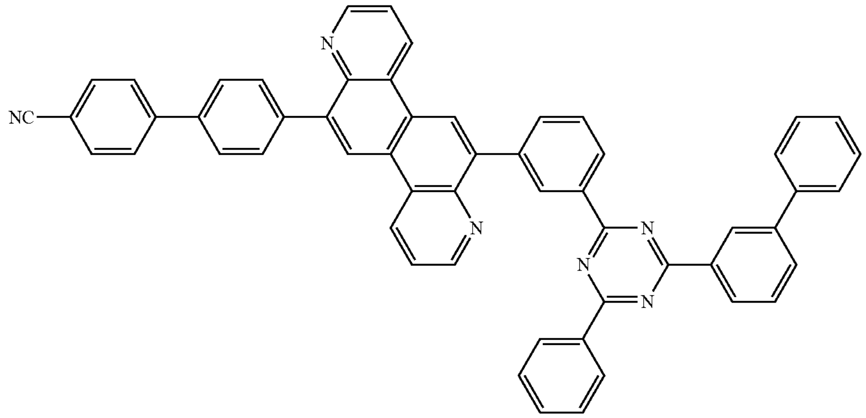
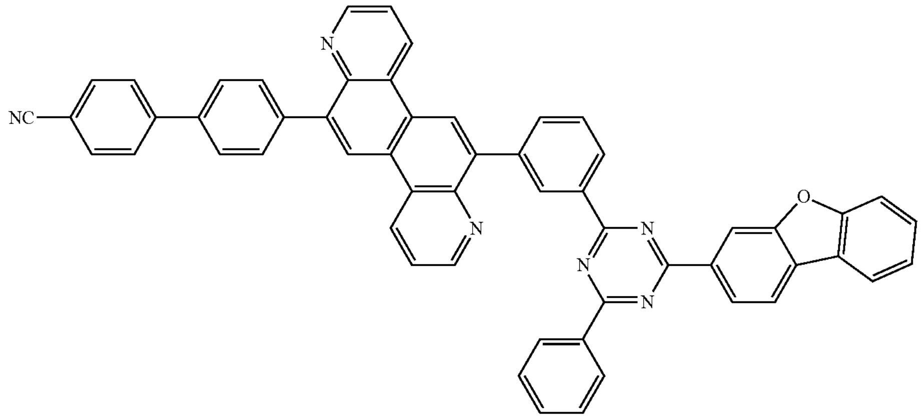
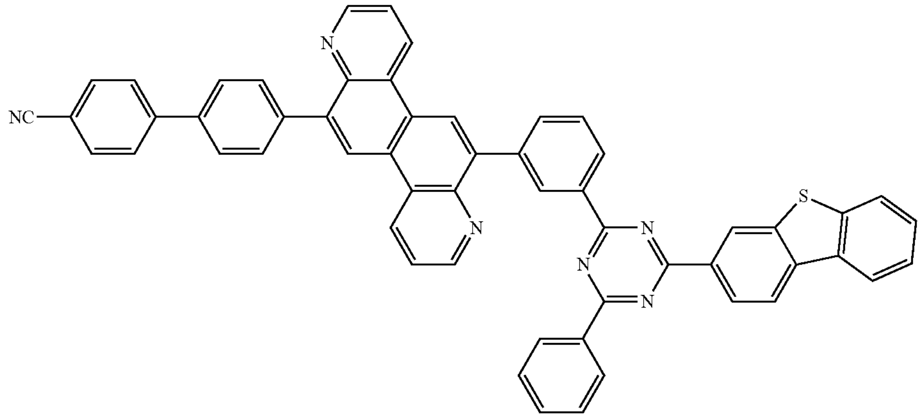

-continued
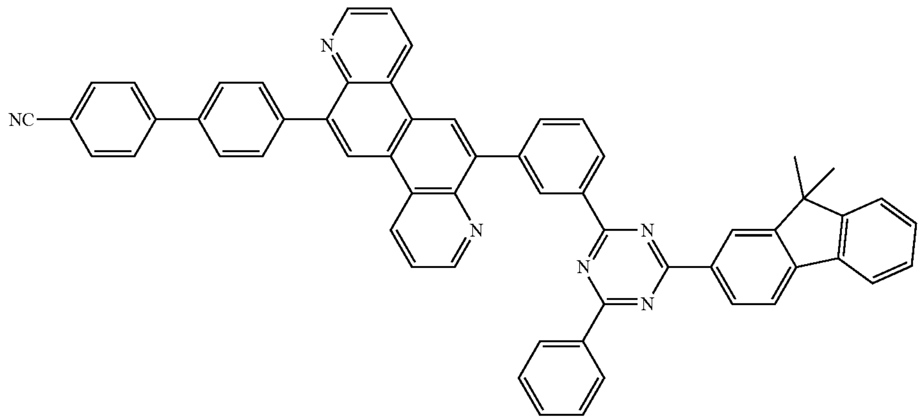
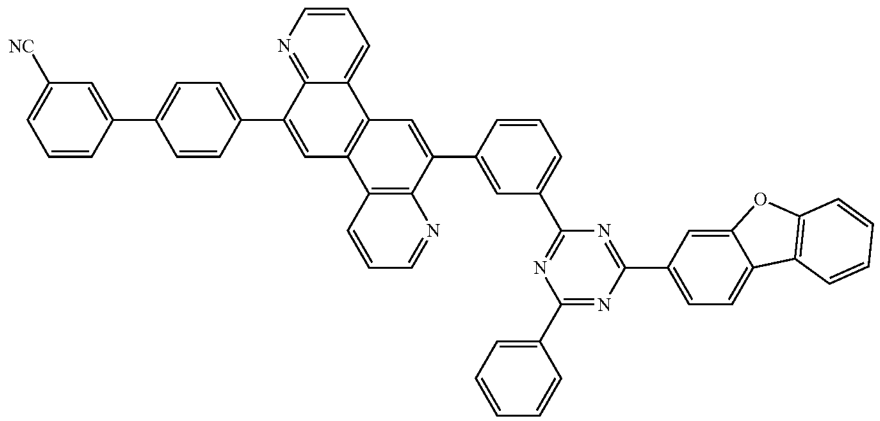
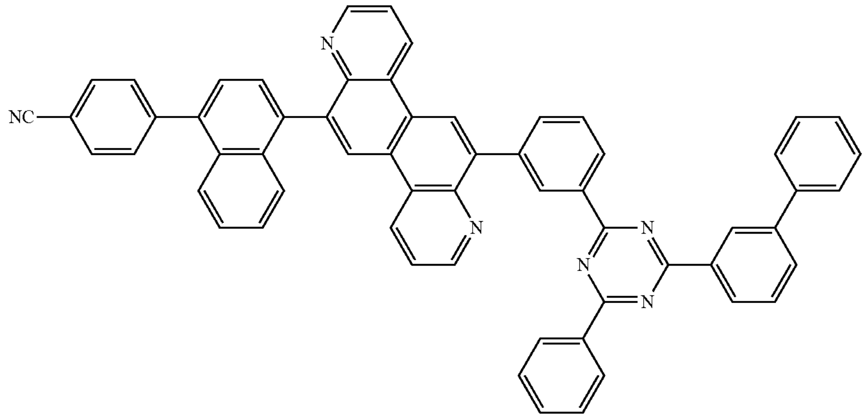
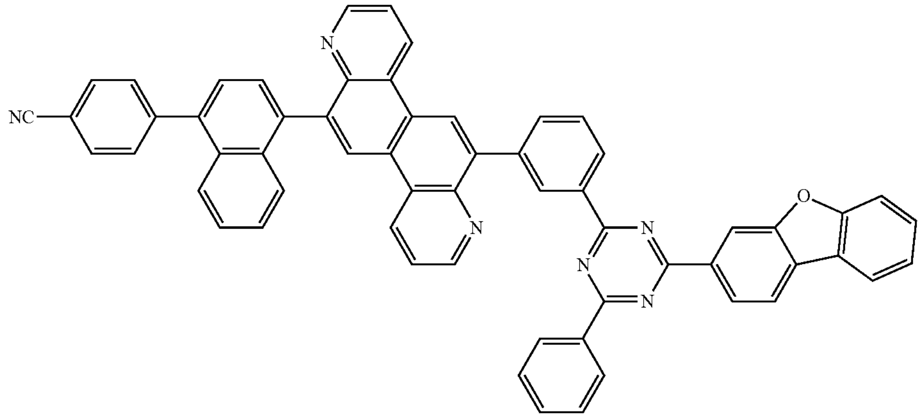

-continued
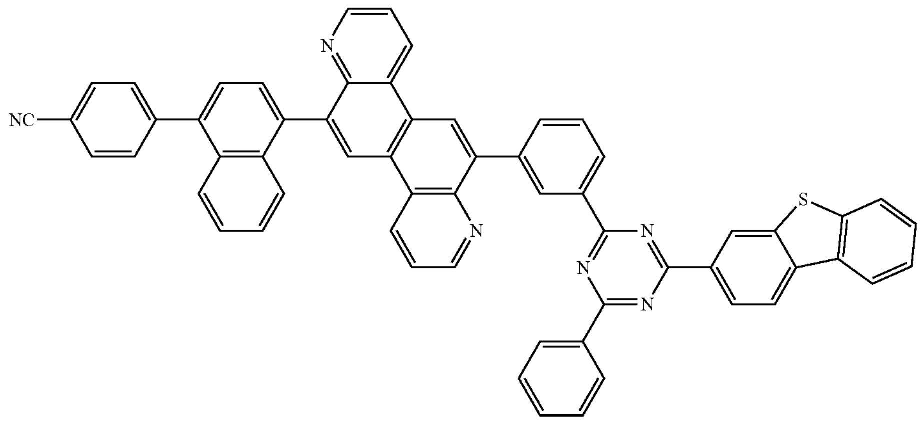
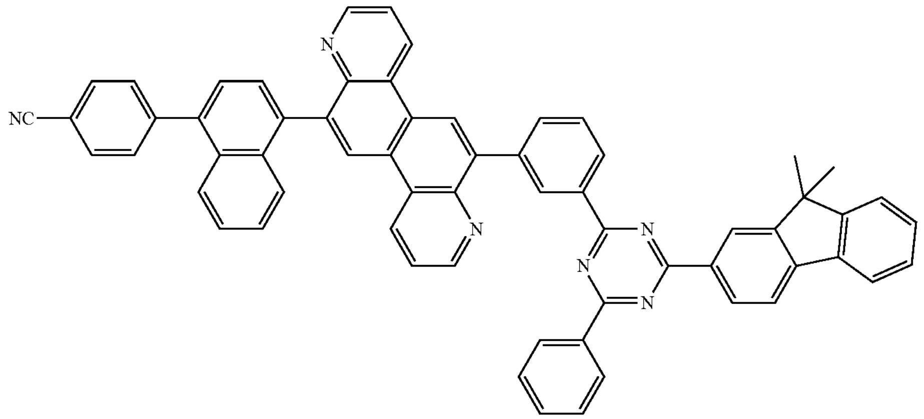
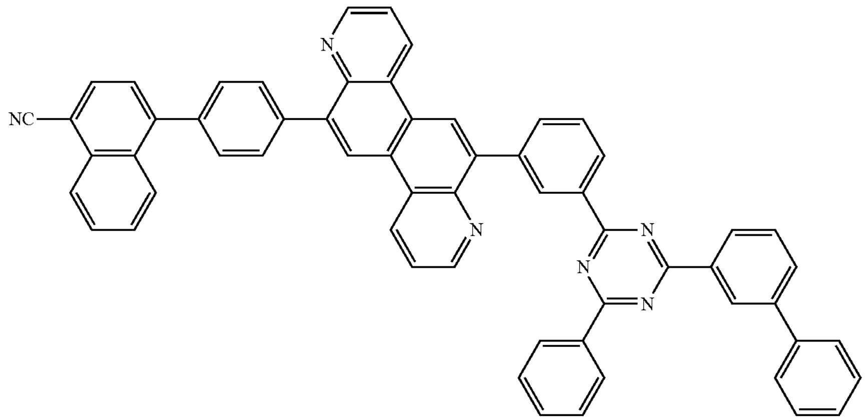
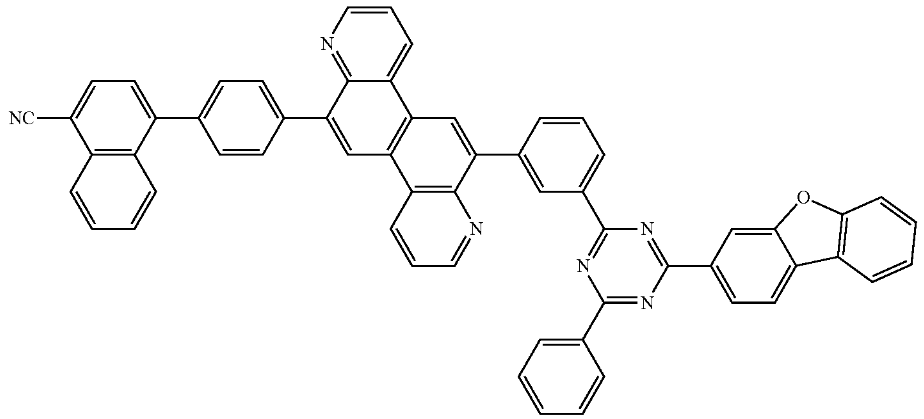

-continued
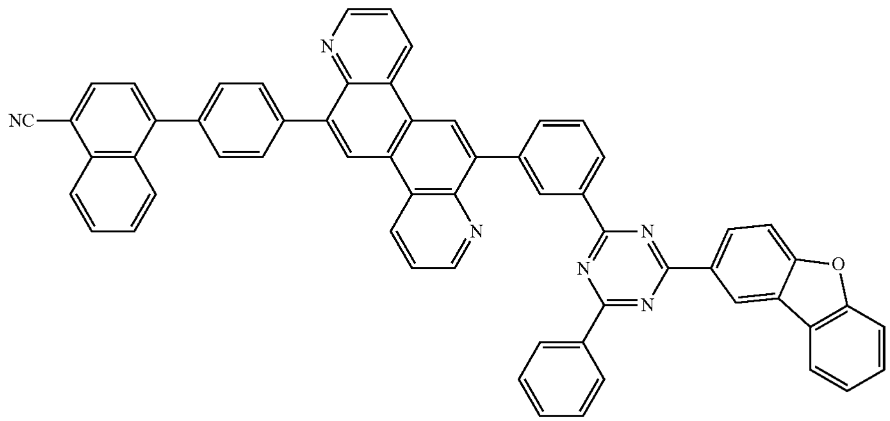
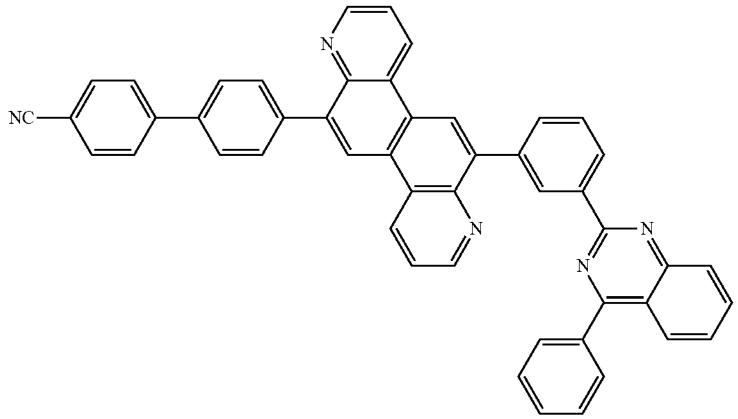
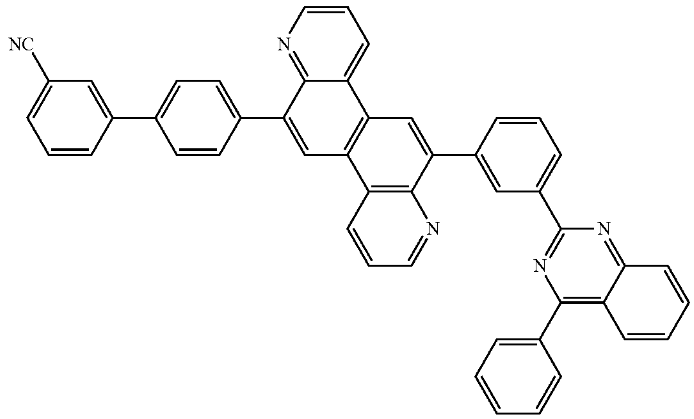
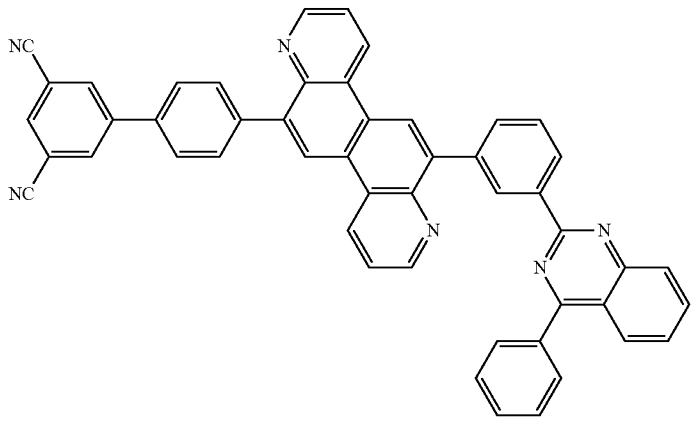

-continued
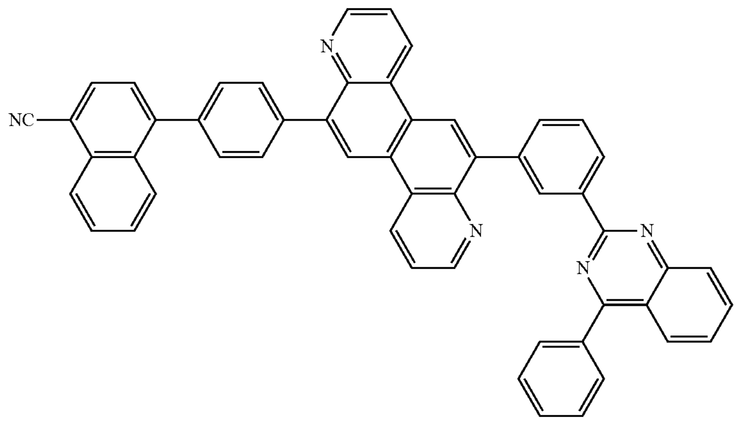
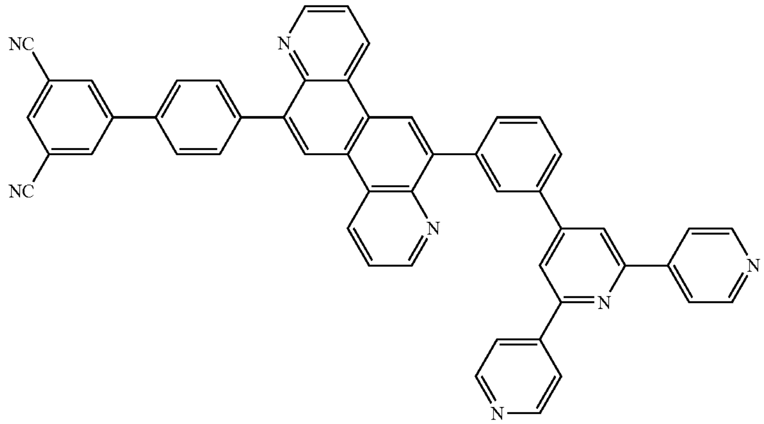
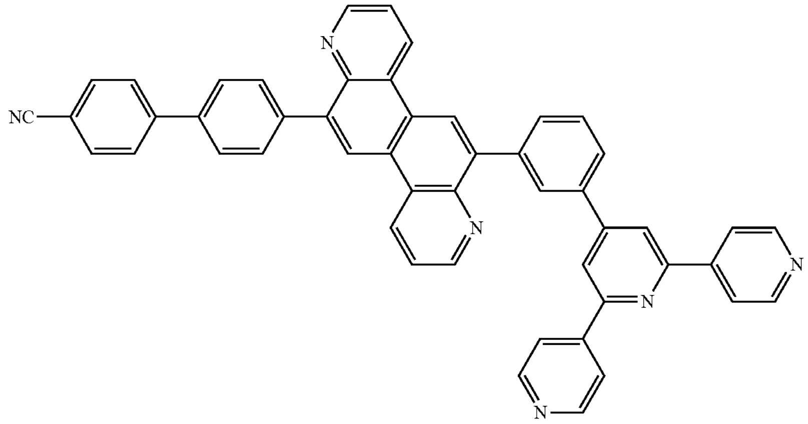
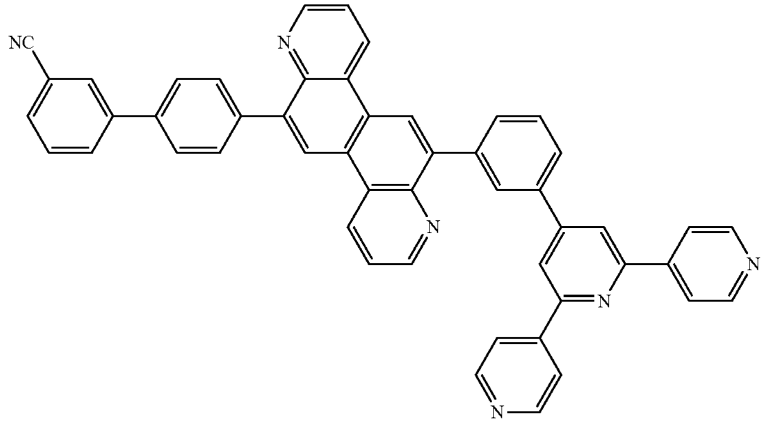

-continued
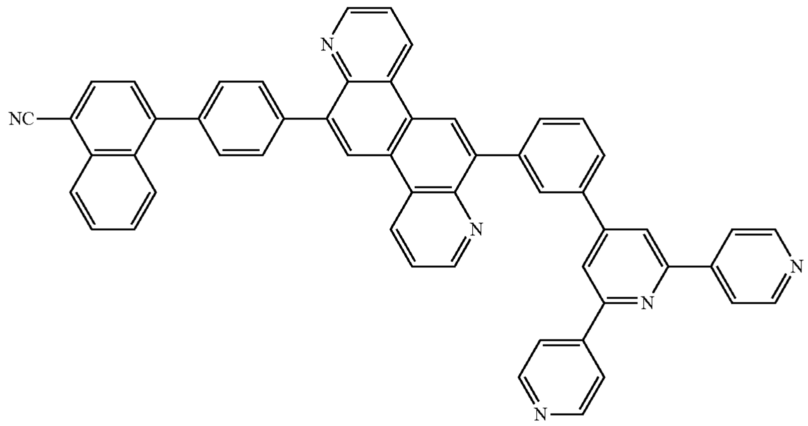
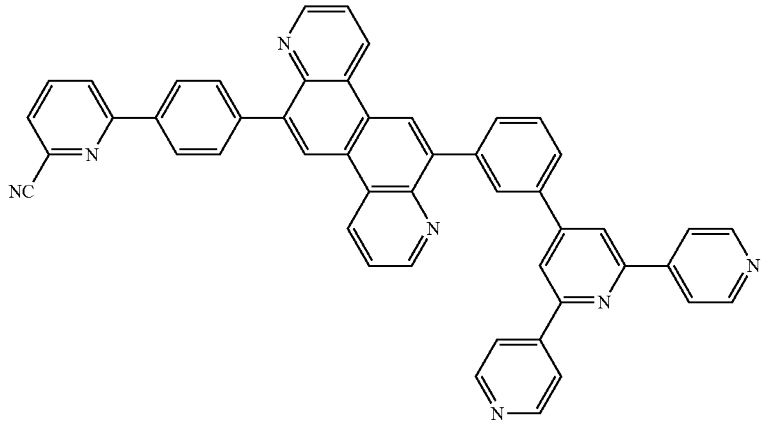
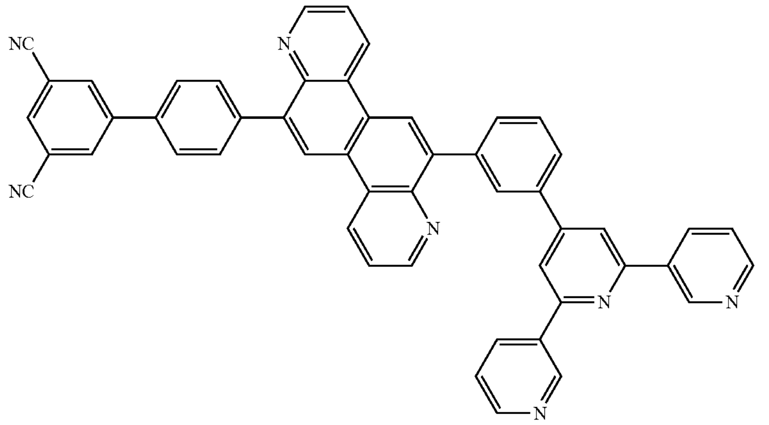
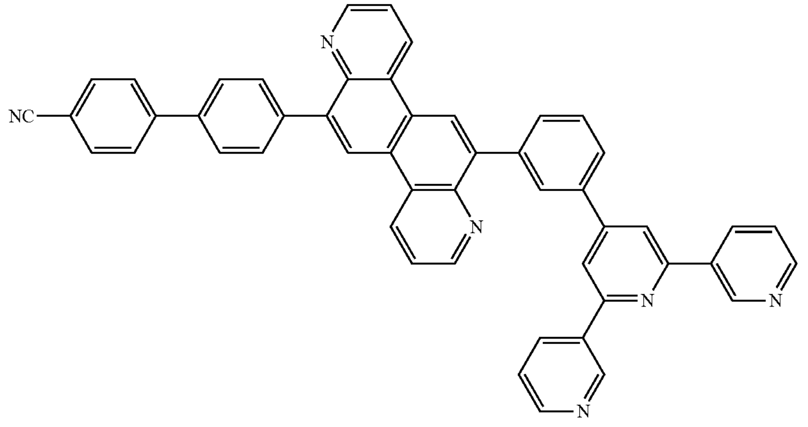

-continued

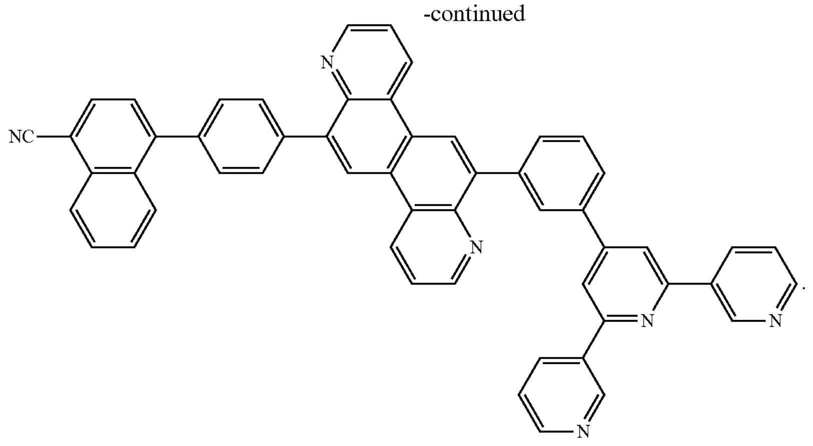

9. A material of an electron transport layer, comprising the organic compound according to claim 1.

10. A material of a hole blocking layer, comprising the organic compound according to claim 1.

11. An OLED device, comprising an anode, a cathode and an organic thin film layer disposed between the anode and the cathode, wherein a material of the organic thin film layer comprises the organic compound according to claim 1.

12. The OLED device according to claim 11, wherein the organic thin film layer comprises an electron transport layer whose material comprises the organic compound.

13. The OLED device according to claim 11, wherein the organic thin film layer comprises a hole blocking layer whose material comprises the organic compound.

14. A display panel, comprising the OLED device according to claim 11, wherein the OLED device comprises the anode, the cathode and the organic thin film layer disposed between the anode and the cathode, wherein the material of the organic thin film layer comprises the organic compound.

15. An electronic apparatus, comprising the display panel according to claim 14, wherein the display panel comprises the OLED device which comprises the anode, the cathode and the organic thin film layer disposed between the anode and the cathode, wherein the material of the organic thin film layer comprises the organic compound.

* * * * *